United States Patent
Planey et al.

(10) Patent No.: US 11,830,583 B2
(45) Date of Patent: Nov. 28, 2023

(54) SYSTEMS AND METHODS FOR CHARACTERIZING EXTRACELLULAR VESICLE (EV) POPULATION BY PREDICTING WHETHER THE EV ORIGINATES FROM B, T, OR DENDRITIC CELLS

(71) Applicant: Mantra Bio, Inc., San Francisco, CA (US)

(72) Inventors: Catherine RoseMary Planey, San Francisco, CA (US); Alexander Fen Mok, San Francisco, CA (US)

(73) Assignee: Mantra Bio Inc., South San Francisco, CA (US)

( * ) Notice: Subject to any disclaimer, the term of this patent is extended or adjusted under 35 U.S.C. 154(b) by 1316 days.

(21) Appl. No.: 15/865,166

(22) Filed: Jan. 8, 2018

(65) Prior Publication Data
US 2018/0276339 A1    Sep. 27, 2018

Related U.S. Application Data

(60) Provisional application No. 62/443,540, filed on Jan. 6, 2017.

(51) Int. Cl.

| | |
|---|---|
| *G16B 40/10* | (2019.01) |
| *G16H 50/20* | (2018.01) |
| *G06N 5/04* | (2023.01) |
| *G16B 40/00* | (2019.01) |
| *G16H 50/70* | (2018.01) |
| *G16H 20/10* | (2018.01) |
| *G16B 40/20* | (2019.01) |
| *G16B 40/30* | (2019.01) |

(52) U.S. Cl.
CPC .............. *G16B 40/10* (2019.02); *G06N 5/04* (2013.01); *G16B 40/00* (2019.02); *G16B 40/20* (2019.02); *G16H 20/10* (2018.01); *G16H 50/20* (2018.01); *G16H 50/70* (2018.01); *G16B 40/30* (2019.02)

(58) Field of Classification Search
None
See application file for complete search history.

(56) References Cited

PUBLICATIONS

Andreu-Perez, Javier, et al. "Big data for health." IEEE journal of biomedical and health informatics 19.4 (2015): 1193-1208.*
Keerthikumar, Shivakumar. "ExoCarta: a web-based compendium of exosomal cargo." Journal of molecular biology 428.4 (2016): 688-692.*
Klinke, David J. "Inferring alterations in cell-to-cellcommunication in HER2+ breast cancer using secretome profiling of three cell models." Biotechnology and bioengineering 111.9 (2014): 1853-1863.*
"Int'l Application Serial No. PCT/US18/012841, Notification of Transmittal of Int'l Search Report and Written Opinion dated Jul. 12, 2018", 7 pgs.

* cited by examiner

*Primary Examiner* — G Steven Vanni
(74) *Attorney, Agent, or Firm* — Adriano & Associates

(57) ABSTRACT

Methods and systems for extracellular vesicle characterization are provided herein. Embodiments of the methods include inputting measured physical, biological, or chemical aspects of extracted extracellular vesicles. Next, an information architecture that characterizes relationships between biological entities and diseases in humans or other vertebrates is generated. Then, relationships between the measured physical, biological, or chemical aspects of the isolated extracellular vesicles with the information architecture are automatically inferred, thereby characterizing extracellular vesicles.

3 Claims, 52 Drawing Sheets

Schematic of predicted EV therapeutic compound delivery vehicle and possible companion intravesicle therapeutic agent

Columns: Genes that strongly differentiated
between healthy and lung cancer patients NA is listed if no HUGO gene symbol to be translated from
Ensembl ID. Duplicated gene symbols indicated two distinct
originating Ensembl IDs for one HUGE gene symbol Columns: Genes that strongly differentiated between healthy and lung cancer patients from Figure 10

NA is listed if no HUGO gene symbol to be translated from Ensembl ID. Duplicated gene symbols indicated two distinct originating Ensembl IDs for one HUGE gene symbol Clustering of cells and EV total RNA-seq gene expression from different cell type cultures using list of 1300 cancer-related genes "Height" denotes the distance (a larger height indicates a larger distance between samples).

"Cell" indicates a cell extraction sample, while "exo" indicates an EV isolated and extracted sample.

Clustering of cells and EV total RNA-seq gene expression from different cell type cultures using top-varying genes as feature list "Height" denotes the distance (a larger height indicates a larger distance between samples).

"Cell" indicates a cell extraction sample, while "exo" indicates an EV isolated and extracted sample.

FIG. 15 A

TABLE 1

Gene signature list of mRNAs that are differentially present in different immune cell types

| | | | | |
|---|---|---|---|---|
| ABCB4 | BCL2AI | CCR6 | CD96 | CXCL3 |
| ABCB9 | BCL7A | CCR7 | CDA | CXCL5 |
| ACAPI | BENDS | CD160 | CDC2SA | CXCL9 |
| ACHE | BFSPI | CD180 | CDH12 | CXCRI |
| ACPS | BHLHE41 | CD19 | CDHRI | CXCR2 |
| ADAM28 | BIRC3 | CDIA | CDK6 | CXCR5 |
| ADAMDECI | BLK | CDIB | CEACAM3 | CXCR6 |
| ADAMTS3 | BMP2K | CDIC | CEACAM8 | CXorfS7 |
| ADRB2 | BPI | CDID | CEMPI | CYP27AI |
| AIFI | BRAF | CDIE | CFP | CYP27BI |
| AIM2 | BRSK2 | CD2 | CHI3LI | DACHI |
| ALOX15 | BSTI | CD209 | CHI3L2 | DAPK2 |
| ALOX5 | BTNL8 | CD22 | CHSTIS | DCSTAMP |
| AMPDI | C11orf80 | CD244 | CHST7 | DEFA4 |
| ANGPT4 | C1orfS4 | CD247 | CLC | DENNDSB |
| ANKRDSS | C3AR1 | CD27 | CLCA3P | DEPDCS |
| APOBEC3A | C5AR1 | CD28 | CLEC10A | DGKA |
| APOBEC3G | C5AR2 | CD300A | CLEC2D | DHRSII |
| APOL3 | CA8 | CD33 | CLEC4A | DHXS8 |
| APOL6 | CAMP | CD37 | CLEC7A | DPEP2 |
| AQP9 | CASPS | CD38 | CLIC2 | DPP4 |
| ARHGAP22 | CCDC102B | CD3D | CMAI | DSCI |
| ARRBI | CCLI | CD3E | COL8A2 | DUSP2 |
| ASGRI | CCL13 | CD3G | COLQ | EAF2 |
| ASGR2 | CCL14 | CD4 | CPA3 | EBI3 |
| ATHLI | CCL17 | CD40 | CR2 | EFNAS |
| ATP8B4 | CCL18 | CD40LG | CREBS | EGR2 |
| ATXN8OS | CCL19 | CD5 | CRISP3 | ELANE |
| AZUI | CCL20 | CD6 | CRTAM | EMRI |
| BACH2 | CCL22 | CD68 | CRYBBI | EMR2 |
| BANKI | CCL23 | CD69 | CSFI | EMR3 |
| BARX2 | CCL4 | CD7 | CSF2 | EPB41 |
| BCL11B | CCL5 | CD70 | CSF3R | EPHAI |

FIG. 15 B

| | | | | |
|---|---|---|---|---|
| BCL2A1 | CCL7 | CD72 | CST7 | EPN2 |
| BCL7A | CCL8 | CD79A | CTLA4 | ETS1 |
| BEND5 | CCND2 | CD79B | CTSG | ETV3 |
| BFSP1 | CCR10 | CD80 | CTSW | FAIM3 |
| BHLHE41 | CCR2 | CD86 | CXCL10 | FAM124B |
| BIRC3 | CCR3 | CD8A | CXCL11 | FAM174B |
| BLK | CCR5 | CD8B | CXCL13 | FAM198B |
| FAM212B | GPR1 | IFNA10 | KLRC3 | MAST1 |
| FAM65B | GPR171 | IFNG | KLRC4 | MBL2 |
| FASLG | GPR18 | IGHD | KLRD1 | MEFV |
| FBXL8 | GPR183 | IGHE | KLRF1 | MEP1A |
| FCER1A | GPR19 | IGHM | KLRG1 | MGAM |
| FCER2 | GPR25 | IGKC | KLRK1 | MICAL3 |
| FCGR2B | GPR65 | IGLL3P | KRT18P50 | MMP12 |
| FCGR3B | GPR97 | IGSF6 | KYNU | MMP25 |
| FCN1 | GRAP2 | IL12B | LAG3 | MMP9 |
| FCRL2 | GSTT1 | IL12RB2 | LAIR2 | MNDA |
| FES | GUSBP11 | IL17A | LAMP3 | MROH7 |
| FFAR2 | GYPE | IL18R1 | LAT | MS4A1 |
| FLJ13197 | GZMA | IL18RAP | LCK | MS4A2 |
| FLT3LG | GZMB | IL1A | LEF1 | MS4A3 |
| FLVCR2 | GZMH | IL1B | LHCGR | MS4A6A |
| FOSB | GZMK | IL1RL1 | LILRA2 | MSC |
| FOXP3 | GZMM | IL21 | LILRA3 | MXD1 |
| FPR1 | HAL | IL26 | LILRA4 | MYB |
| FPR2 | HCK | IL2RA | LILRB2 | MZB1 |
| FPR3 | HDC | IL2RB | LIME1 | NAALADL1 |
| FRK | HESX1 | IL3 | LINC00597 | NCF2 |
| FRMD4A | HHEX | IL4 | LINC00921 | NCR3 |
| FRMD8 | HIC1 | IL4R | LOC100130100 | NFE2 |
| FZD2 | HIST1H2AE | IL5 | LOC126987 | NIPSNAP3B |
| FZD3 | HIST1H2BG | IL5RA | LRMP | NKG7 |
| GAL3ST4 | HK3 | IL7 | LST1 | NLRP3 |
| GALR1 | HLA-DOB | IL7R | LTA | NMBR |
| GFI1 | HLA-DQA1 | IL9 | LTB | NME8 |
| GGT5 | HMGB3P30 | IRF8 | LTC4S | NOD2 |
| GIPR | HNMT | ITK | LY86 | NOX3 |
| GNG7 | HOXA1 | KCNA3 | LY9 | NPAS1 |
| GNLY | HPGDS | KCNG2 | MAGEA11 | NPIPB15 |
| GPC4 | HPSE | KIAA0226L | MAK | NPL |

FIG. 15 C

| GPR1 | HRH1 | KIAA0754 | MAN1A1 | NR4A3 |
|---|---|---|---|---|
| GPR171 | HSPA6 | KIR2DL1 | MANEA | NTN3 |
| GPR18 | HTR2B | KIR2DL4 | MAP3K13 | NTRK1 |
| GPR183 | ICA1 | KIR2DS4 | MAP4K1 | ORC1 |
| GPR19 | ICOS | KIR3DL2 | MAP4K2 | OSM |
| GPR25 | IDO1 | KIRREL | MAP9 | P2RX1 |
| GPR65 | IFI44L | KLRB1 | MARCO | P2RX5 |
| P2RY10 | PTPRCAP | SLC12A1 | TPSAB1 | ZNF204P |
| P2RY13 | PTPRG | SLC12A8 | TRAC | ZNF222 |
| P2RY14 | PVRIG | SLC15A3 | TRAF4 | ZNF286A |
| P2RY2 | QPCT | SLC2A6 | TRAT1 | ZNF324 |
| PADI4 | RAB27B | SLC7A10 | TRAV12-2 | ZNF442 |
| PAQR5 | RALGPS2 | SLCO5A1 | TRAV13-1 | SIK1 |
| PASK | RASA3 | SMPD3 | TRAV13-2 | SIRPG |
| PAX7 | RASGRP2 | SMPDL3B | TRAV21 | SIT1 |
| PBXIP1 | RASGRP3 | SOCS1 | TRAV8-6 | SKA1 |
| PCDHA5 | RASSF4 | SP140 | TRAV9-2 | SKAP1 |
| PDCD1 | RCAN3 | SPAG4 | TRBC1 | SLAMF1 |
| PDCD1LG2 | REN | SPIB | TRDC | SLAMF8 |
| PDE6C | RENBP | SPOCK2 | TREM1 | TNFRSF10C |
| PDK1 | REPS2 | SSX1 | TREM2 | TNFRSF11A |
| PGLYRP1 | RGS1 | ST3GAL6 | TREML2 | TNFRSF13B |
| PIK3IP1 | RGS13 | ST6GALNAC4 | TRIB2 | TNFRSF17 |
| PKD2L2 | RNASE2 | ST8SIA1 | TRPM4 | TNFRSF4 |
| PLA1A | RNASE6 | STAP1 | TRPM6 | TNFSF14 |
| PLA2G7 | RPL10L | STEAP4 | TSHR | TNIP3 |
| PLCH2 | RPL3P7 | STXBP6 | TTC38 | ZAP70 |
| PLEKHF1 | RRP12 | TARDBPP1 | TXK | ZBP1 |
| PLEKHG3 | RRP9 | TBX21 | TYR | ZBTB10 |
| PMCH | RSAD2 | TCF7 | UBASH3A | ZBTB32 |
| PNOC | RYR1 | TCL1A | UGT1A8 | ZFP36L2 |
| PPBP | S100A12 | TEC | UGT2B17 | ZNF135 |
| PPFIBP1 | S1PR5 | TEP1 | UPK3A | ZNF165 |
| PRF1 | SAMSN1 | TGM5 | VILL | |
| PRG2 | SCN9A | TLR2 | VNN1 | |
| PRRS5L | SEC31B | TLR7 | VNN2 | |
| PSG2 | SELL | TLR8 | VNN3 | |
| PTGDR | SERGEF | TMEM156 | VPREB3 | |
| PTGER2 | SH2D1A | TMEM255A | WNT5B | |
| PTGIR | SIGLEC1 | TNFAIP6 | WNT7A | |

FIG. 16 A

TABLE 2 microRNAs automatically inferred to be regulators of immume-cell-related mRNAs in Table 1

| | | | |
|---|---|---|---|
| hsa-miR-1185-1-3p | hsa-miR-6505-5p | hsa-miR-664b-3p | hsa-miR-676-3p |
| hsa-miR-1185-2-3p | hsa-miR-6740-3p | hsa-miR-6797-5p | hsa-miR-6769b-3p |
| hsa-miR-1248 | hsa-miR-6748-3p | hsa-miR-6829-5p | hsa-miR-6775-3p |
| hsa-miR-1323 | hsa-miR-6796-3p | hsa-miR-6847-5p | hsa-miR-6801-5p |
| hsa-miR-150-3p | hsa-miR-6806-3p | hsa-miR-1306-5p | hsa-miR-6803-5p |
| hsa-miR-15a-5p | hsa-miR-6852-3p | hsa-miR-3143 | hsa-miR-6892-3p |
| hsa-miR-156-5p | hsa-miR-6868-3p | hsa-miR-3163 | hsa-miR-7109-5p |
| hsa-miR-16-5p | hsa-miR-7112-3p | hsa-miR-3185 | hsa-miR-7152-3p |
| hsa-miR-195-5p | hsa-miR-7159-3p | hsa-miR-335-3p | hsa-miR-7978 |
| hsa-miR-2196-5p | hsa-miR-7852-3p | hsa-miR-34b-3p | hsa-miR-8088 |
| hsa-miR-320e | hsa-miR-891a-3p | hsa-miR-3658 | hsa-miR-1273e |
| hsa-miR-3529-3p | hsa-miR-1199-5p | hsa-miR-3942-3p | hsa-miR-1277-5p |
| hsa-miR-3679-5p | hsa-miR-216b-3p | hsa-miR-4301 | hsa-miR-129-5p |
| hsa-miR-3688-3p | hsa-miR-4496 | hsa-miR-4423-5p | hsa-miR-145-5p |
| hsa-miR-3746-5p | hsa-miR-4676-5p | hsa-miR-4517 | hsa-miR-152-5p |
| hsa-miR-382-3p | hsa-miR-4755-3p | hsa-miR-4522 | hsa-miR-1587 |
| hsa-miR-3909 | hsa-miR-5691 | hsa-miR-4705 | hsa-miR-1825 |
| hsa-miR-3912-5p | hsa-miR-575 | hsa-miR-4722-3p | hsa-miR-1827 |
| hsa-miR-3928-5p | hsa-miR-596 | hsa-miR-4735-5p | hsa-miR-19a-3p |
| hsa-miR-3942-5p | hsa-miR-603 | hsa-miR-4766-5p | hsa-miR-19b-3p |
| hsa-miR-4421 | hsa-miR-6805-3p | hsa-miR-4775 | hsa-miR-2116-5p |
| hsa-miR-4491 | hsa-miR-7152-5p | hsa-miR-495-3p | hsa-miR-302c-5p |
| hsa-miR-4511 | hsa-miR-1305 | hsa-miR-5089-3p | hsa-miR-3121-3p |
| hsa-miR-4524b-3p | hsa-miR-134-3p | hsa-miR-511-5p | hsa-miR-32-3p |
| hsa-miR-4657 | hsa-miR-153-5p | hsa-miR-517-5p | hsa-miR-374a-5p |
| hsa-miR-496 | hsa-miR-214-5p | hsa-miR-548aj-3p | hsa-miR-409-3p |
| hsa-miR-4996-5p | hsa-miR-4486 | hsa-miR-5481 | hsa-miR-410-3p |
| hsa-miR-5093 | hsa-miR-4498 | hsa-miR-548x-3p | hsa-miR-4325 |
| hsa-miR-519d-5p | hsa-miR-4656 | hsa-miR-567 | hsa-miR-4520a-3p |
| hsa-miR-544a | hsa-miR-4674 | hsa-miR-580-3p | hsa-miR-4529-3p |
| hsa-miR-548al | hsa-miR-4797-5p | hsa-miR-630 | hsa-miR-4530 |
| hsa-miR-548aq-5p | hsa-miR-5001-5p | hsa-miR-6731-3p | hsa-miR-4696 |
| hsa-miR-559 | hsa-miR-5003-3p | hsa-miR-6828-3p | hsa-miR-4708-3p |

FIG. 16 B

| | | | |
|---|---|---|---|
| hsa-miR-590-3p | hsa-miR-510-3p | hsa-miR-6857-3p | hsa-miR-4720-3p |
| hsa-miR-6505-5p | hsa-miR-5589-5p | hsa-miR-6873-5p | hsa-miR-4743-3p |
| hsa-miR-6740-3p | hsa-miR-5787 | hsa-miR-767-3p | hsa-miR-4804-3p |
| hsa-miR-6748-3p | hsa-miR-579-3p | hsa-miR-8061 | hsa-miR-5190 |
| hsa-miR-6796-3p | hsa-miR-612 | hsa-miR-8075 | hsa-miR-550a-3p |
| hsa-miR-6806-3p | hsa-miR-622 | hsa-miR-129-1-3p | hsa-miR-552-5p |
| hsa-miR-6852-3p | hsa-miR-6514-3p | hsa-miR-129-2-3p | hsa-miR-577 |
| hsa-miR-6868-3p | hsa-miR-944 | hsa-miR-6131 | hsa-miR-6646-5p |
| hsa-miR-7112-3p | hsa-miR-96-3p | hsa-miR-6132 | hsa-miR-6765-5p |
| hsa-miR-7159-3p | hsa-miR-1066-5p | hsa-miR-6501-3p | hsa-miR-6834-3p |
| hsa-miR-7852-3p | hsa-miR-1252-5p | hsa-miR-6735-5p | hsa-miR-7703 |
| hsa-miR-891a-3p | hsa-miR-125a-3p | hsa-miR-6751-5p | hsa-miR-7705 |
| hsa-miR-1199-5p | hsa-miR-1288-5p | hsa-miR-6766-3p | hsa-miR-8070 |
| hsa-miR-216b-3p | hsa-miR-20a-5p | hsa-miR-6800-3p | hsa-miR-889-3p |
| hsa-miR-105-5p | hsa-miR-219a-5p | hsa-miR-6835-3p | hsa-miR-1200 |
| hsa-miR-122-3p | hsa-miR-296-3p | hsa-miR-6842-5p | hsa-miR-1225-3p |
| hsa-miR-1263 | hsa-miR-3147 | hsa-miR-6879-5p | hsa-miR-1228-5p |
| hsa-miR-142-5p | hsa-miR-3154 | hsa-miR-6881-3p | hsa-miR-1271-3p |
| hsa-miR-1468-3p | hsa-miR-3682-3p | hsa-miR-6889-5p | hsa-miR-1273a |
| hsa-miR-1911-3p | hsa-miR-372-3p | hsa-miR-7110-5p | hsa-miR-1273f |
| hsa-miR-21-5p | hsa-miR-374a-3p | hsa-miR-7111-3p | hsa-miR-1283 |
| hsa-miR-3123 | hsa-miR-376c-3p | hsa-miR-7973 | hsa-miR-1296-3p |
| hsa-miR-3125 | hsa-miR-4257 | hsa-miR-1178-3p | hsa-miR-1304-3p |
| hsa-miR-3145-3p | hsa-miR-4307 | hsa-miR-1250-3p | hsa-miR-130a-5p |
| hsa-miR-3149 | hsa-miR-4422 | hsa-miR-1292-5p | hsa-miR-1321 |
| hsa-miR-3184-3p | hsa-miR-4436b-3p | hsa-miR-1297 | hsa-miR-140-3p |
| hsa-miR-3606-3p | hsa-miR-4639-3p | hsa-miR-1301-3p | hsa-miR-145-3p |
| hsa-miR-3646 | hsa-miR-4677-3p | hsa-miR-1537-3p | hsa-miR-149-3p |
| hsa-miR-3662 | hsa-miR-4679 | hsa-miR-16-2-3p | hsa-miR-181a-5p |
| hsa-miR-379-5p | hsa-miR-4782-3p | hsa-miR-188-3p | hsa-miR-181b-5p |
| hsa-miR-4272 | hsa-miR-4786-3p | hsa-miR-188-5p | hsa-miR-181c-5p |
| hsa-miR-4282 | hsa-miR-4796-3p | hsa-miR-195-3p | hsa-miR-181d-5p |
| hsa-miR-4291 | hsa-miR-508-3p | hsa-miR-205-3p | hsa-miR-190a-5p |
| hsa-miR-433-5p | hsa-miR-519a-3p | hsa-miR-21-3p | hsa-miR-1906 |
| hsa-miR-4753-3p | hsa-miR-519b-3p | hsa-miR-224-5p | hsa-miR-1910-3p |
| hsa-miR-4768-3p | hsa-miR-519c-3p | hsa-miR-2467-3p | hsa-miR-203a |
| hsa-miR-4799-5p | hsa-miR-520a-3p | hsa-miR-25-3p | hsa-miR-216a-5p |
| hsa-miR-4802-3p | hsa-miR-5206 | hsa-miR-26a-5p | hsa-miR-296-5p |
| hsa-miR-498 | hsa-miR-520c-3p | hsa-miR-266-5p | hsa-miR-31-5p |
| hsa-miR-4999-5p | hsa-miR-520d-3p | hsa-miR-3142 | hsa-miR-3120-3p |

FIG. 16 C

| | | | |
|---|---|---|---|
| hsa-miR-520g-3p | hsa-miR-520e | hsa-miR-3145-Sp | hsa-miR-3120-Sp |
| hsa-miR-520h | hsa-miR-542-Sp | hsa-miR-3148 | hsa-miR-3135a |
| hsa-miR-548u | hsa-miR-548e-5p | hsa-miR-3156-3p | hsa-miR-31356 |
| hsa-miR-5579-3p | hsa-miR-548p | hsa-miR-3156-Sp | hsa-miR-3136-3p |
| hsa-miR-5590-3p | hsa-miR-5572 | hsa-miR-32-Sp | hsa-miR-3158-Sp |
| hsa-miR-56926 | hsa-miR-5696 | hsa-miR-3202 | hsa-miR-3165 |
| hsa-miR-5692c | hsa-miR-613 | hsa-miR-3612 | hsa-miR-3184-Sp |
| hsa-miR-617 | hsa-miR-5047 | hsa-miR-6824-Sp | hsa-miR-3188 |
| hsa-miR-6728-3p | hsa-miR-508-Sp | hsa-miR-6890-3p | hsa-miR-34a-5p |
| hsa-miR-6864-Sp | hsa-miR-5088-3p | hsa-miR-759 | hsa-miR-346-Sp |
| hsa-miR-7114-Sp | hsa-miR-513b-3p | hsa-miR-766-3p | hsa-miR-34c-5p |
| hsa-miR-7853-Sp | hsa-miR-5136-Sp | hsa-miR-888-Sp | hsa-miR-3667-Sp |
| hsa-miR-8082 | hsa-miR-518a-5p | hsa-miR-92a-3p | hsa-miR-3678-3p |
| hsa-miR-877-Sp | hsa-miR-5195-Sp | hsa-miR-92b-3p | hsa-miR-379-3p |
| hsa-miR-3619-Sp | hsa-miR-5196-Sp | hsa-miR-939-3p | hsa-miR-3908 |
| hsa-miR-36226-Sp | hsa-miR-527 | hsa-miR-1271-Sp | hsa-miR-3910 |
| hsa-miR-3670 | hsa-miR-545-3p | hsa-miR-128-2-Sp | hsa-miR-3929 |
| hsa-miR-3681-Sp | hsa-miR-548aj-5p | hsa-miR-1293 | hsa-miR-411-3p |
| hsa-miR-369-3p | hsa-miR-548ao-5p | hsa-miR-141-Sp | hsa-miR-423-Sp |
| hsa-miR-371a-5p | hsa-miR-548at-3p | hsa-miR-1914-3p | hsa-miR-4251 |
| hsa-miR-371b-5p | hsa-miR-548ax | hsa-miR-211-3p | hsa-miR-4270 |
| hsa-miR-373-Sp | hsa-miR-548ay-3p | hsa-miR-2861 | hsa-miR-4271 |
| hsa-miR-383-Sp | hsa-miR-548f-5p | hsa-miR-3921 | hsa-miR-4288 |
| hsa-miR-3916 | hsa-miR-548g-5p | hsa-miR-4264 | hsa-miR-4298 |
| hsa-miR-3922-Sp | hsa-miR-548x-5p | hsa-miR-4283 | hsa-miR-4303 |
| hsa-miR-3925-3p | hsa-miR-556-3p | hsa-miR-4297 | hsa-miR-44196 |
| hsa-miR-3972 | hsa-miR-5579-Sp | hsa-miR-4321 | hsa-miR-4430 |
| hsa-miR-424-Sp | hsa-miR-5692a | hsa-miR-4424 | hsa-miR-4433-3p |
| hsa-miR-4267 | hsa-miR-5695 | hsa-miR-4439 | hsa-miR-4441 |
| hsa-miR-4274 | hsa-miR-5703 | hsa-miR-4489 | hsa-miR-4459 |
| hsa-miR-4279 | hsa-miR-583 | hsa-miR-4492 | hsa-miR-4478 |
| hsa-miR-4292 | hsa-miR-584-Sp | hsa-miR-4653-Sp | hsa-miR-4481 |
| hsa-miR-4310 | hsa-miR-6089 | hsa-miR-4667-Sp | hsa-miR-449a |
| hsa-miR-4312 | hsa-miR-616-3p | hsa-miR-4675 | hsa-miR-449b-3p |
| hsa-miR-4317 | hsa-miR-616-Sp | hsa-miR-4693-3p | hsa-miR-4496-Sp |
| hsa-miR-4434 | hsa-miR-623 | hsa-miR-4709-3p | hsa-miR-449c-5p |
| hsa-miR-4438 | hsa-miR-634 | hsa-miR-4745-Sp | hsa-miR-4503 |
| hsa-miR-4451 | hsa-miR-650 | hsa-miR-4746-3p | hsa-miR-4505 |
| hsa-miR-4460 | hsa-miR-651-Sp | hsa-miR-512-Sp | hsa-miR-4513 |
| hsa-miR-4471 | hsa-miR-656-3p | hsa-miR-558 | hsa-miR-4516 |

FIG. 16 D

| | | | |
|---|---|---|---|
| hsa-miR-4488 | hsa-miR-6715a-3p | hsa-miR-5584-Sp | hsa-miR-4534 |
| hsa-miR-4514 | hsa-miR-67156-Sp | hsa-miR-593-3p | hsa-miR-4536-Sp |
| hsa-miR-4519 | hsa-miR-6771-3p | hsa-miR-6076 | hsa-miR-4537 |
| hsa-miR-4533 | hsa-miR-6782-Sp | hsa-miR-637 | hsa-miR-4649-Sp |
| hsa-miR-455-3p | hsa-miR-6789-Sp | hsa-miR-654-3p | hsa-miR-4683 |
| hsa-miR-4697-Sp | hsa-miR-6791-Sp | hsa-miR-6741-Sp | hsa-miR-4685-Sp |
| hsa-miR-4716-3p | hsa-miR-6801-3p | hsa-miR-6745 | hsa-miR-4695-Sp |
| hsa-miR-4719 | hsa-miR-4713-3p | hsa-miR-26b-3p | hsa-miR-4723-Sp |
| hsa-miR-4727-3p | hsa-miR-4726-3p | hsa-miR-27a-3p | hsa-miR-4725-Sp |
| hsa-miR-4747-5p | hsa-miR-4757-Sp | hsa-miR-27b-3p | hsa-miR-4733-Sp |
| hsa-miR-4753-Sp | hsa-miR-4778-3p | hsa-miR-299-Sp | hsa-miR-4736 |
| hsa-miR-4803 | hsa-miR-4784 | hsa-miR-29a-5p | hsa-miR-4742-3p |
| hsa-miR-497-3p | hsa-miR-5000-Sp | hsa-miR-3065-Sp | hsa-miR-4756-Sp |
| hsa-miR-497-Sp | hsa-miR-5189-Sp | hsa-miR-3129-3p | hsa-miR-4763-3p |
| hsa-miR-6750-Sp | hsa-miR-598-Sp | hsa-miR-3153 | hsa-miR-4786-Sp |
| hsa-miR-6776-Sp | hsa-miR-670-Sp | hsa-miR-3173-Sp | hsa-miR-4795-Sp |
| hsa-miR-6786-Sp | hsa-miR-6724-Sp | hsa-miR-3180-Sp | hsa-miR-491-Sp |
| hsa-miR-6788-3p | hsa-miR-6746-Sp | hsa-miR-3187-Sp | hsa-miR-5004-Sp |
| hsa-miR-6809-3p | hsa-miR-6756-Sp | hsa-miR-323a-5p | hsa-miR-504-Sp |
| hsa-miR-6822-Sp | hsa-miR-6764-Sp | hsa-miR-338-Sp | hsa-miR-510-5p |
| hsa-miR-6848-3p | hsa-miR-6810-3p | hsa-miR-346 | hsa-miR-513c-5p |
| hsa-miR-6895-3p | hsa-miR-6823-Sp | hsa-miR-3617-Sp | hsa-miR-5146-Sp |
| hsa-miR-762 | hsa-miR-6826-3p | hsa-miR-3691-3p | hsa-miR-5446 |
| hsa-miR-765 | hsa-miR-6846-Sp | hsa-miR-377-3p | hsa-miR-548c-3p |
| hsa-miR-8077 | hsa-miR-6848-Sp | hsa-miR-378g | hsa-miR-548m |
| hsa-miR-942-Sp | hsa-miR-6858-Sp | hsa-miR-3920 | hsa-miR-550a-3-5p |
| hsa-miR-1180-Sp | hsa-miR-7155-Sp | hsa-miR-4268 | hsa-miR-550a-5p |
| hsa-miR-1193 | hsa-miR-7161-Sp | hsa-miR-4448 | hsa-miR-5581-Sp |
| hsa-miR-1208 | hsa-miR-8057 | hsa-miR-4512 | hsa-miR-5586-3p |
| hsa-miR-1224-Sp | hsa-miR-8071 | hsa-miR-4518 | hsa-miR-563 |
| hsa-miR-1275 | hsa-miR-875-3p | hsa-miR-4524a-5p | hsa-miR-5698 |
| hsa-miR-1285-3p | hsa-miR-892a | hsa-miR-45246-Sp | hsa-miR-607 |
| hsa-miR-181b-3p | hsa-miR-92a-2-5p | hsa-miR-4660 | hsa-miR-6077 |
| hsa-miR-2114-Sp | hsa-miR-1207-Sp | hsa-miR-4667-3p | hsa-miR-6080 |
| hsa-miR-3026-Sp | hsa-miR-1255a | hsa-miR-4668-Sp | hsa-miR-6086 |
| hsa-miR-302d-5p | hsa-miR-1266-Sp | hsa-miR-4673 | hsa-miR-6134 |
| hsa-miR-3150b-3p | hsa-miR-128-3p | hsa-miR-4698 | hsa-miR-620 |
| hsa-miR-3151-Sp | hsa-miR-1343-3p | hsa-miR-4726-Sp | hsa-miR-649 |
| hsa-miR-3170 | hsa-miR-143-3p | hsa-miR-4735-3p | hsa-miR-6500-3p |
| hsa-miR-3927-3p | hsa-miR-146b-3p | hsa-miR-4770 | hsa-miR-6515-Sp |

FIG. 16 E

| | | | |
|---|---|---|---|
| hsa-miR-4287 | hsa-miR-183-5p | hsa-miR-484 | hsa-miR-657 |
| hsa-miR-4316 | hsa-miR-192-3p | hsa-miR-513a-5p | hsa-miR-668-3p |
| hsa-miR-4318 | hsa-miR-1976 | hsa-miR-541-5p | hsa-miR-671-5p |
| hsa-miR-4432 | hsa-miR-2115-5p | hsa-miR-551b-5p | hsa-miR-6721-5p |
| hsa-miR-4433b-3p | hsa-miR-216a-3p | hsa-miR-5583-5p | hsa-miR-6727-3p |
| hsa-miR-4447 | hsa-miR-219a-1-3p | hsa-miR-569 | hsa-miR-6729-5p |
| hsa-miR-4472 | hsa-miR-24-3p | hsa-miR-5700 | hsa-miR-6730-5p |
| hsa-miR-4638-3p | hsa-miR-6744-5p | hsa-miR-4773 | hsa-miR-7515 |
| hsa-miR-4641 | hsa-miR-6752-5p | hsa-miR-548ah-5p | hsa-miR-7845-5p |
| hsa-miR-4645-3p | hsa-miR-6760-5p | hsa-miR-592 | hsa-miR-8087 |
| hsa-miR-4664-5p | hsa-miR-6776-3p | hsa-miR-605-5p | hsa-miR-122-5p |
| hsa-miR-4685-3p | hsa-miR-6780a-5p | hsa-miR-6876-5p | hsa-miR-1226-5p |
| hsa-miR-4700-5p | hsa-miR-6787-5p | hsa-miR-1253 | hsa-miR-1245a |
| hsa-miR-4710 | hsa-miR-6791-3p | hsa-miR-125a-5p | hsa-miR-1294 |
| hsa-miR-641 | hsa-miR-6792-3p | hsa-miR-125b-5p | hsa-miR-1295b-5p |
| hsa-miR-647 | hsa-miR-6792-5p | hsa-miR-214-3p | hsa-miR-1306-5p |
| hsa-miR-653-3p | hsa-miR-6813-3p | hsa-miR-2355-5p | hsa-miR-146a-5p |
| hsa-miR-6636 | hsa-miR-6829-3p | hsa-miR-3121-5p | hsa-miR-146b-5p |
| hsa-miR-6799-3p | hsa-miR-6837-3p | hsa-miR-3144-5p | hsa-miR-17-3p |
| hsa-miR-6860 | hsa-miR-6840-3p | hsa-miR-3152-3p | hsa-miR-17-5p |
| hsa-miR-6895-5p | hsa-miR-6843-3p | hsa-miR-3179 | hsa-miR-192-5p |
| hsa-miR-7113-5p | hsa-miR-6849-3p | hsa-miR-329-3p | hsa-miR-204-3p |
| hsa-miR-7151-5p | hsa-miR-6853-5p | hsa-miR-362-3p | hsa-miR-208b-5p |
| hsa-miR-7160-3p | hsa-miR-6855-3p | hsa-miR-3667-3p | hsa-miR-20b-5p |
| hsa-miR-7160-5p | hsa-miR-6858-3p | hsa-miR-3671 | hsa-miR-2110 |
| hsa-miR-7976 | hsa-miR-6870-5p | hsa-miR-3919 | hsa-miR-2116-3p |
| hsa-miR-8063 | hsa-miR-6875-3p | hsa-miR-3925-5p | hsa-miR-212-5p |
| hsa-miR-95-5p | hsa-miR-6878-5p | hsa-miR-3934-5p | hsa-miR-23b-5p |
| hsa-miR-1237-3p | hsa-miR-6883-5p | hsa-miR-425-5p | hsa-miR-3140-3p |
| hsa-miR-1254 | hsa-miR-6888-5p | hsa-miR-4284 | hsa-miR-3150a-3p |
| hsa-miR-143-5p | hsa-miR-6894-5p | hsa-miR-4319 | hsa-miR-3155a |
| hsa-miR-154-5p | hsa-miR-7111-5p | hsa-miR-4445-3p | hsa-miR-3155b |
| hsa-miR-1915-3p | hsa-miR-7154-5p | hsa-miR-4531 | hsa-miR-3186-5p |
| hsa-miR-30a-5p | hsa-miR-7155-3p | hsa-miR-4535 | hsa-miR-3187-3p |
| hsa-miR-30b-5p | hsa-miR-7156-3p | hsa-miR-4652-5p | hsa-miR-345-5p |
| hsa-miR-30c-5p | hsa-miR-7851-3p | hsa-miR-4716-5p | hsa-miR-3609 |
| hsa-miR-30d-5p | hsa-miR-8081 | hsa-miR-4776-5p | hsa-miR-3663-5p |
| hsa-miR-30e-5p | hsa-miR-873-3p | hsa-miR-4800-5p | hsa-miR-3677-5p |
| hsa-miR-3177-3p | hsa-miR-873-5p | hsa-miR-4802-5p | hsa-miR-3688-5p |
| hsa-miR-3591-3p | hsa-miR-887-5p | hsa-miR-511-3p | hsa-miR-378a-5p |

FIG. 16 F

| | | | |
|---|---|---|---|
| hsa-miR-3620-3p | hsa-miR-106a-5p | hsa-miR-5699-3p | hsa-miR-3911 |
| hsa-miR-4469 | hsa-miR-3200-3p | hsa-miR-5739 | hsa-miR-3937 |
| hsa-miR-4483 | hsa-miR-3657 | hsa-miR-6514-Sp | hsa-miR-411-Sp |
| hsa-miR-4497 | hsa-miR-4476 | hsa-miR-6759-3p | hsa-miR-4255 |
| hsa-miR-4633-3p | hsa-miR-452-Sp | hsa-miR-6768-Sp | hsa-miR-4293 |
| hsa-miR-4645-Sp | hsa-miR-4669 | hsa-miR-6783-Sp | hsa-miR-4309 |
| hsa-miR-4665-Sp | hsa-miR-4715-Sp | hsa-miR-6859-Sp | hsa-miR-4326 |
| hsa-miR-4723-3p | hsa-miR-4330 | hsa-let-7g-5p | hsa-miR-7162-Sp |
| hsa-miR-4793-3p | hsa-miR-4418 | hsa-let-7i-5p | hsa-miR-9-3p |
| hsa-miR-514a-5p | hsa-miR-4464 | hsa-miR-1255b-2-3p | hsa-miR-98-Sp |
| hsa-miR-6426-Sp | hsa-miR-4465 | hsa-miR-126-Sp | hsa-miR-101-3p |
| hsa-miR-6500-Sp | hsa-miR-4470 | hsa-miR-1260a | hsa-miR-1226-3p |
| hsa-miR-6503-Sp | hsa-miR-4480 | hsa-miR-12606 | hsa-miR-144-3p |
| hsa-miR-6753-Sp | hsa-miR-4640-Sp | hsa-miR-1279 | hsa-miR-186-Sp |
| hsa-miR-645 | hsa-miR-4701-Sp | hsa-miR-300 | hsa-miR-2392 |
| hsa-miR-646 | hsa-miR-4708-Sp | hsa-miR-323a-3p | hsa-miR-297 |
| hsa-miR-6503-3p | hsa-miR-4720-Sp | hsa-miR-3529-Sp | hsa-miR-30la-5p |
| hsa-miR-6505-3p | hsa-miR-4725-3p | hsa-miR-3613-3p | hsa-miR-302a-5p |
| hsa-miR-6508-3p | hsa-miR-4728-3p | hsa-miR-3653 | hsa-miR-3167 |
| hsa-miR-6513-3p | hsa-miR-4731-Sp | hsa-miR-380-3p | hsa-miR-3194-3p |
| hsa-miR-6516-3p | hsa-miR-4750-3p | hsa-miR-381-3p | hsa-miR-3680-3p |
| hsa-miR-660-3p | hsa-miR-5006-Sp | hsa-miR-383-3p | hsa-miR-3689d |
| hsa-miR-6736-3p | hsa-miR-5095 | hsa-miR-3913-Sp | hsa-miR-421 |
| hsa-miR-6741-3p | hsa-miR-512-3p | hsa-miR-3924 | hsa-miR-4286 |
| hsa-miR-6747-3p | hsa-miR-518d-5p | hsa-miR-4294 | hsa-miR-4506-Sp |
| hsa-miR-6763-Sp | hsa-miR-518e-5p | hsa-miR-4500 | hsa-miR-4659a-3p |
| hsa-miR-67806-Sp | hsa-miR-518f-5p | hsa-miR-4501 | hsa-miR-4659b-3p |
| hsa-miR-6781-3p | hsa-miR-5194 | hsa-miR-4650-3p | hsa-miR-4700-3p |
| hsa-miR-6783-3p | hsa-miR-519a-5p | hsa-miR-4704-3p | hsa-miR-4709-Sp |
| hsa-miR-6787-3p | hsa-miR-5196-Sp | hsa-miR-4739 | hsa-miR-4728-Sp |
| hsa-miR-6807-3p | hsa-miR-519c-5p | hsa-miR-4789-Sp | hsa-miR-4752 |
| hsa-miR-6807-Sp | hsa-miR-519d-3p | hsa-miR-485-3p | hsa-miR-4764-Sp |
| hsa-miR-6812-Sp | hsa-miR-520c-5p | hsa-miR-490-Sp | hsa-miR-4779 |
| hsa-miR-6821-3p | hsa-miR-520f-3p | hsa-miR-5002-Sp | hsa-miR-4789-3p |
| hsa-miR-6832-Sp | hsa-miR-520g-5p | hsa-miR-5007-3p | hsa-miR-4795-3p |
| hsa-miR-6834-Sp | hsa-miR-522-Sp | hsa-miR-516a-3p | hsa-miR-4797-3p |
| hsa-miR-6857-Sp | hsa-miR-523-Sp | hsa-miR-516b-3p | hsa-miR-499a-3p |
| hsa-miR-6877-3p | hsa-miR-526a | hsa-miR-548aa | hsa-miR-499b-3p |
| hsa-miR-6879-3p | hsa-miR-532-3p | hsa-miR-548ap-3p | hsa-miR-5011-5p |
| hsa-miR-6887-3p | hsa-miR-5693 | hsa-miR-548t-3p | hsa-miR-507 |

FIG. 16 G

| | | | |
|---|---|---|---|
| hsa-miR-7151-3p | hsa-miR-588 | hsa-miR-5681a | hsa-miR-5096 |
| hsa-miR-7153-5p | hsa-miR-589-3p | hsa-miR-584-3p | hsa-miR-548ac |
| hsa-miR-769-3p | hsa-miR-589-5p | hsa-miR-6081 | hsa-miR-548ae |
| hsa-miR-8089 | hsa-miR-6088 | hsa-miR-6513-5p | hsa-miR-548ah-3p |
| hsa-miR-93-3p | hsa-miR-6125 | hsa-miR-6761-5p | hsa-miR-548am-3p |
| hsa-miR-93-5p | hsa-miR-619-5p | hsa-miR-6854-5p | hsa-miR-548aq-3p |
| hsa-miR-99a-3p | hsa-miR-628-5p | hsa-miR-7-5p | hsa-miR-548d-3p |
| hsa-miR-99b-3p | hsa-miR-4306 | hsa-miR-4693-5p | hsa-miR-4732-3p |
| hsa-miR-6766-5p | hsa-miR-4323 | hsa-miR-4711-5p | hsa-miR-4765 |
| hsa-let-7a-5p | hsa-miR-4327 | hsa-miR-539-3p | hsa-miR-4768-5p |
| hsa-let-7b-5p | hsa-miR-433-3p | hsa-miR-561-5p | hsa-miR-4780 |
| hsa-let-7c-5p | hsa-miR-4423-3p | hsa-miR-5707 | hsa-miR-4782-5p |
| hsa-let-7e-5p | hsa-miR-4445-5p | hsa-miR-586 | hsa-miR-4791 |
| hsa-let-7f-5p | hsa-miR-4644 | hsa-miR-6885-3p | hsa-miR-483-3p |
| hsa-miR-548h-3p | hsa-miR-4712-3p | hsa-miR-7110-3p | hsa-miR-489-3p |
| hsa-miR-548j-3p | hsa-miR-4712-5p | hsa-miR-10b-3p | hsa-miR-491-3p |
| hsa-miR-548z | hsa-miR-4761-5p | hsa-miR-1185-5p | hsa-miR-5010-5p |
| hsa-miR-600 | hsa-miR-5006-3p | hsa-miR-1233-3p | hsa-miR-5011-3p |
| hsa-miR-6124 | hsa-miR-5192 | hsa-miR-1236-5p | hsa-miR-514a-3p |
| hsa-miR-640 | hsa-miR-5197-3p | hsa-miR-1256 | hsa-miR-514b-3p |
| hsa-miR-665 | hsa-miR-5590-5p | hsa-miR-1262 | hsa-miR-5186 |
| hsa-miR-6742-3p | hsa-miR-578 | hsa-miR-1270 | hsa-miR-548a-3p |
| hsa-miR-676-5p | hsa-miR-581 | hsa-miR-1291 | hsa-miR-548o-3p |
| hsa-miR-6785-5p | hsa-miR-6504-3p | hsa-miR-1299 | hsa-miR-556-5p |
| hsa-miR-6799-5p | hsa-miR-6507-3p | hsa-miR-137 | hsa-miR-5683 |
| hsa-miR-6847-3p | hsa-miR-6511a-5p | hsa-miR-16-1-3p | hsa-miR-5685 |
| hsa-miR-6871-5p | hsa-miR-659-3p | hsa-miR-2054 | hsa-miR-5706 |
| hsa-miR-7106-5p | hsa-miR-671-3p | hsa-miR-208a-5p | hsa-miR-618 |
| hsa-miR-7159-5p | hsa-miR-6730-3p | hsa-miR-3074-5p | hsa-miR-619-3p |
| hsa-miR-7856-5p | hsa-miR-6733-5p | hsa-miR-328-3p | hsa-miR-624-3p |
| hsa-miR-802 | hsa-miR-6739-5p | hsa-miR-340-5p | hsa-miR-625-5p |
| hsa-miR-8064 | hsa-miR-6754-3p | hsa-miR-345-3p | hsa-miR-6515-3p |
| hsa-miR-92a-1-5p | hsa-miR-6756-3p | hsa-miR-3607-3p | hsa-miR-6737-3p |
| hsa-miR-1233-5p | hsa-miR-6758-3p | hsa-miR-3661 | hsa-miR-6739-3p |
| hsa-miR-1266-3p | hsa-miR-6778-5p | hsa-miR-3663-3p | hsa-miR-6782-3p |
| hsa-miR-153-3p | hsa-miR-6802-5p | hsa-miR-4277 | hsa-miR-6794-3p |
| hsa-miR-185-5p | hsa-miR-6815-3p | hsa-miR-4324 | hsa-miR-6794-5p |
| hsa-miR-18a-5p | hsa-miR-8083 | hsa-miR-4427 | hsa-miR-6830-3p |
| hsa-miR-186-5p | hsa-miR-3714 | hsa-miR-4456 | hsa-miR-6839-5p |
| hsa-miR-194-3p | hsa-miR-4493 | hsa-miR-4461 | hsa-miR-6846-3p |

FIG. 16 H

| | | | |
|---|---|---|---|
| hsa-miR-197-3p | hsa-miR-5189-3p | hsa-miR-4482-3p | hsa-miR-6851-3p |
| hsa-miR-2115-3p | hsa-miR-5266-Sp | hsa-miR-4495 | hsa-miR-6859-3p |
| hsa-miR-221-3p | hsa-miR-548q | hsa-miR-4521 | hsa-miR-6867-3p |
| hsa-miR-28-Sp | hsa-miR-564 | hsa-miR-4663 | hsa-miR-6874-Sp |
| hsa-miR-3065-3p | hsa-miR-5688 | hsa-miR-4670-3p | hsa-miR-6889-3p |
| hsa-miR-30a-3p | hsa-miR-574-3p | hsa-miR-4680-3p | hsa-miR-7-1-3p |
| hsa-miR-30d-3p | hsa-miR-605-3p | hsa-miR-4701-3p | hsa-miR-7-2-3p |
| hsa-miR-30e-3p | hsa-miR-7157-3p | hsa-miR-6841-Sp | hsa-miR-6734-3p |
| hsa-miR-3161 | hsa-miR-100-3p | hsa-miR-6866-Sp | hsa-miR-6736-Sp |
| hsa-miR-3182 | hsa-miR-1238-3p | hsa-miR-6867-Sp | hsa-miR-6759-Sp |
| hsa-miR-34a-3p | hsa-miR-1238-Sp | hsa-miR-6878-3p | hsa-miR-6793-Sp |
| hsa-miR-3668 | hsa-miR-1272 | hsa-miR-8080 | hsa-miR-6817-3p |
| hsa-miR-3926 | hsa-miR-1303 | hsa-miR-877-3p | hsa-miR-6862-3p |
| hsa-miR-4256 | hsa-miR-1322 | hsa-miR-1179 | hsa-miR-6864-3p |
| hsa-miR-1257 | hsa-miR-135b-3p | hsa-miR-1207-3p | hsa-miR-6873-3p |
| hsa-miR-181a-2-3p | hsa-miR-1911-Sp | hsa-miR-18b-3p | hsa-miR-6874-3p |
| hsa-miR-331-Sp | hsa-miR-210-5p | hsa-miR-223-Sp | hsa-miR-6882-3p |
| hsa-miR-3606-Sp | hsa-miR-215-Sp | hsa-miR-3160-Sp | hsa-miR-6884-Sp |
| hsa-miR-376a-3p | hsa-miR-2681-Sp | hsa-miR-3607-Sp | hsa-miR-7974 |
| hsa-miR-376b-3p | hsa-miR-276-Sp | hsa-miR-367-Sp | hsa-miR-892c-5p |
| hsa-miR-3927-Sp | hsa-miR-3190-3p | hsa-miR-3679-3p | hsa-miR-6870-3p |
| hsa-miR-4311 | hsa-miR-330-3p | hsa-miR-374b-3p | hsa-miR-1236-3p |
| hsa-miR-4419a | hsa-miR-331-3p | hsa-miR-3936 | hsa-miR-1914-Sp |
| hsa-miR-4507 | hsa-miR-335-Sp | hsa-miR-4254 | hsa-miR-3613-Sp |
| hsa-miR-450a-1-3p | hsa-miR-33a-5p | hsa-miR-4320 | hsa-miR-5008-3p |
| hsa-miR-4510 | hsa-miR-336-Sp | hsa-miR-4446-Sp | hsa-miR-505-Sp |
| hsa-miR-455-Sp | hsa-miR-3659 | hsa-miR-451b | hsa-miR-6819-3p |
| hsa-miR-4642 | hsa-miR-4515 | hsa-miR-4524a-3p | hsa-let-7c-3p |
| hsa-miR-4662a-5p | hsa-miR-4658 | hsa-miR-4526 | hsa-miR-1178-Sp |
| hsa-miR-4686 | hsa-miR-4684-3p | hsa-miR-4529-Sp | hsa-miR-1273g-3p |
| hsa-miR-4762-Sp | hsa-miR-4740-Sp | hsa-miR-4649-3p | hsa-miR-2166-Sp |
| hsa-miR-5010-3p | hsa-miR-4758-Sp | hsa-miR-4714-Sp | hsa-miR-3157-Sp |
| hsa-miR-502-Sp | hsa-miR-548at-5p | hsa-miR-4721 | hsa-miR-3162-Sp |
| hsa-miR-5506-2-Sp | hsa-miR-5582-Sp | hsa-miR-4755-Sp | hsa-miR-361-Sp |
| hsa-miR-5697 | hsa-miR-568 | hsa-miR-485-Sp | hsa-miR-3651 |
| hsa-miR-6127 | hsa-miR-5701 | hsa-miR-493-Sp | hsa-miR-4261 |
| hsa-miR-6129 | hsa-miR-573 | hsa-miR-5100 | hsa-miR-4646-3p |
| hsa-miR-6130 | hsa-miR-574-Sp | hsa-miR-515-Sp | hsa-miR-4724-3p |
| hsa-miR-6133 | hsa-miR-6128 | hsa-miR-5193 | hsa-miR-4769-3p |
| hsa-miR-6734-Sp | hsa-miR-644a | hsa-miR-519e-5p | hsa-miR-4777-Sp |

FIG. 16 I

| | | | |
|---|---|---|---|
| hsa-miR-6751-3p | hsa-miR-6755-Sp | hsa-miR-5571-Sp | hsa-miR-5197-Sp |
| hsa-miR-891b | hsa-miR-6758-Sp | hsa-miR-5682 | hsa-miR-532-Sp |
| hsa-miR-1183 | hsa-miR-6790-Sp | hsa-miR-6071 | hsa-miR-543 |
| hsa-miR-142-3p | hsa-miR-6816-3p | hsa-miR-627-3p | hsa-miR-545-Sp |
| hsa-miR-1537-Sp | hsa-miR-6818-Sp | hsa-miR-636 | hsa-miR-6817-Sp |
| hsa-miR-198 | hsa-miR-6826-Sp | hsa-miR-651-3p | hsa-miR-6886-Sp |
| hsa-miR-20b-3p | hsa-miR-6833-Sp | hsa-miR-664a-3p | hsa-miR-7157-Sp |
| hsa-miR-22-3p | hsa-miR-7849-3p | hsa-miR-8058 | hsa-miR-655-Sp |
| hsa-miR-374c-5p | hsa-miR-1267 | hsa-miR-8085 | hsa-miR-675-3p |
| hsa-miR-382-Sp | hsa-miR-1273h-5p | hsa-miR-1290 | hsa-miR-6753-3p |
| hsa-miR-3976 | hsa-miR-147a | hsa-miR-1304-Sp | hsa-miR-6833-3p |
| hsa-miR-4328 | hsa-miR-1972 | hsa-miR-149-Sp | hsa-miR-6856-Sp |
| hsa-miR-4437 | hsa-miR-30b-3p | hsa-miR-182-Sp | hsa-miR-6881-Sp |
| hsa-miR-4455 | hsa-miR-30c-1-3p | hsa-miR-2053 | hsa-miR-6888-3p |
| hsa-miR-4691-Sp | hsa-miR-30c-2-3p | hsa-miR-2117 | hsa-miR-7107-3p |
| hsa-miR-4759 | hsa-miR-3160-3p | hsa-miR-3064-Sp | hsa-miR-744-3p |
| hsa-miR-4762-3p | hsa-miR-3186-3p | hsa-miR-31-3p | hsa-miR-7843-3p |
| hsa-miR-5002-3p | hsa-miR-329-Sp | hsa-miR-3189-Sp | hsa-miR-7855-Sp |
| hsa-miR-5004-3p | hsa-miR-3665 | hsa-miR-3191-Sp | hsa-miR-876-Sp |
| hsa-miR-5008-Sp | hsa-miR-3677-3p | hsa-miR-337-3p | hsa-miR-96-Sp |
| hsa-miR-5009-3p | hsa-miR-3689a-3p | hsa-miR-338-3p | hsa-miR-103a-3p |
| hsa-miR-5087 | hsa-miR-3689b-3p | hsa-miR-34c-3p | hsa-miR-107 |
| hsa-miR-553 | hsa-miR-3689c | hsa-miR-3675-3p | hsa-miR-1225-Sp |
| hsa-miR-557 | hsa-miR-4252 | hsa-miR-377-Sp | hsa-miR-1229-3p |
| hsa-miR-639 | hsa-miR-432-Sp | hsa-miR-378j | hsa-miR-1229-Sp |
| hsa-miR-655-3p | hsa-miR-4487 | hsa-miR-3915 | hsa-miR-1269a |
| hsa-miR-6798-Sp | hsa-miR-4504 | hsa-miR-3928-3p | hsa-miR-12696 |
| hsa-miR-6804-Sp | hsa-miR-4525 | hsa-miR-4273 | hsa-miR-1273d |
| hsa-miR-6818-3p | hsa-miR-548ad | hsa-miR-452-3p | hsa-miR-128-1-Sp |
| hsa-miR-6830-Sp | hsa-miR-642a-5p | hsa-miR-4527 | hsa-miR-1288-3p |
| hsa-miR-6831-3p | hsa-miR-6511a-3p | hsa-miR-4652-3p | hsa-miR-187-Sp |
| hsa-miR-6884-3p | hsa-miR-6511b-3p | hsa-miR-4662a-3p | hsa-miR-1910-5p |
| hsa-miR-7153-3p | hsa-miR-670-3p | hsa-miR-4687-3p | hsa-miR-22-Sp |
| hsa-miR-766-Sp | hsa-miR-6729-3p | hsa-miR-4689 | hsa-miR-3132 |
| hsa-miR-1197 | hsa-miR-6731-Sp | hsa-miR-4703-3p | hsa-miR-3158-3p |
| hsa-miR-1276 | hsa-miR-6737-Sp | hsa-miR-4758-3p | hsa-miR-3183 |
| hsa-miR-2682-3p | hsa-miR-6749-3p | hsa-miR-4760-Sp | hsa-miR-3192-Sp |
| hsa-miR-3117-3p | hsa-miR-6764-3p | hsa-miR-4794 | hsa-miR-3200-Sp |
| hsa-miR-3617-3p | hsa-miR-6773-3p | hsa-miR-539-Sp | hsa-miR-326 |
| hsa-miR-3655 | hsa-miR-6779-Sp | hsa-miR-5680 | hsa-miR-330-Sp |

FIG. 16 J

| | | | |
|---|---|---|---|
| hsa-miR-4308 | hsa-miR-6780b-3p | hsa-miR-5699-Sp | hsa-miR-339-Sp |
| hsa-miR-4635 | hsa-miR-6788-Sp | hsa-miR-590-Sp | hsa-miR-342-3p |
| hsa-miR-4678 | hsa-miR-6813-Sp | hsa-miR-6083 | hsa-miR-3620-Sp |
| hsa-miR-4692 | hsa-miR-6819-Sp | hsa-miR-625-3p | hsa-miR-3680-Sp |
| hsa-miR-4731-3p | hsa-miR-6824-3p | hsa-miR-6499-3p | hsa-miR-374c-3p |
| hsa-miR-4742-Sp | hsa-miR-6845-3p | hsa-miR-6504-Sp | hsa-miR-4265 |
| hsa-miR-4756-3p | hsa-miR-6845-3p | hsa-miR-6516-Sp | hsa-miR-4314 |
| hsa-miR-4771 | hsa-miR-4322 | hsa-miR-501-3p | hsa-miR-3126-3p |
| hsa-miR-548az-3p | hsa-miR-4482-Sp | hsa-miR-502-3p | hsa-miR-3173-3p |
| hsa-miR-548e-3p | hsa-miR-4502 | hsa-miR-509-3p | hsa-miR-3189-3p |
| hsa-miR-548f-3p | hsa-miR-4639-Sp | hsa-miR-6126 | hsa-miR-3201 |
| hsa-miR-549a | hsa-miR-4648 | hsa-miR-6735-3p | hsa-miR-3614-Sp |
| hsa-miR-609 | hsa-miR-4651 | hsa-miR-6808-3p | hsa-miR-370-Sp |
| hsa-miR-629-Sp | hsa-miR-4654 | hsa-miR-874-3p | hsa-miR-4269 |
| hsa-miR-6838-Sp | hsa-miR-4694-3p | hsa-miR-136-3p | hsa-miR-4452 |
| hsa-miR-6882-Sp | hsa-miR-4695-3p | hsa-miR-3159 | hsa-miR-4463 |
| hsa-miR-7854-3p | hsa-miR-4729 | hsa-miR-3191-3p | hsa-miR-449c-3p |
| hsa-miR-1261 | hsa-miR-4754 | hsa-miR-3605-Sp | hsa-miR-4666a-5p |
| hsa-miR-133a-3p | hsa-miR-4792 | hsa-miR-3650 | hsa-miR-4747-3p |
| hsa-miR-1336 | hsa-miR-5090 | hsa-miR-3654 | hsa-miR-4751 |
| hsa-miR-184 | hsa-miR-513a-3p | hsa-miR-3941 | hsa-miR-4760-3p |
| hsa-miR-190a-3p | hsa-miR-513c-3p | hsa-miR-4420 | hsa-miR-4772-3p |
| hsa-miR-204-Sp | hsa-miR-518c-5p | hsa-miR-466 | hsa-miR-5166-Sp |
| hsa-miR-211-Sp | hsa-miR-5702 | hsa-miR-4672 | hsa-miR-5588-3p |
| hsa-miR-2113 | hsa-miR-6073 | hsa-miR-4717-3p | hsa-miR-632 |
| hsa-miR-3134 | hsa-miR-627-Sp | hsa-miR-4793-Sp | hsa-miR-643 |
| hsa-miR-3611 | hsa-miR-6719-3p | hsa-miR-4799-3p | hsa-miR-656-Sp |
| hsa-miR-384 | hsa-miR-6742-Sp | hsa-miR-520a-5p | hsa-miR-6754-Sp |
| hsa-miR-4426 | hsa-miR-6762-Sp | hsa-miR-525-Sp | hsa-miR-6784-3p |
| hsa-miR-4647 | hsa-miR-6793-3p | hsa-miR-5588-Sp | hsa-miR-6811-Sp |
| hsa-miR-5187-3p | hsa-miR-6796-Sp | hsa-miR-595 | hsa-miR-6837-Sp |
| hsa-miR-548a-5p | hsa-miR-6828-Sp | hsa-miR-6079 | hsa-miR-6885-Sp |
| hsa-miR-548ab | hsa-miR-6845-Sp | hsa-miR-6772-3p | hsa-miR-6892-Sp |
| hsa-miR-548ak | hsa-miR-6869-Sp | hsa-miR-6868-Sp | hsa-miR-708-Sp |
| hsa-miR-548am-5p | hsa-miR-7113-3p | hsa-miR-8926 | hsa-miR-885-Sp |
| hsa-miR-548ap-5p | hsa-miR-8067 | hsa-miR-1343-Sp | hsa-miR-3127-Sp |
| hsa-miR-548ar-5p | hsa-miR-889-Sp | hsa-miR-3197 | hsa-miR-3192-3p |
| hsa-miR-548as-5p | hsa-miR-937-Sp | hsa-miR-597-3p | hsa-miR-3664-Sp |
| hsa-miR-548au-5p | hsa-miR-1252-3p | hsa-miR-6772-Sp | hsa-miR-4643 |
| hsa-miR-548av-5p | hsa-miR-1258 | hsa-miR-6825-Sp | hsa-miR-4668-3p |

FIG. 16 K

| | | | |
|---|---|---|---|
| hsa-miR-548ay-5p | hsa-miR-140-5p | hsa-miR-939-5p | hsa-miR-4676-3p |
| hsa-miR-5486-5p | hsa-miR-296-2-5p | hsa-miR-106a-3p | hsa-miR-4699-3p |
| hsa-miR-548c-5p | hsa-miR-3128 | hsa-miR-1231 | hsa-miR-582-5p |
| hsa-miR-548d-5p | hsa-miR-3686 | hsa-miR-1298-3p | hsa-miR-642a-3p |
| hsa-miR-548h-5p | hsa-miR-44336-5p | hsa-miR-144-5p | hsa-miR-642b-3p |
| hsa-miR-548i | hsa-miR-4688 | hsa-miR-205-5p | hsa-miR-6760-3p |
| hsa-miR-548j-5p | hsa-miR-4699-5p | hsa-miR-2276-5p | hsa-miR-892c-3p |
| hsa-miR-548k | hsa-miR-6810-5p | hsa-miR-3622a-3p | hsa-miR-4744 |
| hsa-miR-548o-5p | hsa-miR-7641 | hsa-miR-3622b-3p | hsa-miR-503-5p |
| hsa-miR-548w | hsa-miR-8060 | hsa-miR-380-5p | hsa-miR-548v |
| hsa-miR-548y | hsa-miR-8086 | hsa-miR-3918 | hsa-miR-6502-5p |
| hsa-miR-5689 | hsa-miR-4446-3p | hsa-miR-3938 | hsa-miR-6507-5p |
| hsa-miR-5690 | hsa-miR-4711-3p | hsa-miR-44366-5p | hsa-miR-6768-3p |
| hsa-miR-6771-5p | hsa-miR-1265 | hsa-miR-4443 | hsa-miR-6800-5p |
| hsa-miR-3169 | hsa-miR-3174 | hsa-miR-4468 | hsa-miR-6815-5p |
| hsa-miR-3177-5p | hsa-miR-33a-3p | hsa-miR-4650-5p | hsa-miR-6835-5p |
| hsa-miR-3940-5p | hsa-miR-3622a-5p | hsa-miR-4653-3p | hsa-miR-6865-5p |
| hsa-miR-4453 | hsa-miR-4329 | hsa-miR-46666 | hsa-miR-758-3p |
| hsa-miR-4538 | hsa-miR-4417 | hsa-miR-4722-5p | hsa-miR-1286 |
| hsa-miR-4732-5p | hsa-miR-4632-5p | hsa-miR-4734 | hsa-miR-6747-5p |
| hsa-miR-4774-3p | hsa-miR-4733-3p | hsa-miR-4749-5p | hsa-miR-3064-3p |
| hsa-miR-4798-3p | hsa-miR-4761-3p | hsa-miR-4763-5p | hsa-miR-4690-5p |
| hsa-miR-522-3p | hsa-miR-5092 | hsa-miR-490-3p | hsa-miR-4691-3p |
| hsa-miR-542-3p | hsa-miR-541-3p | hsa-miR-493-3p | hsa-miR-1203 |
| hsa-miR-6823-3p | hsa-miR-5589-3p | hsa-miR-495-5p | hsa-miR-1476 |
| hsa-miR-6891-5p | hsa-miR-604 | hsa-miR-5088-5p | hsa-miR-15a-3p |
| hsa-miR-6894-3p | hsa-miR-6512-5p | hsa-miR-5694 | hsa-miR-19a-5p |
| hsa-miR-875-5p | hsa-miR-654-5p | hsa-miR-571 | hsa-miR-196-1-5p |
| hsa-miR-3151-3p | hsa-miR-67696-5p | hsa-miR-576-3p | hsa-miR-196-2-5p |
| hsa-miR-5191 | hsa-miR-6851-5p | hsa-miR-585-5p | hsa-miR-33b-3p |
| hsa-miR-6850-3p | hsa-miR-7162-3p | hsa-miR-615-5p | hsa-miR-3682-5p |
| hsa-miR-6880-3p | hsa-miR-769-5p | hsa-miR-6165 | hsa-miR-4302 |
| hsa-miR-3664-3p | hsa-miR-7843-5p | hsa-miR-6512-3p | hsa-miR-4428 |
| hsa-miR-1237-5p | hsa-miR-8069 | hsa-miR-652-3p | hsa-miR-4435 |
| hsa-miR-1909-3p | hsa-miR-924 | hsa-miR-6720-5p | hsa-miR-4450 |
| hsa-miR-25-5p | hsa-miR-942-3p | hsa-miR-6849-5p | hsa-miR-4499 |
| hsa-miR-2682-5p | hsa-miR-1228-3p | hsa-miR-6875-5p | hsa-miR-4748 |
| hsa-miR-3138 | hsa-miR-1287-5p | hsa-miR-708-3p | hsa-miR-5195-3p |
| hsa-miR-3141 | hsa-miR-1289 | hsa-miR-711 | hsa-miR-548s |
| hsa-miR-371a-3p | hsa-miR-1295b-3p | hsa-miR-7154-3p | hsa-miR-5681b |

FIG. 16 L

| | | | |
|---|---|---|---|
| hsa-miR-371b-3p | hsa-miR-139-5p | hsa-miR-7158-5p | hsa-miR-629-3p |
| hsa-miR-373-3p | hsa-miR-2278 | hsa-miR-8056 | hsa-miR-664a-5p |
| hsa-miR-4508 | hsa-miR-298 | hsa-miR-8084 | hsa-miR-6715b-3p |
| hsa-miR-519e-3p | hsa-miR-3126-5p | hsa-miR-222-3p | hsa-miR-6727-5p |
| hsa-miR-524-3p | hsa-miR-3196 | hsa-miR-3691-5p | hsa-miR-6743-5p |
| hsa-miR-525-3p | hsa-miR-3198 | hsa-miR-3914 | hsa-miR-6763-3p |
| hsa-miR-658 | hsa-miR-342-5p | hsa-miR-4640-3p | hsa-miR-6821-5p |
| hsa-miR-6808-5p | hsa-miR-6836-3p | hsa-miR-7975 | hsa-miR-4743-5p |
| hsa-miR-6836-5p | hsa-miR-6844 | hsa-miR-936 | hsa-miR-4772-5p |
| hsa-miR-6893-5p | hsa-miR-6855-5p | hsa-miR-1470 | hsa-miR-4796-5p |
| hsa-miR-8052 | hsa-miR-7150 | hsa-miR-1908-5p | hsa-miR-504-3p |
| hsa-miR-876-3p | hsa-miR-933 | hsa-miR-3907 | hsa-miR-5586-5p |
| hsa-miR-599 | hsa-miR-1 | hsa-miR-4258 | hsa-miR-601 |
| hsa-miR-1298-5p | hsa-miR-1243 | hsa-miR-4296 | hsa-miR-6757-3p |
| hsa-miR-3137 | hsa-miR-206 | hsa-miR-4313 | hsa-miR-6777-3p |
| hsa-miR-340-3p | hsa-miR-23a-3p | hsa-miR-4474-3p | hsa-miR-7848-3p |
| hsa-miR-3616-5p | hsa-miR-23b-3p | hsa-miR-4484 | hsa-miR-8054 |
| hsa-miR-4263 | hsa-miR-23c | hsa-miR-454-3p | hsa-miR-8055 |
| hsa-miR-4666a-3p | hsa-miR-4682 | hsa-miR-548an | hsa-miR-8062 |
| hsa-miR-499a-5p | hsa-miR-5585-3p | hsa-miR-5580-5p | hsa-miR-8078 |
| hsa-miR-548ag | hsa-miR-6723-5p | hsa-miR-648 | hsa-miR-8079 |
| hsa-miR-548ai | hsa-miR-6891-3p | hsa-miR-6510-5p | hsa-miR-1251-3p |
| hsa-miR-548ba | hsa-miR-101-5p | hsa-miR-6722-3p | hsa-miR-3190-5p |
| hsa-miR-5585-5p | hsa-miR-1246 | hsa-miR-6722-5p | hsa-miR-3591-5p |
| hsa-miR-570-5p | hsa-miR-193a-3p | hsa-miR-6748-5p | hsa-miR-3616-3p |
| hsa-miR-576-5p | hsa-miR-193b-3p | hsa-miR-6769a-3p | hsa-miR-3675-5p |
| hsa-miR-660-5p | hsa-miR-219b-3p | hsa-miR-761 | hsa-miR-3692-5p |
| hsa-miR-8065 | hsa-miR-2681-3p | hsa-miR-764 | hsa-miR-3977 |
| hsa-miR-4259 | hsa-miR-3913-3p | hsa-miR-922 | hsa-miR-4281 |
| hsa-miR-6762-3p | hsa-miR-3922-3p | hsa-miR-3130-5p | hsa-miR-4289 |
| hsa-miR-6842-3p | hsa-miR-4442 | hsa-miR-3140-5p | hsa-miR-4315 |
| hsa-miR-1182 | hsa-miR-6508-5p | hsa-miR-3652 | hsa-miR-4436a |
| hsa-miR-134-5p | hsa-miR-6767-3p | hsa-miR-372-5p | hsa-miR-4713-5p |
| hsa-miR-1912 | hsa-miR-767-5p | hsa-miR-4509 | hsa-miR-4715-3p |
| hsa-miR-2467-5p | hsa-miR-890 | hsa-miR-450b-3p | hsa-miR-4738-3p |
| hsa-miR-3118 | hsa-miR-1184 | hsa-miR-494-3p | hsa-miR-4776-3p |
| hsa-miR-3164 | hsa-miR-1205 | hsa-miR-597-5p | hsa-miR-5187-5p |
| hsa-miR-3194-5p | hsa-miR-1913 | hsa-miR-6738-3p | hsa-miR-626 |
| hsa-miR-328-5p | hsa-miR-193a-5p | hsa-miR-6862-5p | hsa-miR-6755-3p |
| hsa-miR-3615 | hsa-miR-4253 | hsa-miR-758-5p | hsa-miR-6770-5p |

FIG. 16 M

| | | | |
|---|---|---|---|
| hsa-miR-3673 | hsa-miR-486-Sp | hsa-miR-141-3p | hsa-miR-6814-Sp |
| hsa-miR-3975 | hsa-miR-488-3p | hsa-miR-200a-3p | hsa-miR-6876-3p |
| hsa-miR-4661-3p | hsa-miR-6068 | hsa-miR-202-Sp | hsa-miR-6893-3p |
| hsa-miR-4706 | hsa-miR-675-Sp | hsa-miR-2276-3p | hsa-miR-139-3p |
| hsa-miR-4724-Sp | hsa-miR-6779-3p | hsa-miR-3614-3p | hsa-miR-155-Sp |
| hsa-miR-4787-Sp | hsa-miR-6872-3p | hsa-miR-3685 | hsa-miR-224-3p |
| hsa-miR-4788 | hsa-miR-7106-3p | hsa-miR-3944-Sp | hsa-miR-3152-Sp |
| hsa-miR-486-3p | hsa-miR-6805-Sp | hsa-miR-1202 | hsa-miR-593-Sp |
| hsa-miR-5091 | hsa-miR-6820-3p | hsa-miR-135a-5p | hsa-miR-6757-Sp |
| hsa-miR-562 | hsa-miR-6861-Sp | hsa-miR-1356-Sp | hsa-miR-6854-3p |
| hsa-miR-631 | hsa-miR-887-3p | hsa-miR-148a-3p | hsa-miR-7108-Sp |
| hsa-miR-6728-Sp | hsa-miR-940 | hsa-miR-148b-3p | hsa-miR-4457 |
| hsa-miR-6732-Sp | hsa-let-7a-3p | hsa-miR-152-3p | hsa-miR-5003-Sp |
| hsa-miR-6744-3p | hsa-let-7b-3p | hsa-miR-3175 | hsa-miR-5007-Sp |
| hsa-miR-3960 | hsa-let-7f-1-3p | hsa-miR-376c-5p | hsa-miR-6509-3p |
| hsa-miR-4467 | hsa-let-7f-2-3p | hsa-miR-432-3p | hsa-miR-1264 |
| hsa-miR-4741 | hsa-miR-1296-Sp | hsa-miR-5001-3p | hsa-miR-3133 |
| hsa-miR-4774-Sp | hsa-miR-183-3p | hsa-miR-5591-3p | hsa-miR-4536-3p |
| hsa-miR-6877-Sp | hsa-miR-20a-3p | hsa-miR-6090 | hsa-miR-4727-Sp |
| hsa-miR-8072 | hsa-miR-3139 | hsa-miR-6511b-5p | hsa-miR-5580-3p |
| hsa-miR-1247-3p | hsa-miR-323b-3p | hsa-miR-6822-3p | hsa-miR-7109-3p |
| hsa-miR-363-Sp | hsa-miR-3681-3p | hsa-miR-6871-3p | hsa-miR-222-Sp |
| hsa-miR-3656 | hsa-miR-3690 | hsa-miR-6880-Sp | hsa-miR-376a-2-5p |
| hsa-miR-4750-Sp | hsa-miR-4266 | hsa-miR-8076 | hsa-miR-6803-3p |
| hsa-miR-324-3p | hsa-miR-4494 | hsa-miR-920 | hsa-miR-2052 |
| hsa-miR-3940-3p | hsa-miR-4790-Sp | hsa-miR-23a-5p | hsa-miR-4520b-3p |
| hsa-miR-6781-Sp | hsa-miR-663a | hsa-miR-4431 | hsa-miR-5000-3p |
| hsa-miR-5583-3p | hsa-miR-98-3p | hsa-miR-4260 | hsa-miR-6085 |
| hsa-miR-29a-3p | hsa-miR-4718 | hsa-miR-46596-Sp | hsa-miR-7114-3p |
| hsa-miR-29b-3p | hsa-miR-6856-3p | hsa-miR-6795-Sp | hsa-miR-1206 |
| hsa-miR-29c-3p | hsa-miR-1302 | hsa-miR-6887-Sp | hsa-miR-3136-Sp |
| hsa-miR-1245b-3p | hsa-miR-185-3p | hsa-miR-3130-3p | hsa-miR-3157-3p |
| hsa-miR-138-1-3p | hsa-miR-3122 | hsa-miR-3689a-5p | hsa-miR-3766-Sp |
| hsa-miR-200c-5p | hsa-miR-3674 | hsa-miR-36896-Sp | hsa-miR-4290 |
| hsa-miR-4474-Sp | hsa-miR-4475 | hsa-miR-3689e | hsa-miR-6852-Sp |
| hsa-miR-5587-3p | hsa-miR-4490 | hsa-miR-3689f | hsa-miR-885-3p |
| hsa-miR-1244 | hsa-miR-4790-3p | hsa-miR-4714-3p | hsa-miR-935 |
| hsa-miR-125b-2-3p | hsa-miR-548n | hsa-miR-4717-Sp | hsa-miR-3119 |
| hsa-miR-381-Sp | hsa-miR-554 | hsa-miR-500b-3p | hsa-miR-6509-Sp |
| hsa-miR-6866-3p | hsa-miR-555 | hsa-miR-582-3p | hsa-miR-8068 |

FIG. 16 N

| hsa-miR-29c-5p | hsa-miR-6069 | hsa-miR-6778-3p | hsa-miR-217 |
|---|---|---|---|
| hsa-miR-325 | hsa-miR-608 | hsa-miR-6806-Sp | hsa-miR-24-1-Sp |
| hsa-miR-3974 | hsa-miR-6732-3p | hsa-miR-3978 | hsa-miR-24-2-Sp |
| hsa-miR-451a | hsa-miR-6784-Sp | hsa-miR-888-3p | hsa-miR-26a-1-3p |
| hsa-miR-4633-Sp | hsa-miR-6798-3p | hsa-miR-299-3p | hsa-miR-26a-2-3p |
| hsa-miR-46626 | hsa-miR-7847-3p | hsa-miR-370-3p | hsa-miR-28-3p |
| hsa-miR-517a-3p | hsa-miR-3649 | hsa-miR-4769-Sp | hsa-miR-3074-3p |
| hsa-miR-517b-3p | hsa-miR-4659a-5p | hsa-miR-8066 | hsa-miR-8073 |
| hsa-miR-517c-3p | hsa-miR-580-Sp | hsa-miR-99a-5p | hsa-miR-515-3p |
| hsa-miR-611 | hsa-miR-1234-3p | hsa-miR-146a-3p | hsa-miR-3131 |
| hsa-miR-6827-Sp | hsa-miR-3692-3p | hsa-miR-1538 | hsa-miR-362-Sp |
| hsa-miR-103a-2-5p | hsa-miR-4300 | hsa-miR-4485 | hsa-miR-4749-3p |
| hsa-miR-3236-Sp | hsa-miR-4764-3p | hsa-miR-488-Sp | hsa-miR-5006-Sp |
| hsa-miR-410-Sp | hsa-miR-550b-3p | hsa-miR-6075 | hsa-miR-516a-5p |
| hsa-miR-494-Sp | hsa-miR-5591-Sp | hsa-miR-6890-Sp | hsa-miR-548ar-3p |
| hsa-miR-6087 | hsa-miR-6832-3p | hsa-miR-744-Sp | hsa-miR-520d-5p |
| hsa-miR-941 | hsa-miR-7107-Sp | hsa-miR-138-5p | hsa-miR-524-Sp |
| hsa-miR-3917 | hsa-miR-4694-Sp | hsa-miR-320a | hsa-miR-548av-3p |
| hsa-miR-1250-Sp | hsa-miR-506-Sp | hsa-miR-3206 | hsa-miR-548g-3p |
| hsa-miR-133a-5p | hsa-miR-10a-5p | hsa-miR-320c | hsa-miR-5582-3p |
| hsa-miR-365a-3p | hsa-miR-10b-5p | hsa-miR-320d | hsa-miR-6074 |
| hsa-miR-365b-3p | hsa-miR-6740-Sp | hsa-miR-4280 | hsa-miR-132-3p |
| hsa-miR-4632-3p | hsa-miR-7850-Sp | hsa-miR-4429 | hsa-miR-212-3p |
| hsa-miR-943 | hsa-miR-2355-3p | hsa-miR-4801 | hsa-miR-3115 |
| hsa-miR-3672 | hsa-miR-3199 | hsa-miR-492 | hsa-miR-409-Sp |
| hsa-miR-1324 | hsa-miR-4781-3p | hsa-miR-633 | hsa-miR-6072 |
| hsa-miR-4781-Sp | hsa-miR-635 | hsa-miR-6506-Sp | hsa-miR-7161-3p |
| hsa-miR-1287-3p | hsa-miR-659-Sp | hsa-miR-7156-Sp | hsa-miR-7702 |
| hsa-miR-191-Sp | hsa-miR-661 | hsa-miR-7977 | hsa-miR-1273h-3p |
| hsa-miR-219a-2-3p | hsa-miR-6726-Sp | hsa-miR-3144-3p | hsa-miR-132-Sp |
| hsa-miR-3146 | hsa-miR-6769a-5p | hsa-miR-548aw | hsa-miR-218-2-3p |
| hsa-miR-4528 | hsa-miR-6774-5p | hsa-miR-548b-3p | hsa-miR-3117-Sp |
| hsa-miR-4684-Sp | hsa-miR-6802-3p | hsa-miR-561-3p | hsa-miR-3684 |
| hsa-miR-1909-Sp | hsa-miR-6838-3p | hsa-miR-181c-3p | hsa-miR-412-Sp |
| hsa-miR-3124-3p | hsa-miR-100-5p | hsa-miR-203b-3p | hsa-miR-4299 |
| hsa-miR-6770-3p | hsa-miR-1273g-5p | hsa-miR-221-Sp | hsa-miR-487a-5p |
| hsa-miR-1227-3p | hsa-miR-378a-3p | hsa-miR-3619-3p | hsa-miR-4876-Sp |
| hsa-miR-4454 | hsa-miR-3786 | hsa-miR-3935 | hsa-miR-591 |
| hsa-miR-12556-Sp | hsa-miR-378c | hsa-miR-4477a | hsa-miR-6502-3p |
| hsa-miR-454-Sp | hsa-miR-378d | hsa-miR-450a-2-3p | hsa-miR-6716-Sp |

FIG. 16 P

| | | | |
|---|---|---|---|
| hsa-miR-4738-5p | hsa-miR-378e | hsa-miR-4778-5p | hsa-miR-6501-5p |
| hsa-miR-6812-3p | hsa-miR-378f | hsa-miR-548au-3p | hsa-miR-1036 |
| hsa-miR-503-3p | hsa-miR-378h | hsa-miR-548az-5p | hsa-miR-1066-3p |
| hsa-miR-5587-5p | hsa-miR-378i | hsa-miR-548t-5p | hsa-miR-10a-3p |
| hsa-miR-6861-3p | hsa-miR-422a | hsa-miR-628-3p | hsa-miR-130a-3p |
| hsa-miR-4278 | hsa-miR-4646-5p | hsa-miR-6765-3p | hsa-miR-1306-3p |
| hsa-miR-155-3p | hsa-miR-6774-3p | hsa-miR-6785-3p | hsa-miR-154-3p |
| hsa-miR-1199-3p | hsa-miR-218-1-3p | hsa-miR-6746-3p | hsa-miR-302e |
| hsa-miR-124-3p | hsa-miR-301a-3p | hsa-miR-1227-5p | hsa-miR-448 |
| hsa-miR-1256-1-3p | hsa-miR-3016 | hsa-miR-3687 | hsa-miR-5094 |
| hsa-miR-210-3p | hsa-miR-3129-5p | hsa-miR-4800-3p | hsa-miR-572 |
| hsa-miR-365a-5p | hsa-miR-363-3p | hsa-miR-6743-3p | hsa-miR-6720-3p |
| hsa-miR-3656-5p | hsa-miR-3666 | hsa-miR-6773-5p | hsa-miR-136-5p |
| hsa-miR-4539 | hsa-miR-367-3p | hsa-miR-7158-3p | hsa-let-7a-2-3p |
| hsa-miR-423-3p | hsa-miR-4295 | hsa-miR-1936-5p | hsa-miR-135a-3p |
| hsa-miR-1247-5p | hsa-miR-487a-3p | hsa-miR-4523 | hsa-miR-4697-3p |
| hsa-miR-996-5p | hsa-miR-5196-3p | hsa-miR-4665-3p | hsa-miR-501-5p |
| hsa-miR-4449 | hsa-miR-6811-3p | hsa-miR-548ao-3p | hsa-miR-6797-3p |
| hsa-miR-3944-3p | hsa-miR-4703-5p | hsa-miR-200a-5p | hsa-miR-770-5p |
| hsa-miR-4999-3p | hsa-miR-4704-5p | hsa-miR-2006-5p | hsa-let-7g-3p |
| hsa-miR-3181 | hsa-miR-4766-3p | hsa-miR-3162-3p | hsa-miR-874-5p |
| hsa-miR-6749-5p | hsa-miR-6886-3p | hsa-miR-652-5p | hsa-miR-196a-3p |
| hsa-miR-3683 | hsa-miR-548as-3p | hsa-miR-4677-5p | hsa-miR-4707-5p |
| hsa-miR-4661-5p | hsa-miR-44776 | hsa-miR-1307-3p | hsa-miR-6820-5p |
| hsa-miR-570-3p | hsa-miR-4680-5p | hsa-miR-1469 | hsa-miR-2909 |
| hsa-miR-4670-5p | hsa-miR-5687 | hsa-miR-3178 | hsa-miR-302f |
| hsa-miR-6716-3p | hsa-miR-6750-3p | hsa-miR-3180 | hsa-miR-3934-3p |
| hsa-miR-2036-5p | hsa-miR-27a-5p | hsa-miR-3180-3p | hsa-miR-5186 |
| hsa-miR-6718-5p | hsa-miR-3660 | hsa-miR-369-5p | hsa-miR-518c-3p |
| hsa-miR-1306-3p | hsa-miR-4462 | hsa-miR-4638-5p | hsa-miR-518d-3p |
| hsa-miR-4655-5p | hsa-miR-199a-3p | hsa-miR-551a | hsa-miR-518e-3p |
| hsa-miR-6717-5p | hsa-miR-1996-3p | hsa-miR-5516-3p | hsa-miR-6775-5p |
| hsa-miR-653-5p | hsa-miR-223-3p | hsa-miR-6789-3p | hsa-miR-3176 |
| hsa-miR-483-5p | hsa-miR-3923 | hsa-miR-6816-5p | hsa-miR-324-5p |
| hsa-miR-4876-3p | hsa-miR-3973 | hsa-let-7i-3p | hsa-miR-4730 |
| hsa-miR-6790-3p | hsa-miR-5584-3p | hsa-miR-18a-3p | hsa-miR-6831-5p |
| hsa-miR-124-5p | hsa-miR-1249 | hsa-miR-296-1-5p | hsa-miR-151a-5p |
| hsa-miR-6814-3p | hsa-miR-1284 | hsa-miR-606 | hsa-miR-1516 |
| hsa-miR-8074 | hsa-miR-2006-3p | hsa-miR-6506-3p | hsa-miR-3150a-5p |
| hsa-miR-4767 | hsa-miR-200c-3p | hsa-miR-6738-5p | hsa-miR-31506-5p |

FIG. 16 Q

| | | | |
|---|---|---|---|
| hsa-miR-191-3p | hsa-miR-429 | hsa-miR-208a-3p | hsa-miR-375 |
| hsa-miR-4783-3p | hsa-miR-520f-5p | hsa-miR-208b-3p | hsa-miR-500a-5p |
| hsa-miR-6827-3p | hsa-miR-4506 | hsa-miR-302a-3p | hsa-miR-181a-3p |
| hsa-miR-7846-3p | hsa-miR-4532 | hsa-miR-302b-3p | hsa-miR-3618 |
| hsa-miR-1471 | hsa-miR-5009-Sp | hsa-miR-302c-3p | hsa-miR-431-Sp |
| hsa-miR-4707-3p | hsa-miR-105-3p | hsa-miR-302d-3p | hsa-miR-624-Sp |
| hsa-miR-6840-Sp | hsa-miR-3648 | hsa-miR-2277-3p | hsa-miR-3116 |
| hsa-miR-1281 | hsa-miR-4655-3p | hsa-miR-509-Sp | hsa-miR-4433-Sp |
| hsa-miR-1180-3p | hsa-miR-506-3p | hsa-miR-95-3p | hsa-miR-4804-Sp |
| hsa-miR-2277-Sp | hsa-miR-6084 | hsa-miR-376a-5p | hsa-miR-5708 |
| hsa-miR-1181 | hsa-miR-938 | hsa-miR-5705 | hsa-miR-6795-3p |
| hsa-miR-6850-Sp | hsa-miR-3713 | hsa-miR-1285-Sp | hsa-miR-1301-Sp |
| hsa-miR-4746-Sp | hsa-miR-1908-3p | hsa-miR-181d-3p | hsa-miR-4740-3p |
| hsa-miR-926-Sp | hsa-miR-1915-Sp | hsa-miR-4444 | hsa-miR-615-3p |
| hsa-miR-6872-Sp | hsa-miR-638 | hsa-miR-3171 | hsa-miR-2114-3p |
| hsa-miR-921 | hsa-miR-6841-3p | hsa-miR-552-3p | hsa-miR-4540 |
| hsa-miR-7112-Sp | hsa-miR-138-2-3p | hsa-miR-5684 | hsa-miR-6863 |
| hsa-miR-489-Sp | hsa-miR-621 | hsa-miR-3193 | hsa-miR-151a-3p |
| hsa-miR-4757-3p | hsa-miR-6853-3p | hsa-miR-4520a-5p | hsa-miR-4671-Sp |
| hsa-miR-614 | hsa-miR-1973 | hsa-miR-45206-Sp | hsa-miR-218-Sp |
| hsa-miR-4664-3p | hsa-miR-4637 | hsa-miR-526b-3p | hsa-miR-339-3p |
| hsa-miR-196b-3p | hsa-miR-500a-3p | hsa-miR-8053 | hsa-miR-4473 |
| hsa-miR-3610 | hsa-miR-6082 | hsa-miR-4305 | hsa-miR-5704 |
| hsa-miR-5188 | hsa-miR-196a-5p | hsa-miR-7704 | hsa-miR-187-3p |
| hsa-miR-6761-3p | hsa-miR-1966-Sp | hsa-miR-12456-Sp | hsa-miR-6804-3p |
| hsa-let-7d-3p | hsa-miR-891a-5p | hsa-miR-4466 | hsa-miR-4783-Sp |
| hsa-miR-6510-3p | hsa-miR-412-3p | hsa-miR-4440 | hsa-miR-566 |
| hsa-miR-1277-3p | hsa-miR-4671-3p | hsa-miR-6078 | hsa-miR-6777-Sp |
| hsa-miR-4785 | hsa-miR-4777-3p | hsa-miR-505-3p | hsa-miR-1295a |
| hsa-miR-1204 | hsa-miR-5571-3p | hsa-miR-6825-3p | hsa-miR-1468-Sp |
| hsa-miR-4737 | hsa-miR-6070 | hsa-miR-8059 | hsa-miR-1539 |
| hsa-miR-197-Sp | hsa-miR-3168 | hsa-miR-127-Sp | hsa-miR-521 |
| hsa-miR-6767-Sp | hsa-miR-4304 | hsa-miR-3943 | hsa-miR-602 |
| hsa-miR-3124-Sp | hsa-miR-6726-3p | hsa-miR-6883-3p | hsa-miR-425-3p |
| hsa-miR-3621 | hsa-miR-760 | hsa-miR-3166 | hsa-miR-7108-3p |
| hsa-miR-4285 | hsa-miR-585-3p | hsa-miR-431-3p | hsa-miR-7706 |
| hsa-miR-4634 | hsa-miR-7844-Sp | hsa-miR-6865-3p | hsa-miR-3945 |
| hsa-miR-4479 | hsa-miR-186-3p | hsa-miR-4745-3p | hsa-miR-4787-3p |
| hsa-let-7d-5p | hsa-miR-1278 | hsa-miR-424-3p | hsa-miR-518a-3p |
| hsa-miR-1224-3p | hsa-miR-194-Sp | hsa-miR-1273c | hsa-miR-518f-3p |

FIG. 16 R

| hsa-miR-202-3p | hsa-miR-9-5p | hsa-miR-1282 | hsa-miR-6869-3p |
|---|---|---|---|
| hsa-miR-3127-3p | hsa-miR-3605-3p | hsa-miR-5089-Sp | hsa-miR-934 |
| hsa-miR-361-3p | hsa-miR-4262 | hsa-miR-1251-Sp | hsa-miR-3678-Sp |
| hsa-miR-4276 | hsa-miR-4275 | hsa-miR-1268a | hsa-miR-718 |
| hsa-miR-4425 | hsa-miR-610 | hsa-miR-12686 | hsa-miR-668-Sp |
| hsa-miR-4458 | hsa-miR-4681 | hsa-miR-337-Sp | hsa-miR-6786-3p |
| hsa-miR-4687-Sp | hsa-miR-509-3-Sp | hsa-miR-3669 | hsa-miR-598-3p |
| hsa-miR-4690-3p | | | |
| hsa-miR-5581-3p | | | |
| hsa-miR-587 | | | |
| hsa-miR-662 | | | |
| hsa-miR-6733-3p | | | |
| hsa-miR-6752-3p | | | |
| hsa-miR-6780a-3p | | | |
| hsa-miR-6809-Sp | | | |
| hsa-miR-6839-3p | | | |
| hsa-miR-148a-5p | | | |
| hsa-miR-1486-Sp | | | |
| hsa-miR-150-Sp | | | |
| hsa-miR-182-3p | | | |
| hsa-miR-199a-5p | | | |
| hsa-miR-1996-Sp | | | |
| hsa-miR-215-3p | | | |

TABLE 3

FIG. 17 A

Intersecting list of microRNA miRBase symbols found in Table 2 and immune cell-derived EV microRNA expression matrix

| | | | |
|---|---|---|---|
| hsa-miR-496 | hsa-miR-557 | hsa-miR-137 | hsa-miR-554 |
| hsa-miR-559 | hsa-miR-639 | hsa-miR-483-3p | hsa-miR-555 |
| hsa-miR-590-3p | hsa-miR-609 | hsa-miR-491-3p | hsa-miR-608 |
| hsa-miR-575 | hsa-miR-133b | hsa-miR-548a-3p | hsa-miR-920 |
| hsa-miR-596 | hsa-miR-184 | hsa-miR-556-5p | hsa-miR-582-3p |
| hsa-miR-603 | hsa-miR-384 | hsa-miR-618 | hsa-miR-299-3p |
| hsa-miR-612 | hsa-miR-548a-5p | hsa-miR-330-3p | hsa-miR-885-3p |
| hsa-miR-622 | hsa-miR-548b-5p | hsa-miR-331-3p | hsa-miR-935 |
| hsa-miR-567 | hsa-miR-548c-5p | hsa-miR-568 | hsa-miR-217 |
| hsa-miR-630 | hsa-miR-548d-5p | hsa-miR-573 | hsa-miR-28-3p |
| hsa-miR-767-3p | hsa-miR-604 | hsa-miR-574-5p | hsa-miR-635 |
| hsa-miR-142-5p | hsa-miR-654-5p | hsa-miR-485-5p | hsa-miR-661 |
| hsa-miR-498 | hsa-miR-769-5p | hsa-miR-515-5p | hsa-miR-422a |
| hsa-miR-520h | hsa-miR-924 | hsa-miR-636 | hsa-miR-492 |
| hsa-miR-617 | hsa-miR-139-5p | hsa-miR-361-5p | hsa-miR-633 |
| hsa-miR-944 | hsa-miR-298 | hsa-miR-532-5p | hsa-miR-548b-3p |
| hsa-miR-125a-3p | hsa-miR-342-5p | hsa-miR-543 | hsa-miR-628-3p |
| hsa-miR-296-3p | hsa-miR-490-3p | hsa-miR-337-3p | hsa-miR-515-3p |
| hsa-miR-508-3p | hsa-miR-571 | hsa-miR-338-3p | hsa-miR-362-5p |
| hsa-miR-519b-3p | hsa-miR-576-3p | hsa-miR-34c-3p | hsa-miR-516a-5p |
| hsa-miR-519c-3p | hsa-miR-615-5p | hsa-miR-590-5p | hsa-miR-520d-5p |
| hsa-miR-520a-3p | hsa-miR-147b | hsa-miR-876-5p | hsa-miR-524-5p |
| hsa-miR-520b | hsa-miR-933 | hsa-miR-107 | hsa-miR-409-5p |
| hsa-miR-520c-3p | hsa-miR-1 | hsa-miR-1225-5p | hsa-miR-591 |
| hsa-miR-520d-3p | hsa-miR-206 | hsa-miR-326 | hsa-miR-301b |
| hsa-miR-520e | hsa-miR-193a-3p | hsa-miR-330-5p | hsa-miR-199b-3p |
| hsa-miR-542-5p | hsa-miR-767-5p | hsa-miR-339-5p | hsa-miR-429 |
| hsa-miR-613 | hsa-miR-890 | hsa-miR-342-3p | hsa-miR-369-5p |
| hsa-miR-188-3p | hsa-miR-193a-5p | hsa-miR-513a-3p | hsa-miR-551a |
| hsa-miR-188-5p | hsa-miR-486-5p | hsa-miR-140-5p | hsa-miR-606 |
| hsa-miR-369-3p | hsa-miR-936 | hsa-miR-501-3p | hsa-miR-448 |
| hsa-miR-455-3p | hsa-miR-648 | hsa-miR-502-3p | hsa-miR-572 |
| hsa-miR-508-5p | hsa-miR-922 | hsa-miR-509-3p | hsa-miR-501-5p |

FIG. 17 B

| | | | |
|---|---|---|---|
| hsa-miR-527 | hsa-miR-450b-3p | hsa-miR-520a-5p | hsa-miR-770-5p |
| hsa-miR-556-3p | hsa-miR-601 | hsa-miR-525-5p | hsa-miR-518b |
| hsa-miR-583 | hsa-miR-626 | hsa-miR-595 | hsa-miR-518d-3p |
| hsa-miR-623 | hsa-miR-139-3p | hsa-miR-892b | hsa-miR-324-5p |
| hsa-miR-634 | hsa-miR-542-3p | hsa-miR-1231 | hsa-miR-375 |
| hsa-miR-650 | hsa-miR-875-5p | hsa-miR-632 | hsa-miR-324-3p |
| hsa-miR-512-5p | hsa-miR-524-3p | hsa-miR-643 | hsa-miR-325 |
| hsa-miR-558 | hsa-miR-525-3p | hsa-miR-885-5p | hsa-miR-611 |
| hsa-miR-637 | hsa-miR-658 | hsa-miR-582-5p | hsa-miR-941 |
| hsa-miR-654-3p | hsa-miR-876-3p | hsa-miR-331-5p | hsa-miR-943 |
| hsa-miR-765 | hsa-miR-599 | hsa-miR-455-5p | hsa-miR-938 |
| hsa-miR-1224-5p | hsa-miR-576-5p | hsa-miR-502-5p | hsa-miR-638 |
| hsa-miR-875-3p | hsa-miR-486-3p | hsa-miR-891b | hsa-miR-621 |
| hsa-miR-892a | hsa-miR-562 | hsa-miR-142-3p | hsa-miR-760 |
| hsa-miR-146b-3p | hsa-miR-631 | hsa-miR-198 | hsa-miR-610 |
| hsa-miR-299-5p | hsa-miR-940 | hsa-miR-553 | hsa-miR-509-3-5p |
| hsa-miR-338-5p | hsa-miR-34c-5p | hsa-miR-146b-5p | hsa-miR-509-5p |
| hsa-miR-346 | hsa-miR-423-5p | hsa-miR-512-3p | hsa-miR-127-5p |
| hsa-miR-484 | hsa-miR-449a | hsa-miR-518d-5p | hsa-miR-337-5p |
| hsa-miR-513a-5p | hsa-miR-491-5p | hsa-miR-532-3p | hsa-miR-615-3p |
| hsa-miR-569 | hsa-miR-548c-3p | hsa-miR-588 | hsa-miR-339-3p |
| hsa-miR-641 | hsa-miR-563 | hsa-miR-628-5p | hsa-miR-566 |
| hsa-miR-647 | hsa-miR-607 | hsa-miR-645 | hsa-miR-521 |
| hsa-miR-129-5p | hsa-miR-620 | hsa-miR-646 | hsa-miR-602 |
| hsa-miR-409-3p | hsa-miR-649 | hsa-miR-769-3p | hsa-miR-518a-3p |
| hsa-miR-577 | hsa-miR-657 | hsa-miR-300 | hsa-miR-934 |
| hsa-miR-1225-3p | hsa-miR-671-5p | hsa-miR-485-3p | hsa-miR-423-3p |
| hsa-miR-140-3p | hsa-miR-592 | hsa-miR-490-5p | hsa-miR-483-5p |
| hsa-miR-190b | hsa-miR-125a-5p | hsa-miR-516a-3p | hsa-miR-921 |
| hsa-miR-296-5p | hsa-miR-362-3p | hsa-miR-297 | hsa-miR-614 |
| hsa-miR-564 | hsa-miR-665 | hsa-miR-421 | hsa-miR-199a-5p |
| hsa-miR-574-3p | hsa-miR-802 | hsa-miR-450b-5p | hsa-miR-199b-5p |
| hsa-miR-1224-3p | hsa-miR-28-5p | hsa-miR-507 | hsa-miR-586 |
| hsa-miR-361-3p | hsa-miR-578 | hsa-miR-548d-3p | |
| hsa-miR-587 | hsa-miR-581 | hsa-miR-600 | |
| hsa-miR-662 | hsa-miR-671-3p | hsa-miR-640 | |

FIG. 18 A

TABLE 4

| microRNAs present in immune-cell derived EV matrix after programmatic processing and normalization ||||
|---|---|---|---|
| hsa-miR-620 | hsa-miR-181 a* | hsa-miR-297 | hsa-miR-422a |
| hsa-miR-384 | hsa-miR-181 b | hsa-miR-298 | hsa-miR-423-3p |
| hsa-miR-1 | hsa-miR-181 c | hsa-miR-299-3p | hsa-miR-423-Sp |
| hsa-miR-100 | hsa-miR-181c* | hsa-miR-299-Sp | hsa-miR-424 |
| hsa-miR-100* | hsa-miR-181 d | hsa-miR-29a | hsa-miR-424* |
| hsa-miR-10 I | hsa-miR-182 | hsa-miR-29a* | hsa-miR-425 |
| hsa-miR-101 * | hsa-miR-182* | hsa-miR-296 | hsa-miR-425* |
| hsa-miR-103 | hsa-miR-183 | hsa-miR-296-1 * | hsa-miR-429 |
| hsa-miR-105 | hsa-miR-183* | hsa-miR-296-2* | hsa-miR-431 |
| hsa-miR-105* | hsa-miR-184 | hsa-miR-29c | hsa-miR-431 * |
| hsa-miR-106a | hsa-miR-185 | hsa-miR-29c* | hsa-miR-432 |
| hsa-miR-106a* | hsa-miR-185* | hsa-miR-300 | hsa-miR-432* |
| hsa-miR-1066 | hsa-miR-186 | hsa-miR-301a | hsa-miR-433 |
| hsa-miR-1066* | hsa-miR-186* | hsa-miR-301 b | hsa-miR-448 |
| hsa-miR-107 | hsa-miR-187 | hsa-miR-302a | hsa-miR-449a |
| hsa-miR-1 Oa | hsa-miR-187* | hsa-miR-302a* | hsa-miR-4496 |
| hsa-miR-1 Oa* | hsa-miR-188-3p | hsa-miR-3026 | hsa-miR-450a |
| hsa-miR-1 Ob | hsa-miR-188-Sp | hsa-miR-3026* | hsa-miR-450b-3p |
| hsa-miR-1 Ob* | hsa-miR-18a | hsa-miR-302c | hsa-miR-4506-Sp |
| hsa-miR-122 | hsa-miR-18a* | hsa-miR-302c* | hsa-miR-451 |
| hsa-miR-122* | hsa-miR-186 | hsa-miR-302d | hsa-miR-452 |
| hsa-miR-1224-3p | hsa-miR-186* | hsa-miR-302d* | hsa-miR-452* |
| hsa-miR-1224-Sp | hsa-miR-190 | hsa-miR-30a | hsa-miR-453 |
| hsa-miR-1225-3p | hsa-miR-1906 | hsa-miR-30a* | hsa-miR-454 |
| hsa-miR-1225-Sp | hsa-miR-191 | hsa-miR-306 | hsa-miR-454* |
| hsa-miR-1226 | hsa-miR-191 * | hsa-miR-306* | hsa-miR-455-3p |
| hsa-miR-1226* | hsa-miR-192 | hsa-miR-30c | hsa-miR-455-Sp |
| hsa-miR-1227 | hsa-miR-192* | hsa-miR-30c-1 * | hsa-miR-483-3p |
| hsa-miR-1228 | hsa-miR-193a-3p | hsa-miR-30c-2* | hsa-miR-483-Sp |
| hsa-miR-1228* | hsa-miR-193a-5p | hsa-miR-30d | hsa-miR-484 |
| hsa-miR-1229 | hsa-miR-1936 | hsa-miR-30d* | hsa-miR-485-3p |
| hsa-miR-1231 | hsa-miR-1936* | hsa-miR-30e | hsa-miR-485-Sp |

FIG. 18 B

| | | | |
|---|---|---|---|
| hsa-miR-1233 | hsa-miR-194 | hsa-miR-30e* | hsa-miR-486-3p |
| hsa-miR-1234 | hsa-miR-194* | hsa-miR-31 | hsa-miR-486-5p |
| hsa-miR-1236 | hsa-miR-195 | hsa-miR-31 * | hsa-miR-487a |
| hsa-miR-1237 | hsa-miR-195* | hsa-miR-32 | hsa-miR-4876 |
| hsa-miR-1238 | hsa-miR-196a | hsa-miR-32* | hsa-miR-488 |
| hsa-miR-124 | hsa-miR-196a* | hsa-miR-320 | hsa-miR-488* |
| hsa-miR-124* | hsa-miR-1966 | hsa-miR-323-3p | hsa-miR-489 |
| hsa-miR-125a-3p | hsa-miR-197 | hsa-miR-323-5p | hsa-miR-490-3p |
| hsa-miR-125a-5p | hsa-miR-198 | hsa-miR-324-3p | hsa-miR-490-5p |
| hsa-miR-1256 | hsa-miR-199a-5p | hsa-miR-324-5p | hsa-miR-491-3p |
| hsa-miR-1256-1 * | hsa-miR-199b-3p | hsa-miR-325 | hsa-miR-491-5p |
| hsa-miR-1256-2* | hsa-miR-1996-5p | hsa-miR-326 | hsa-miR-492 |
| hsa-miR-126 | hsa-miR-19a | hsa-miR-328 | hsa-miR-493 |
| hsa-miR-126* | hsa-miR-19a* | hsa-miR-329 | hsa-miR-493* |
| hsa-miR-127-3p | hsa-miR-196 | hsa-miR-330-3p | hsa-miR-494 |
| hsa-miR-127-5p | hsa-miR-196-1 * | hsa-miR-330-5p | hsa-miR-495 |
| hsa-miR-128 | hsa-miR-196-2* | hsa-miR-331-3p | hsa-miR-496 |
| hsa-miR-129-3p | hsa-miR-200a | hsa-miR-331-5p | hsa-miR-497 |
| hsa-miR-129-5p | hsa-miR-200a* | hsa-miR-335 | hsa-miR-497* |
| hsa-miR-129* | hsa-miR-2006 | hsa-miR-335* | hsa-miR-498 |
| hsa-miR-130a | hsa-miR-2006* | hsa-miR-337-3p | hsa-miR-499-3p |
| hsa-miR-130a* | hsa-miR-200c | hsa-miR-337-5p | hsa-miR-499-5p |
| hsa-miR-1306 | hsa-miR-200c* | hsa-miR-338-3p | hsa-miR-500 |
| hsa-miR-1306* | hsa-miR-202 | hsa-miR-338-5p | hsa-miR-500* |
| hsa-miR-132 | hsa-miR-202* | hsa-miR-339-3p | hsa-miR-501-3p |
| hsa-miR-132* | hsa-miR-203 | hsa-miR-339-5p | hsa-miR-501-5p |
| hsa-miR-133a | hsa-miR-204 | hsa-miR-33a | hsa-miR-502-3p |
| hsa-miR-1336 | hsa-miR-205 | hsa-miR-33a* | hsa-miR-502-5p |
| hsa-miR-134 | hsa-miR-206 | hsa-miR-336 | hsa-miR-503 |
| hsa-miR-135a | hsa-miR-208a | hsa-miR-336* | hsa-miR-504 |
| hsa-miR-135a* | hsa-miR-2086 | hsa-miR-340 | hsa-miR-505 |
| hsa-miR-1356 | hsa-miR-20a | hsa-miR-340* | hsa-miR-505* |
| hsa-miR-1356* | hsa-miR-20a* | hsa-miR-342-3p | hsa-miR-506 |
| hsa-miR-136 | hsa-miR-206 | hsa-miR-342-5p | hsa-miR-507 |
| hsa-miR-136* | hsa-miR-206* | hsa-miR-345 | hsa-miR-508-3p |
| hsa-miR-137 | hsa-miR-21 | hsa-miR-346 | hsa-miR-508-5p |
| hsa-miR-138 | hsa-miR-21 * | hsa-miR-34a | hsa-miR-509-3-5p |
| hsa-miR-138-1 * | hsa-miR-210 | hsa-miR-34a* | hsa-miR-509-3p |
| hsa-miR-138-2 * | hsa-miR-211 | hsa-miR-346 | hsa-miR-509-5p |
| hsa-miR-139-3p | hsa-miR-212 | hsa-miR-346* | hsa-miR-510 |

FIG. 18 C

| | | | |
|---|---|---|---|
| hsa-miR-139-5p | hsa-miR-214 | hsa-miR-34c-3p | hsa-miR-511 |
| hsa-miR-140-3p | hsa-miR-214* | hsa-miR-34c-5p | hsa-miR-512-3p |
| hsa-miR-140-5p | hsa-miR-215 | hsa-miR-361-3p | hsa-miR-512-5p |
| hsa-miR-141 | hsa-miR-216a | hsa-miR-361-5p | hsa-miR-513a-3p |
| hsa-miR-141* | hsa-miR-216b | hsa-miR-362-3p | hsa-miR-513a-5p |
| hsa-miR-142-3p | hsa-miR-217 | hsa-miR-362-5p | hsa-miR-513b |
| hsa-miR-142-5p | hsa-miR-218 | hsa-miR-363 | hsa-miR-513c |
| hsa-miR-143 | hsa-miR-218-1* | hsa-miR-363* | hsa-miR-514 |
| hsa-miR-143* | hsa-miR-218-2* | hsa-miR-365 | hsa-miR-515-3p |
| hsa-miR-144 | hsa-miR-219-1-3p | hsa-miR-367 | hsa-miR-515-5p |
| hsa-miR-144* | hsa-miR-219-2-3p | hsa-miR-367* | hsa-miR-516a-3p |
| hsa-miR-145 | hsa-miR-219-5p | hsa-miR-369-3p | hsa-miR-516a-5p |
| hsa-miR-145* | hsa-miR-22 | hsa-miR-369-5p | hsa-miR-516b |
| hsa-miR-146a | hsa-miR-22* | hsa-miR-370 | hsa-miR-517* |
| hsa-miR-146a* | hsa-miR-220a | hsa-miR-371-3p | hsa-miR-517a |
| hsa-miR-146b-3p | hsa-miR-220b | hsa-miR-371-5p | hsa-miR-517b |
| hsa-miR-146b-5p | hsa-miR-220c | hsa-miR-372 | hsa-miR-517c |
| hsa-miR-147 | hsa-miR-221 | hsa-miR-373 | hsa-miR-518a-3p |
| hsa-miR-147b | hsa-miR-221* | hsa-miR-373* | hsa-miR-518b |
| hsa-miR-148a | hsa-miR-222 | hsa-miR-374a | hsa-miR-518c |
| hsa-miR-148a* | hsa-miR-222* | hsa-miR-374a* | hsa-miR-518c* |
| hsa-miR-148b | hsa-miR-223 | hsa-miR-374b | hsa-miR-518d-3p |
| hsa-miR-148b* | hsa-miR-223* | hsa-miR-374b* | hsa-miR-518d-5p |
| hsa-miR-149 | hsa-miR-224 | hsa-miR-375 | hsa-miR-518e |
| hsa-miR-149* | hsa-miR-23a | hsa-miR-376a | hsa-miR-518e* |
| hsa-miR-150 | hsa-miR-23a* | hsa-miR-376a* | hsa-miR-518f |
| hsa-miR-150* | hsa-miR-23b | hsa-miR-376b | hsa-miR-518f* |
| hsa-miR-151-3p | hsa-miR-23b* | hsa-miR-376c | hsa-miR-519a |
| hsa-miR-151-5p | hsa-miR-24 | hsa-miR-377 | hsa-miR-519b-3p |
| hsa-miR-152 | hsa-miR-24-1* | hsa-miR-377* | hsa-miR-519c-3p |
| hsa-miR-153 | hsa-miR-24-2* | hsa-miR-378 | hsa-miR-519d |
| hsa-miR-154 | hsa-miR-25 | hsa-miR-378* | hsa-miR-519e |
| hsa-miR-154* | hsa-miR-25* | hsa-miR-379 | hsa-miR-519e* |
| hsa-miR-155 | hsa-miR-26a | hsa-miR-379* | hsa-miR-520a-3p |
| hsa-miR-155* | hsa-miR-26a-1* | hsa-miR-380 | hsa-miR-520a-5p |
| hsa-miR-15a | hsa-miR-26a-2* | hsa-miR-380* | hsa-miR-520b |
| hsa-miR-15a* | hsa-miR-26b | hsa-miR-381 | hsa-miR-520c-3p |
| hsa-miR-15b | hsa-miR-26b* | hsa-miR-382 | hsa-miR-520d-3p |
| hsa-miR-15b* | hsa-miR-27a | hsa-miR-383 | hsa-miR-520d-5p |
| hsa-miR-16 | hsa-miR-27a* | hsa-miR-409-3p | hsa-miR-520e |

FIG. 18 D

| hsa-miR-16-1 * | hsa-miR-276 | hsa-miR-409-Sp | hsa-miR-520f |
|---|---|---|---|
| hsa-miR-16-2* | hsa-miR-276* | hsa-miR-410 | hsa-miR-520g |
| hsa-miR-17 | hsa-miR-28-3p | hsa-miR-411 | hsa-miR-520h |
| hsa-miR-17* | hsa-miR-28-Sp | hsa-miR-411 * | hsa-miR-521 |
| hsa-miR-181 a | hsa-miR-296-3p | hsa-miR-412 | hsa-miR-522 |
| hsa-miR-181a-2* | hsa-miR-296-Sp | hsa-miR-421 | hsa-miR-523 |
| hsa-miR-524-3p | hsa-miR-627 | hsa-miR-590-Sp | hsa-miR-885-Sp |
| hsa-miR-524-Sp | hsa-miR-628-3p | hsa-miR-591 | hsa-miR-886-3p |
| hsa-miR-525-3p | hsa-miR-628-Sp | hsa-miR-592 | hsa-miR-886-Sp |
| hsa-miR-525-Sp | hsa-miR-629 | hsa-miR-593 | hsa-miR-887 |
| hsa-miR-5266 | hsa-miR-629* | hsa-miR-593 * | hsa-miR-888 |
| hsa-miR-5266* | hsa-miR-630 | hsa-miR-595 | hsa-miR-888* |
| hsa-miR-527 | hsa-miR-631 | hsa-miR-596 | hsa-miR-889 |
| hsa-miR-532-3p | hsa-miR-632 | hsa-miR-597 | hsa-miR-890 |
| hsa-miR-532-Sp | hsa-miR-633 | hsa-miR-598 | hsa-miR-891a |
| hsa-miR-539 | hsa-miR-634 | hsa-miR-599 | hsa-miR-891b |
| hsa-miR-541 | hsa-miR-635 | hsa-miR-600 | hsa-miR-892a |
| hsa-miR-541 * | hsa-miR-636 | hsa-miR-601 | hsa-miR-8926 |
| hsa-miR-542-3p | hsa-miR-637 | hsa-miR-602 | hsa-miR-9 |
| hsa-miR-542-Sp | hsa-miR-638 | hsa-miR-603 | hsa-miR-9* |
| hsa-miR-543 | hsa-miR-639 | hsa-miR-604 | hsa-miR-920 |
| hsa-miR-544 | hsa-miR-640 | hsa-miR-605 | hsa-miR-921 |
| hsa-miR-545 | hsa-miR-641 | hsa-miR-606 | hsa-miR-922 |
| hsa-miR-545* | hsa-miR-642 | hsa-miR-607 | hsa-miR-923 |
| hsa-miR-548a-3p | hsa-miR-643 | hsa-miR-608 | hsa-miR-924 |
| hsa-miR-548a-5p | hsa-miR-644 | hsa-miR-609 | hsa-miR-92a |
| hsa-miR-548b-3p | hsa-miR-645 | hsa-miR-610 | hsa-miR-92a-1 * |
| hsa-miR-5486-Sp | hsa-miR-646 | hsa-miR-611 | hsa-miR-92a-2* |
| hsa-miR-548c-3p | hsa-miR-647 | hsa-miR-612 | hsa-miR-926 |
| hsa-miR-548c-5p | hsa-miR-648 | hsa-miR-613 | hsa-miR-926* |
| hsa-miR-548d-3p | hsa-miR-649 | hsa-miR-614 | hsa-miR-93 |
| hsa-miR-548d-5p | hsa-miR-650 | hsa-miR-615-3p | hsa-miR-93* |
| hsa-miR-549 | hsa-miR-651 | hsa-miR-615-Sp | hsa-miR-933 |
| hsa-miR-550 | hsa-miR-652 | hsa-miR-616 | hsa-miR-934 |
| hsa-miR-550* | hsa-miR-653 | hsa-miR-616* | hsa-miR-935 |
| hsa-miR-551a | hsa-miR-654-3p | hsa-miR-617 | hsa-miR-936 |
| hsa-miR-5516 | hsa-miR-654-Sp | hsa-miR-618 | hsa-miR-937 |
| hsa-miR-551b* | hsa-miR-655 | hsa-miR-619 | hsa-miR-938 |
| hsa-miR-552 | hsa-miR-656 | hsa-miR-621 | hsa-miR-939 |
| hsa-miR-553 | hsa-miR-657 | hsa-miR-622 | hsa-miR-940 |

FIG. 18 E

| | | | |
|---|---|---|---|
| hsa-miR-554 | hsa-miR-658 | hsa-miR-623 | hsa-miR-941 |
| hsa-miR-555 | hsa-miR-659 | hsa-miR-624 | hsa-miR-942 |
| hsa-miR-556-3p | hsa-miR-660 | hsa-miR-624* | hsa-miR-943 |
| hsa-miR-556-Sp | hsa-miR-661 | hsa-miR-625 | hsa-miR-944 |
| hsa-miR-557 | hsa-miR-662 | hsa-miR-625* | hsa-miR-95 |
| hsa-miR-558 | hsa-miR-663 | hsa-miR-626 | hsa-miR-96 |
| hsa-miR-559 | hsa-miR-665 | hsa-miR-765 | hsa-miR-96* |
| hsa-miR-561 | hsa-miR-668 | hsa-miR-766 | hsa-miR-98 |
| hsa-miR-562 | hsa-miR-671-3p | hsa-miR-767-3p | hsa-miR-99a |
| hsa-miR-563 | hsa-miR-671-Sp | hsa-miR-767-Sp | hsa-miR-99a* |
| hsa-miR-564 | hsa-miR-675 | hsa-miR-768-3p | hsa-miR-996 |
| hsa-miR-566 | hsa-miR-7 | hsa-miR-768-Sp | hsa-miR-996* |
| hsa-miR-567 | hsa-miR-7-1 * | hsa-miR-769-3p | hsa-miR-579 |
| hsa-miR-568 | hsa-miR-7-2* | hsa-miR-769-Sp | hsa-miR-580 |
| hsa-miR-569 | hsa-miR-708 | hsa-miR-770-Sp | hsa-miR-581 |
| hsa-miR-570 | hsa-miR-708* | hsa-miR-801 | hsa-miR-582-3p |
| hsa-miR-571 | hsa-miR-744 | hsa-miR-802 | hsa-miR-582-Sp |
| hsa-miR-572 | hsa-miR-744* | hsa-miR-873 | hsa-miR-583 |
| hsa-miR-573 | hsa-miR-758 | hsa-miR-874 | hsa-miR-584 |
| hsa-miR-574-3p | hsa-miR-760 | hsa-miR-875-3p | hsa-miR-590-3p |
| hsa-miR-574-Sp | hsa-miR-585 | hsa-miR-875-Sp | |
| hsa-miR-575 | hsa-miR-586 | hsa-miR-876-3p | |
| hsa-miR-576-3p | hsa-miR-587 | hsa-miR-876-Sp | |
| hsa-miR-576-Sp | hsa-miR-588 | hsa-miR-877 | |
| hsa-miR-577 | hsa-miR-589 | hsa-miR-877* | |
| hsa-miR-578 | hsa-miR-589* | hsa-miR-885-3p | |

TABLE 5

FIG. 19 A

| microRNAs from Table 5 with a computed multiple-hypothesis-corrected p-value (i.e. q-value) below 5% in differentiating between Evs of different cell types of origin | q-value (%) statistical significance in differentiating between EVs from three different cell types |
|---|---|
| hsa-miR-335 | 0 |
| hsa-miR-17 | 0 |
| hsa-miR-25 | 0 |
| hsa-miR-363 | 0 |
| hsa-miR-146b-5p | 0 |
| hsa-miR-20a | 0 |
| hsa-miR-320 | 0 |
| hsa-miR-513b | 0 |
| hsa-miR-21 | 0 |
| hsa-miR-20b | 0 |
| hsa-miR-30b | 0 |
| hsa-miR-193b | 0 |
| hsa-miR-342-3p | 0 |
| hsa-miR-221 | 0 |
| hsa-miR-1224-5p | 0 |
| hsa-miR-93 | 0 |
| hsa-miR-132 | 0 |
| hsa-miR-29a | 0 |
| hsa-miR-92a | 0 |
| hsa-miR-29c | 0 |
| hsa-miR-23a | 0 |
| hsa-miR-19a | 0 |
| hsa-miR-365 | 1.107851072 |
| hsa-miR-210 | 1.107851072 |
| hsa-miR-155 | 1.107851072 |
| hsa-miR-767-5p | 1.107851072 |
| hsa-miR-181a | 1.107851072 |
| hsa-miR-631 | 1.107851072 |
| hsa-miR-223 | 1.107851072 |
| hsa-miR-146a* | 1.107851072 |
| hsa-miR-146a | 1.107851072 |

FIG. 19 B

| | |
|---|---|
| hsa-miR-519d | 1.772561716 |
| hsa-miR-22 | 1.772561716 |
| hsa-miR-299-5p | 1.772561716 |
| hsa-miR-617 | 1.772561716 |
| hsa-miR-148a | 1.772561716 |
| hsa-miR-609 | 2.532231023 |
| hsa-miR-633 | 2.532231023 |
| hsa-miR-128 | 2.532231023 |
| hsa-miR-409-3p | 2.532231023 |
| hsa-miR-24 | 2.532231023 |
| hsa-miR-106b | 2.532231023 |
| hsa-miR-671-3p | 2.532231023 |
| hsa-miR-767-3p | 2.532231023 |
| hsa-miR-197 | 2.532231023 |
| hsa-miR-513c | 2.532231023 |
| hsa-miR-623 | 2.532231023 |
| hsa-miR-130b | 2.532231023 |
| hsa-miR-19b | 2.532231023 |
| hsa-miR-625* | 2.532231023 |
| hsa-miR-129* | 2.532231023 |
| hsa-miR-1227 | 2.532231023 |
| hsa-miR-18b* | 2.532231023 |
| hsa-miR-654-5p | 2.532231023 |
| hsa-miR-133a | 2.532231023 |
| hsa-miR-933 | 2.532231023 |
| hsa-miR-181b | 2.532231023 |
| hsa-miR-15b | 3.703860302 |
| hsa-miR-579 | 3.703860302 |
| hsa-miR-188-5p | 3.703860302 |
| hsa-miR-92b | 3.703860302 |
| hsa-miR-29b | 3.703860302 |
| hsa-miR-135a* | 3.703860302 |
| hsa-miR-574-3p | 3.703860302 |
| hsa-miR-494 | 3.703860302 |
| hsa-miR-636 | 3.703860302 |
| hsa-miR-181a-2* | 3.703860302 |
| hsa-miR-483-3p | 3.703860302 |
| hsa-miR-483-5p | 3.703860302 |
| hsa-miR-597 | 3.703860302 |
| hsa-miR-937 | 3.703860302 |
| hsa-miR-943 | 3.703860302 |
| hsa-miR-602 | 3.703860302 |

FIG. 19 C

| hsa-miR-129-3p | 3.703860302 |
|---|---|
| hsa-miR-27a | 3.703860302 |
| hsa-miR-30c | 4.002558713 |
| hsa-miR-211 | 4.002558713 |
| hsa-miR-1229 | 4.002558713 |
| hsa-miR-125a-3p | 4.002558713 |
| hsa-miR-101 | 4.002558713 |
| hsa-miR-559 | 4.002558713 |
| hsa-miR-346 | 4.002558713 |
| hsa-miR-563 | 4.002558713 |
| hsa-miR-484 | 4.002558713 |
| hsa-miR-331-3p | 4.002558713 |
| hsa-miR-150 | 4.002558713 |
| hsa-miR-378 | 4.002558713 |
| hsa-miR-513a-5p | 4.002558713 |
| hsa-miR-610 | 4.002558713 |
| hsa-miR-220b | 4.002558713 |
| hsa-miR-125b-2* | 4.002558713 |
| hsa-miR-26b | 4.002558713 |
| hsa-miR-411 * | 4.002558713 |
| hsa-miR-550 | 4.002558713 |
| hsa-miR-1233 | 4.002558713 |
| hsa-miR-606 | 4.002558713 |
| hsa-miR-422a | 4.002558713 |
| hsa-miR-149 | 4.002558713 |
| hsa-miR-324-3p | 4.002558713 |
| hsa-miR-181d | 4.002558713 |
| hsa-miR-33b* | 4.002558713 |
| hsa-miR-520g | 4.002558713 |
| hsa-miR-1234 | 4.002558713 |
| hsa-miR-425 | 4.002558713 |
| hsa-miR-634 | 4.002558713 |

FIG. 20

TABLE 6

| Predicted fractions of cell types present in each sample using EV RNA expression and all genes in orginal processed immune-cell derived EV matrix as features on single cell-of-origin real test EV samples | | | |
|---|---|---|---|
| EV Test Sample 1 | CD4+ T cell | B cell | Dendritic cell |
| Predicted fraction | 0.6887984 | 0.3112016 | 0 |
| True fraction | 1 | 0 | 0 |
| EV Test Sample 2 | CD4+ T cell | B cell | Dendritic cell |
| Predicted fraction | 0.7564762 | 0.05141965 | 0.1921042 |
| True fraction | 1 | 0 | 0 |
| EV Test Sample 3 | CD4+ T cell | B cell | Dendritic cell |
| Predicted fraction | 0.02348653 | 0.9765135 | 0 |
| True fraction | 0 | 1 | 0 |
| EV Test Sample 4 | CD4+ T cell | B cell | Dendritic cell |
| Predicted fraction | 0.1131806 | 0.8868194 | 0 |
| True fraction | 0 | 1 | 0 |
| EV Test Sample 5 | CD4+ T cell | B cell | Dendritic cell |
| Predicted fraction | 0.02638993 | 0.06355083 | 0.9100592 |
| True fraction | 0 | 0 | 1 |

FIG. 21

TABLE 7

Predicted fractions of cell types present in each sample using immune cell-derived EV RNA expression and 'cell-derived' feature set on single cell-of-origin real test EV samples

| EV Test Sample 1 | CD4+ T cell | B cell | Dendritic cell |
|---|---|---|---|
| Predicted fraction | 0.5064131 | 0.4935869 | 0 |
| True fraction | 1 | 0 | 0 |
| EV Test Sample 2 | CD4+ T cell | B cell | Dendritic cell |
| Predicted fraction | 0.6559934 | 0.2497047 | 0.09430187 |
| True fraction | 1 | 0 | 0 |
| EV Test Sample 3 | CD4+ T cell | B cell | Dendritic cell |
| Predicted fraction | 0.1195254 | 0.8804746 | 0 |
| True fraction | 0 | 1 | 0 |
| EV Test Sample 4 | CD4+ T cell | B cell | Dendritic cell |
| Predicted fraction | 0.4939658 | 0.5060342 | 0 |
| True fraction | 0 | 1 | 1 |
| EV Test Sample 5 | CD4+ T cell | B cell | Dendritic cell |
| Predicted fraction | 0 | 0.2120643 | 0.7879357 |
| True fraction | 0 | 0 | 1 |

FIG. 22

TABLE 8

| Predicted fractions of cell types present in each sample using immune cell-derived EV RNA expression and 'EV-derived' feature set on single cell-of-origin real test EV samples | | | |
|---|---|---|---|
| EV Test Sample 1 | CD4+ T cell | B cell | Dendritic cell |
| Predicted fraction | 0.8176157 | 0.1823843 | 0 |
| True fraction | 1 | 0 | 0 |
| EV Test Sample 2 | CD4+ T cell | B cell | Dendritic cell |
| Predicted fraction | 0.7806406 | 0.1429828 | 0.07637661 |
| True fraction | 1 | 0 | 0 |
| EV Test Sample 3 | CD4+ T cell | B cell | Dendritic cell |
| Predicted fraction | 0 | 1 | 0 |
| True fraction | 0 | 1 | 0 |
| EV Test Sample 4 | CD4+ T cell | B cell | Dendritic cell |
| Predicted fraction | 0.05231074 | 0.9476893 | 0 |
| True fraction | 0 | 1 | 1 |
| EV Test Sample 5 | CD4+ T cell | B cell | Dendritic cell |
| Predicted fraction | 0.09472321 | 0 | 0.9052768 |
| True fraction | 0 | 0 | 1 |

FIG. 23

TABLE 9

Predicted fractions of cell types present in each sample using cell RNA expression and all genes in orginal processed immune-ce;ll derived cell matrix as features on single cell-of-origin real test EV samples

| EV Test Sample 1 | CD4+ T cell | B cell | Dendritic cell |
|---|---|---|---|
| Predicted fraction | 0.9327392 | 0.02085855 | 0.04640227 |
| True fraction | I | 0 | 0 |
| EV Test Sample 2 | CD4+ T cell | B cell | Dendritic cell |
| Predicted fraction | 0.9043382 | 0.03444285 | 0.06121893 |
| True fraction | I | 0 | 0 |
| EV Test Sample 3 | CD4+ T cell | B cell | Dendritic cell |
| Predicted fraction | 0 | 0.9249077 | 0.07509227 |
| True fraction | 0 | I | 0 |
| EV Test Sample 4 | CD4+ T cell | B cell | Dendritic cell |
| Predicted fraction | 0 | 0.9435919 | 0.05640808 |
| True fraction | 0 | I | I |
| EV Test Sample 5 | CD4+ T cell | B cell | Dendritic cell |
| Predicted fraction | 0.03061606 | 0.01910185 | 0.9502821 |
| True fraction | 0 | 0 | I |

FIG. 24

TABLE 10

| Predicted fractions of cell types present in each sample using cell RNA expression and 'cell-derived' feature set on single cell-of-origin real test cell samples | | | |
|---|---|---|---|
| EV Test Sample 1 | CD4+ T cell | B cell | Dendritic cell |
| Predicted fraction | 0.617766 | 0.1262653 | 0.2559687 |
| True fraction | 1 | 0 | 0 |
| EV Test Sample 2 | CD4+ T cell | B cell | Dendritic cell |
| Predicted fraction | 0.54127 | 0.2024499 | 0.2562801 |
| True fraction | 1 | 0 | 0 |
| EV Test Sample 3 | CD4+ T cell | B cell | Dendritic cell |
| Predicted fraction | 0 | 0.9039272 | 0.09607278 |
| True fraction | 0 | 1 | 0 |
| EV Test Sample 4 | CD4+ T cell | B cell | Dendritic cell |
| Predicted fraction | 0 | 0.9017485 | 0.09825155 |
| True fraction | 0 | 1 | 1 |
| EV Test Sample 5 | CD4+ T cell | B cell | Dendritic cell |
| Predicted fraction | 0.02156448 | 8.27E-05 | 0.9783528 |
| True fraction | 0 | 0 | 1 |

FIG. 25

TABLE 11

| Predicted fractions of cell types present in each sample using cell RNA expression and 'EV-derived' feature set on single cell-of-origin real test cell samples |||| 
|---|---|---|---|
| EV Test Sample 1 | CD4+ T cell | B cell | Dendritic cell |
| Predicted fraction | 0.8598371 | 0.03876011 | 0.1014028 |
| True fraction | 1 | 0 | 0 |
| EV Test Sample 2 | CD4+ T cell | B cell | Dendritic cell |
| Predicted fraction | 0.8552683 | 0.1292242 | 0.01550745 |
| True fraction | 1 | 0 | 0 |
| EV Test Sample 3 | CD4+ T cell | B cell | Dendritic cell |
| Predicted fraction | 0 | 0.9931649 | 0.006835112 |
| True fraction | 0 | 1 | 0 |
| EV Test Sample 4 | CD4+ T cell | B cell | Dendritic cell |
| Predicted fraction | 0 | 0.9872461 | 0.0127539 |
| True fraction | 0 | 1 | 1 |
| EV Test Sample 5 | CD4+ T cell | B cell | Dendritic cell |
| Predicted fraction | 0.04446984 | 0 | 0.9555302 |
| True fraction | 0 | 0 | 1 |

FIG 26A

TABLE 12

Predicted fractions of cell types present in simulated samples with mixed known fractions of different cell types using 'EV-derived' gene feature set on RNA expression from EVs or cells (two separate model fits)

| Truth or Prediction | Fraction T cell | Fraction B cell | Fraction Dendritic cell |
|---|---|---|---|
| Simulated cell fraction 'truth' sample 1 | 1 | 0 | 0 |
| EV-based prediction | 0.817615655 | 0.182384345 | 0 |
| Cell-based prediction | 0.859837129 | 0.038760107 | 0.101402764 |
| Simulated cell fraction 'truth' sample 2 | 0 | 1 | 0 |
| EV-based prediction | 0 | 1 | 0 |
| Cell-based prediction | 0 | 0.987246095 | 0.012753905 |
| Simulated cell fraction 'truth' sample 3 | 0 | 0 | 1 |
| EV-based prediction | 0.094723208 | 0 | 0.905276792 |
| Cell-based prediction | 0.044469845 | 0 | 0.955530155 |
| Simulated cell fraction 'truth' sample 4 | 0.9 | 0.1 | 0 |
| EV-based prediction | 0.671854895 | 0.273048456 | 0.05509665 |
| Cell-based prediction | 0.749870858 | 0.229128825 | 0.021000317 |
| Simulated cell fraction 'truth' sample 5 | 0.1 | 0.9 | 0 |
| EV-based prediction | 0 | 1 | 0 |
| Cell-based prediction | 0 | 0.98342909 | 0.01657091 |
| Simulated cell fraction 'truth' sample 6 | 0 | 0.1 | 0.9 |
| EV-based prediction | 0.096078128 | 0.083816355 | 0.82105516 |
| Cell-based prediction | 0.03100219 | 0.09917078 | 0.86982703 |
| Simulated cell fraction 'truth' sample 7 | 0.6 | 0.2 | 0.2 |
| EV-based prediction | 0.44146624 | 0.305079699 | 0.253454061 |
| Cell-based prediction | 0.51425686 | 0.275020807 | 0.210722333 |

FIG 26B

TABLE 12 CONTINUED

| Truth or Prediction | Fraction T cell | Fraction B cell | Fraction Dendritic cell |
|---|---|---|---|
| Simulated cell fraction 'truth' sample 8 | 0.2 | 0.6 | 0.2 |
| EV-based prediction | 0.191627299 | 0.633680421 | 0.174692281 |
| Cell-based prediction | 0.137833961 | 0.642547294 | 0.219618745 |
| Simulated cell fraction 'truth' sample 9 | 0.2 | 0.2 | 0.6 |
| EV-based prediction | 0.225277228 | 0.182520408 | 0.592202363 |
| Cell-based prediction | 0.189544872 | 0.214146267 | 0.596308861 |
| Simulated cell fraction 'truth' sample 10 | 0.3 | 0.3 | 0.3 |
| EV-based prediction | 0.297224096 | 0.3347504 | 0.368025504 |
| Cell-based prediction | 0.293365502 | 0.37759719 | 0.329037309 |

SYSTEMS AND METHODS FOR CHARACTERIZING EXTRACELLULAR VESICLE (EV) POPULATION BY PREDICTING WHETHER THE EV ORIGINATES FROM B, T, OR DENDRITIC CELLS

CROSS-REFERENCE TO RELATED APPLICATIONS

This application claims the benefit of U.S. Provisional Application No. 62/443,540, entitled "Systems and Methods for Algorithmic Extracellular Vesicle Population Discovery and Characterization," filed on Jan. 6, 2017, which is incorporated by reference herein in its entirety for all purposes.

TECHNICAL FIELD

The disclosed embodiments relate generally to biofluidic systems.

INTRODUCTION

Extracellular vesicles (EVs) are a class of membrane bound organelles secreted by various cell types. EVs are abundant in various biological fluids and cell culture, including but not limited to blood, urine, saliva, cerebrospinal fluid, breast milk, synovial, amniotic, and lymph fluids. EVs are also secreted by cells when cultured in vitro. In addition, EVs are stable carriers of enriched genetic material such as deoxyribonucleic acid (DNA) or ribonucleic acid (RNA), proteins and lipids and are significant mediators of intercellular communication.

The characteristics of EVs such as vesicle size, vesicle density, vesicle lipid bilayer composition, extravesicular proteins or genetic material attached to the vesicles, extravesicular proteins or genetic material floating in surrounding biological sample, vesicle membrane proteins, intravesicular proteins, intravesicular genetic material, biochemical alterations of extravesicular or intravesicular genetic material, or any combinations thereof, can differ by the state of each EV or a group of EVs. Possible states include, but are not limited to, the type of cell secreting the EVs, the disease state of the host animal or cell culture conditions from which the EVs are secreted, the type of biofluid containing the cells or EVs, or the type of organ from which the cells secreting EVs reside.

An extracellular vesicle population is defined by EVs that share a set of common characteristics caused by, related to, correlated with or anti-correlated with a specific set of state or states. A single EV can be included in multiple EV population groupings.

EV populations, defined by EV characteristics, which may differ by state, can be used not only as biomarkers but as targeted therapeutic compound delivery vehicles. The ability to detect EVs in various animal biological fluids has been shown to correlate well with the organ or cell-of-origin of the EV and animal disease status, disease progression, immune response, and toxicity. EVs populations known to be correlated with a specific state have been proposed and tested as therapeutic compounds in animal models and human clinical trials to treat diseases such as cancer.

SUMMARY

Methods and systems for extracellular vesicle characterization are provided herein. Embodiments of the methods include inputting measured physical, biological, or chemical aspects of extracted extracellular vesicles. Next, an information architecture that characterizes relationships between biological entities and diseases in humans or other vertebrates is generated. Then, relationships between the measured physical, biological, or chemical aspects of the isolated extracellular vesicles with the information architecture are automatically inferred, thereby characterizing extracellular vesicles.

In various aspects, the measured aspects of the extracellular vesicles include: vesicle size, vesicle density, vesicle lipid bilayer composition, extravesicular proteins or genetic material attached to the vesicles, extravesicular proteins or genetic material floating in surrounding biological sample, vesicle membrane proteins, intravesicular proteins, intravesicular genetic material, biochemical alterations of extravesicular or intravesicular genetic material, or any combinations thereof.

In some versions, the information architecture stores relationships and attributes of biological entities or diseases as a relational database, a non-relational database, a graph database, lists of attributes in flat files, or any combination of such databases. In various aspects, the relationships between biological entities, diseases, or attributes of the entities or diseases stored in the information architecture contain different values for different states. In various instances, the measured aspects of the extracellular vesicles are interpreted to have potential relationships amongst themselves. In some circumstances, relationships between measurement aspects of the extracellular vesicles are represented via a binary decision, thresholding, covariance, variance, distance metrics, or any combination thereof.

Embodiments of the methods also include comparing the relationships between measurement aspects of the extracellular vesicles, values of the measured aspects between extracellular vesicles, one or more lists of key measured aspects in extracellular vesicles, or any combinations thereof, with the relationships or attributes of biological entities or diseases stored in the information architecture.

Methods can further include providing recommendations for diagnosis of diseases, treatment of diseases, potential biochemical compounds that may act as pharmaceutical agents, EVs that can act as promising pharmaceutical agent delivery vehicles, or any other clinical conditions for human or vertebrate healthcare. Providing such recommendations can include quantifying a similarity measurement and determining whether the similarity measurement exceeds a predetermined threshold. Providing such recommendations can also include presenting the user the EV characteristics whose correlation with a specific state is concordant between different EV sources, such as in vitro cell culture models and human patient blood samples. This system in effect provides recommends on the ideal EV population for use in the diagnosis of diseases, treatment of diseases, potential biochemical compounds that may act as pharmaceutical agents, EVs that can act as promising pharmaceutical agent delivery vehicles, or any other clinical conditions for human or vertebrate healthcare.

Also in some instances, additional information is linked to the origin of the biological sample, such as medical history, additional measurements from the biological sample, disease status or therapies administered and is incorporated to improve the accuracy of the recommendations.

Some aspects of the present disclosure include systems for extracellular vesicle characterization. Such systems can include a processor device, such as a computer processor that: receives an input including measured physical, biological, or chemical aspects of extracellular vesicles extracted from a biological sample; generates an information architecture that characterizes relationships between biological entities and diseases in humans or other vertebrates; and/or automatically, such as without further human interaction, infers relationships between the measured physical, biological, or chemical aspects of the extracted extracellular vesicles with the information architecture.

In some aspects, measured aspects of the extracellular vesicles include: vesicle size, vesicle density, vesicle lipid bilayer composition, extravesicular proteins or genetic material attached to the vesicles, extravesicular proteins or genetic material floating in surrounding biological sample, vesicle membrane proteins, intravesicular proteins, intravesicular genetic material, and biochemical alterations of any extravesicular or intravesicular genetic material, or any combinations thereof.

In various instances, the information architecture stores relationships and attributes of biological entities or diseases as a relational database, a non-relational database, a graph database, lists of attributes in flat files, or any combination of such databases. Relationships between biological entities, diseases, or attributes of the entities or diseases which are stored in the information architecture can contain different values for different states.

In some versions, the measured aspects of the extracellular vesicles are interpreted to have potential relationships amongst themselves. Relationships between measurement aspects of the extracellular vesicles can be represented via a binary decision, thresholding, covariance, variance, distance metrics, or any combination thereof.

In some aspects, the embodiments include comparing the relationships between measurement aspects of the extracellular vesicles, values of the measured aspects between extracellular vesicles, one or more lists of key measured aspects in extracellular vesicles, or any combinations thereof, with the relationships or attributes of biological entities or diseases stored in the information architecture.

The embodiments also include providing recommendations, e.g., automatically providing recommendations, for EVs that can act as targeted pharmaceutical agent delivery vehicles for specific states, for the ideal combination of EV characteristics that would result in an EV that that can act as targeted pharmaceutical agent delivery vehicles for specific states, potential biochemical compounds that may act as pharmaceutical agents, for diagnosis of diseases, treatment of diseases, or any other clinical conditions for human or vertebrate healthcare. Providing recommendations can include quantifying a similarity measurement and determining whether the similarity measurement exceeds a predetermined threshold. Such providing can be done entirely by the computer processor without human interaction after the initial input is made. Providing such recommendations can also include presenting the user the EV characteristics whose correlation with a specific state is concordant between different EV sources, such as in vitro cell culture models and human patient blood samples. In various instances, additional information linked to the origin of the biological sample, such as medical history, additional measurements from the biological sample, disease status or therapies administered, is incorporated to improve the accuracy of the recommendations.

The methods further include methods for extracellular vesicle characterization including steps of: obtaining extracellular vesicle-characteristic data; generating an information architecture that characterizes relationships between biological entities and diseases in humans or other vertebrates; and/or automatically inferring relationships between the extracellular vesicle-characteristic data of the extracted extracellular vesicles with the information architecture and thereby characterizing the extracellular vesicles.

Extracellular vesicle-characteristic data can include data of vesicle size, vesicle density, vesicle lipid bilayer composition, extravesicular proteins or genetic material attached to the vesicles or, extravesicular proteins or genetic material floating in the surrounding biological sample, vesicle membrane proteins, intravesicular proteins, intravesicular genetic material, or biochemical alterations of extravesicular or intravesicular genetic material, or any combinations thereof. Extracellular vesicles according to the subject aspects can be exosomes and/or nanosomes. Diseases according to the subject aspects can cancer and the extracellular vesicles can be characterized as tumor extracellular vesicles.

In various instances, the measuring includes performing DNA-seq methylation, DNA array methylation expression, DNA-seq somatic mutation expression, DNA array somatic mutation expression, DNA-seq germline mutation expression, DNA array germline mutation expression, DNA ChIp-Seq expression, RNA-seq expression, RNA microarray expression, single-cell RNA-seq expression, single-EV RNA-seq expression, fluorescence imaging and fluorescent tag quantification, nanoparticle tracking analysis (NTA) measurements, EV count measurements, EV size, flow cytometry, mass spectrometry, mass cytometry, protein western blot, enzyme-linked immunosorbent assay (ELISA), and/or single-photon emission computed tomography (SPECT), immunohistochemistry, resistive pulsing, size exclusion chromatography, zeta potential analysis, protein microarrays, or any combination thereof, to for example, thereby obtain characteristic data of the extracted extracellular vesicles. These measurements can be applied to a group of EVs, or done at the single vesicle level, such as single-vesicle proteomics or single-vesicle RNA-seq. They can also be applied to a group of cells or done at the single-cell level, and combined with measurements applied to a group of EVs or individual EVs, to improve recommendations of the system on what EV populations are related to certain cell populations.

In some aspects, public or private data concerning cell and organ specificity is included in the information architecture to aide in automatic predictions of which EVs will specifically be engulfed or interact with certain cells or organs.

In some aspects, automatically inferring includes comparing characteristic data of the extracted extracellular vesicles with previously categorized extracellular vesicle characteristic data stored in a database or databases to thereby characterize the new extracellular vesicles being inputted into the automatic prediction system to predict their utility as pharmaceutical agent delivery vehicles, pharmaceutical compounds, or biomarkers for different states. In some aspects, previously categorized extracellular vesicle characteristic data includes extracellular vesicle characteristic identifiers.

Aspects of the subject embodiments can include an extracellular vesicle isolating device for extracting extracellular vesicles from a biological sample. Embodiments can also include an extracellular vesicle characteristic measuring device for measuring physical, biological, or chemical aspects of extracted extracellular vesicles. Also, in some versions, the processing device produces an output of the automatically inferred relationships.

BRIEF DESCRIPTION OF THE DRAWINGS AND TABLES

These and other aspects and features of the present disclosure will become apparent to those ordinarily skilled in the art upon review of the following description of specific embodiments of the present disclosure in conjunction with the accompanying figures, wherein:

FIG. 1 provides one example of a system for extracellular vesicle characterization, according to various embodiments of the present disclosure.

FIG. 2 provides a box diagram showing an example workflow for building a deconvolution algorithm, according to various embodiments of the present disclosure.

FIG. 3 provides an example of a method for extracellular vesicle characterization, in accordance with one or more embodiments.

FIG. 4 provides one example of a system that can be used in conjunction with the techniques and mechanisms of the present disclosure in accordance with one or more embodiments.

FIG. 5 provides one example of a system that can be used in conjunction with the techniques and mechanisms of the present disclosure in accordance with one or more embodiments. FIGS. 6-7 provide supporting figures for this example.

FIG. 6 provides an illustration of microRNA deconvolution results on EV microRNA data according to the subject embodiments.

FIG. 7 provides a schematic illustration of a clustering analysis of RNA from isolated extracellular vesicles according to the subject embodiments.

FIG. 8 provides one example of a system that can be used in conjunction with the techniques and mechanisms of the present disclosure in accordance with one or more embodiments. FIGS. 8-12 provide supporting figures for this example according to the subject embodiments.

Figure 11:
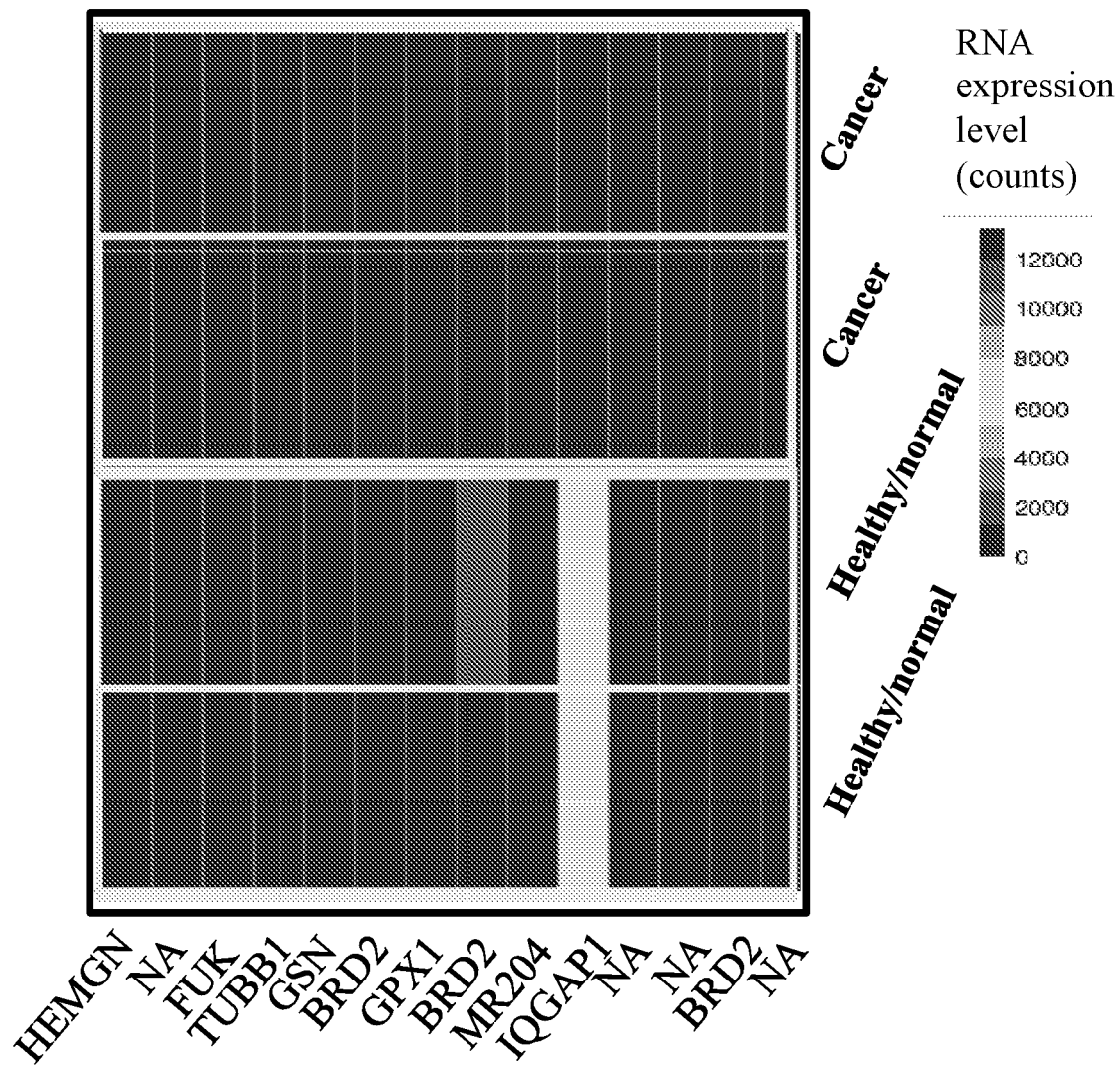

FIG. 11 a clustering analysis of EV RNA expression from in vitro cell culture from normal epithelial and from lung cancer cell cultures according to the subject embodiments.

Figure 8:
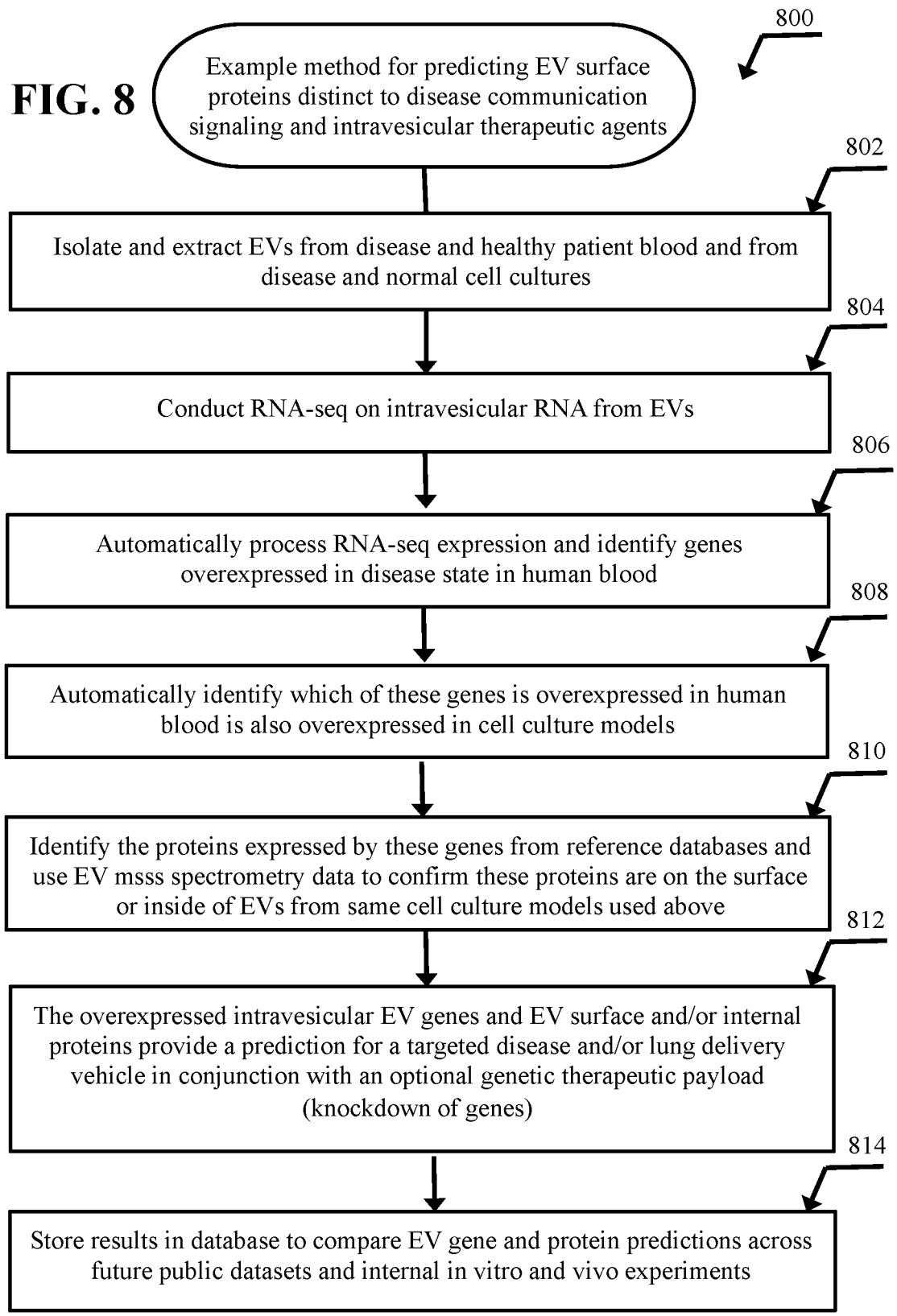
Figure 12:
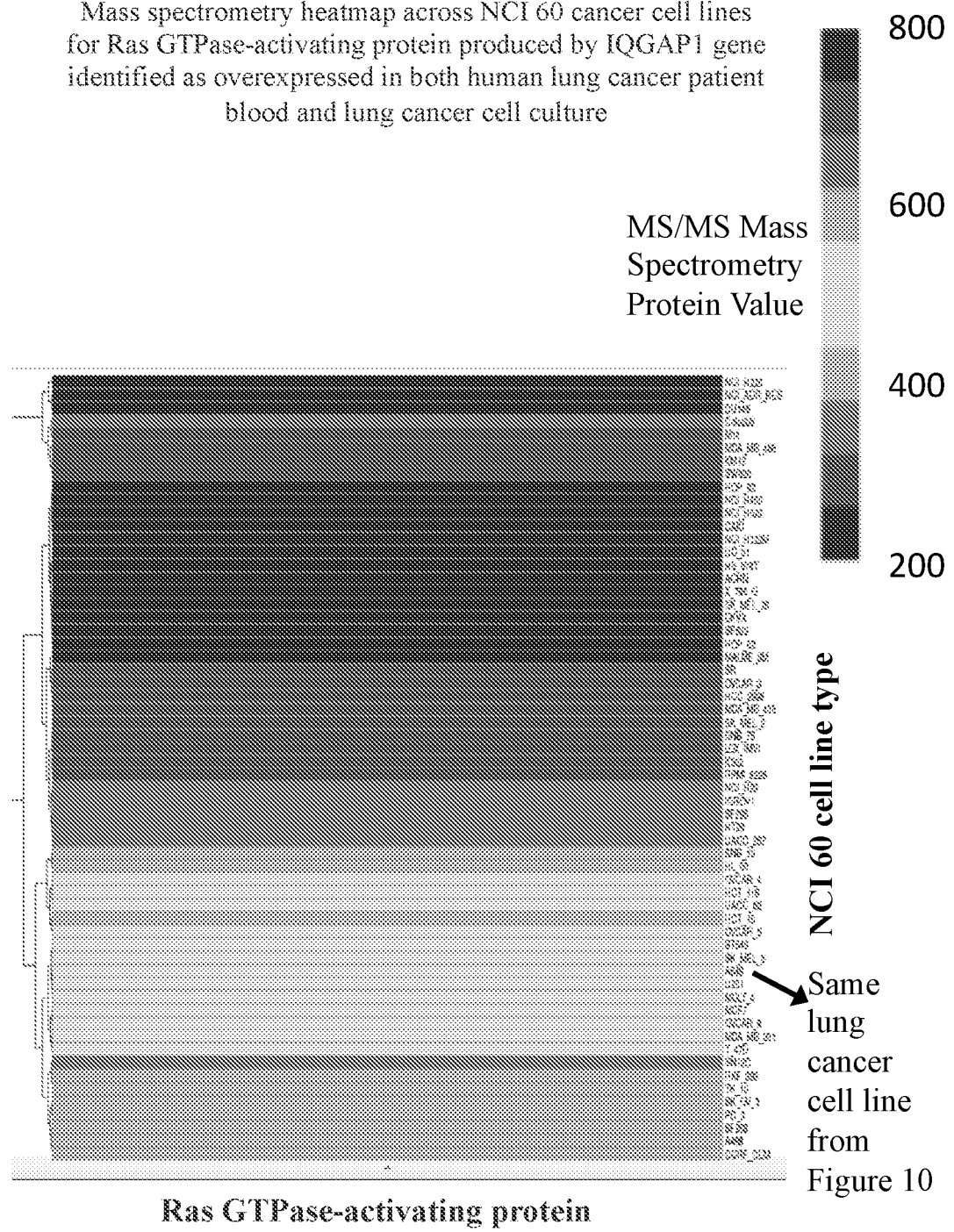

FIG. 12 is a mass spectrometry heatmap of a specific EV protein recommended by the system implementation in FIG. 8 across various cell line cultures from different organs according to the subject embodiments.

Figure 13:
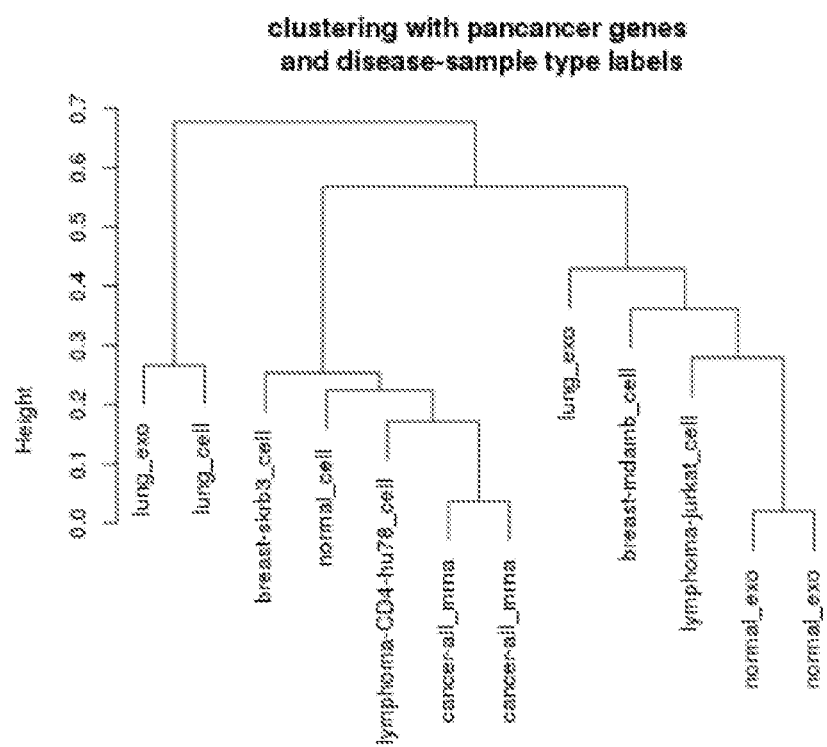

FIG. 13 provides a schematic illustration of clustering analyses of RNA from cells and from isolated extracellular vesicles using a list of cancer cell-related genes according to the subject embodiments.

Figure 14:
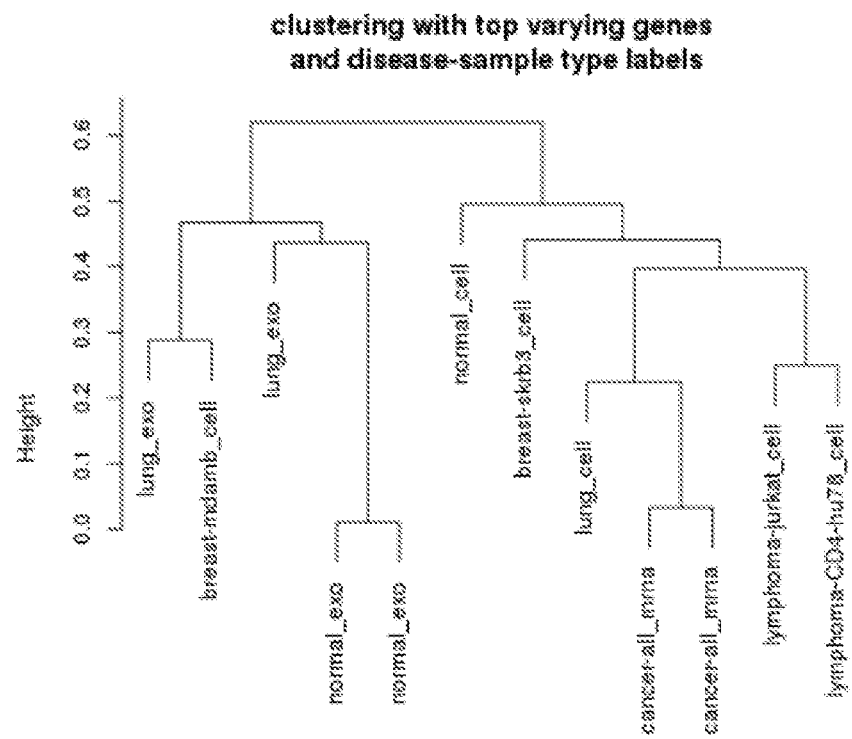

FIG. 14 provides a schematic illustration of clustering analyses of RNA from cells and from isolated extracellular vesicles using a de novo, automatically defined list of genes recommended by the system according to the subject embodiments.

FIG. 15: Table 1 is a gene signature list consisting of mRNAs (i.e. RNAs that directly transcribe proteins) that differentially distinguish between different cell types, in this case, immune cells. For example, CD4 in this list is related to CD4+ regulatory T cells.

FIG. 16: Table 2 is a list of microRNAs automatically predicted to regulate the mRNAs in Table 1 according to the subject embodiments. See Example 1 for details on how Tables 2-12 were automatically generated the example system architecture and algorithms presented in FIG. 5.

FIG. 17: Table 3 is a list of microRNA symbols found in both Table 1 and an EV microRNA expression matrix of EVs derived from known cell types according to the subject embodiments.

FIG. 18: Table 4 is a subset of the microRNA symbols in Table 2 after automated post-processing and feature set reduction according to the subject embodiments.

FIG. 19: Table 5 details results of microRNAs that distinguish EV populations from different cell types in an automated fashion according to the subject embodiments.

FIG. 20: Table 6 details results from the system implementation outlined in FIG. 5 predicting EV cell-of-origin from EV characteristics using all genes originally present in the data matrix referenced in Table 3 as a feature set according to the subject embodiments.

FIG. 21: Table 7 details the accuracy rates of automated predictions from the system implementation outlined in FIG. 5 predicting EV cell-of-origin from EV characteristics using as a gene feature set derived from cell-level characteristics according to the subject embodiments.

FIG. 22: Table 8 details the accuracy rates of automated predictions from the system implementation outlined in FIG. 5 predicting EV cell-of-origin from EV characteristics using as a gene feature set derived from EV-level characteristics according to the subject embodiments.

FIG. 23: Table 9 details the accuracy rates of automated predictions from the system implementation outlined in FIG. 5 predicting cell-type of cells from cell characteristics using all genes originally present in the data matrix referenced in Table 2 as a feature set according to the subject embodiments.

FIG. 24: Table 10 details the accuracy rates of automated predictions from the system implementation outlined in FIG. 5 predicting cell type of cells from cell characteristics using as a gene feature set derived from cell-level characteristics according to the subject embodiments.

FIG. 25: Table 11 details the accuracy rates of automated predictions from the system implementation outlined in FIG. 5 predicting cell type of cells from cell characteristics using as a gene feature set derived from EV-level characteristics according to the subject embodiments.

FIG. 26: Table 12 details the accuracy rates of automated predictions from the system implementation outlined in FIG. 5 predicting cell type of EVs, and cells from the corresponding cell type cultures, using EV or cell characteristics and a gene feature set derived from EV-level characteristics according to the subject embodiments. The EV and cell characteristic measurements used to create this table are simulated mixtures of measurements from known fractional mixtures of different cell types.

Like reference numerals refer to corresponding parts throughout the drawings.

DETAILED DESCRIPTION

Methods and systems for extracellular vesicle characterization are provided herein.

Embodiments of the methods include isolating and/or extracting extracellular vesicles from biological samples and/or measuring one or more physical, biological, or chemical aspects of the extracted extracellular vesicles. An information architecture can be generated that characterizes relationships between biological entities and diseases in humans or other vertebrates. Relationships between the measured physical, biological, or chemical aspects of the isolated extracellular vesicles with the information architecture can then be automatically inferred.

Before the present disclosure is described in greater detail, it is to be understood that this present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges and are also encompassed within the present disclosure, subject to any specifically excluded limit in the stated range. Where the stated range includes one or both of the limits, ranges excluding either or both of those included limits are also included in the present disclosure.

Certain ranges may be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this present disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

It will be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, without changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Reference will now be made in detail to various embodiments, examples of which are illustrated in the accompanying drawings. In the following detailed description, numerous specific details are set forth in order to provide a thorough understanding of the present disclosure and the described embodiments. However, the present disclosure may be practiced without these specific details. In other instances, well-known methods, procedures, components, and circuits have not been described in detail so as not to unnecessarily obscure aspects of the embodiments.

Extracellular vesicles (EVs) can be flexible, multi-purpose drug delivery vehicles because they are secreted and engulfed by cells. EVs known to be correlated with a specific state can be altered to contain therapeutic compounds not native to EVs. These EVs, once administered to an animal, can alter the biological state of the animal in a highly targeted manner because the EVs deliver the compound to cells involved in said state. EVs can also be re-engineered to alter their surface proteins or internal contents to mimic another EV of interest or to increase interactions with a specific cell or organ type.

EV populations, such as those found in biological fluids, can be characterized to understand which EVs may be appropriate for use as delivery vehicle compounds targeting a certain state or as targeted therapeutic compounds themselves. EV populations can also be used to diagnose a disease, prediction an optimal treatment regimen for a patient, or monitor the treatment response of a patient. Such characterization can be based on specific properties and attributes of particular EV populations.

EV populations, such as those found in biological fluids, can be characterized to understand which characteristics of EVs may be appropriate for use as delivery vehicle compounds targeting a certain biological state or as targeted therapeutic compounds themselves. These characteristics may or may not be present on a single naturally occurring EV, but these characteristics can be used to engineer an EV with these specific characteristics. Such characterization can be based on specific properties and attributes of particular EV populations.

Systems and Methods

Extracellular vesicles (EVs) are a class of membrane bound organelles secreted by various cell types. By "extracellular vesicle" as provided herein is meant a cell-derived vesicle having a membrane that surrounds and encloses a central internal space. Membranes of EVs can be composed of a lipid bi-layer having an external surface and an internal surface bounding an enclosed volume. As described further below, such membranes can have one or more types of cargo, such as proteins, embedded therein. EVs include all membrane-bound vesicles that have a cross-sectional diameter smaller than the cell from which they are secreted. EVs can have a longest dimension, such as a longest cross-sectional dimension, such as a cross-sectional diameter ranging from 10 nm to 1000 nm, such as 20 nm to 1000 nm, such as 30 nm to 1000 nm, such as 10 to 100 nm, such as 20 to 100 nm, such as 30 to 100 nm, such as 40 to 100 nm, such as 10 to 200 nm, such as 20 to 200 nm, such as 30 to 200 nm, such as 40 to 200 nm, such as 10 to 120 nm, such as 20 to 120 nm, such as 30 to 120 nm, such as 40 to 120 nm, such as 10 to 300 nm, such as 20 to 300 nm, such as 30 to 300 nm, such as 40 to 300 nm, such as 50 to 1000 nm, such as 500 to 2000 nm, such as 100 to 500 nm, such as 500 to 1000 nm and such as 40 nm to 500 nm, each range inclusive.

The term "membrane" as used in the subject disclosure, refers to a boundary layer separating an interior vesicle space from an exterior space, wherein the layer includes one or more biological molecules such as lipids, and in some instances, carbohydrates and/or polypeptides. Membranes can include lipids and/or fatty acids. Such lipids can include phospholipids, phosphatidylserine, sphingolipids, sterols, glycolipids, fatty acids, cholesterols, and/or phosphoglycerides. Membranes can also include one or more polypeptide and/or polysaccharide, e.g., glycan.

EVs include (i) extravesicles: 30-150 nanometer diameter membraneous vesicles of endocytic origin (ii) ectosomes (also referred to as shedding microvesicles, SMVs): large membranous vesicles (ranging, for example, from 50 nm to 5000 nm in diameter) that are shed directly from the cellular plasma membrane and (iii) apoptotic blebs (ranging, for example, from 50 nm to 5000 nm in diameter): released by dying cells.

EVs, particularly extravesicles, are important for intercellular communications within the human body and involved in many pathophysiological conditions such as Cancer or neurodegenerative disease. EVs are abundant in various patient biological samples, e.g., biological fluids, including but not limited to blood, urine, saliva, cerebrospinal fluid, breast milk, synovial, amniotic, and lymph fluids.

In various aspects, EVs include cell fragments. EVs are derived from, such as by being produced and released by producer donor cells. The term "producer cell," as used herein, refers to a cell from which an EV can be extracted or isolated. Producer cells are cells which act as a source for one or more EVs. Producer cells can share one or more component, such as a nucleic acid molecule, lipid, protein, lipid, and/or sugar component with derivative EVs. Producer cells can also be isolated and/or cultured cells. Producer cells can, in some aspects be modified or synthetic cells. Producer cells can be immune cells. In various instances a producer cell is a primary cell or a cell line.

As used in the subject disclosure, the terms "extracted," "extracting," "isolate," "isolated," "isolating," "purify," "purified," and "purifying," refer to a stage of a preparation of desired subject EVs, that have been subjected to one or more purification process, such as an enrichment and/or selection of the desired EV preparation. Also, a preparation of EVs can be a plurality of unknown or known amount and/or concentration. In various instances, purifying or isolating is the process of removing, such as partially removing or substantially removing, a portion (e.g. a fraction) of the EVs from a sample containing one or more biological components, such as producer cells. In various aspects, an EV composition that has been isolated is enriched as compared to the starting fraction, e.g., producer cell preparations), from which the EV composition is obtained. Such enrichment can, for example, be enrichment by 5%, 10%, 20%, 30%, 40%, 50%, 60%, 70%, 80%, 90%, 95%, 96%, 97%, 98%, 98.5%, 99%, 99.5%, 99.9%, 99.99%, 99.999%, 99.9999%, or 99.9999% or greater, as compared to the starting fraction. In some instances, an isolated EV sample has an amount and/or concentration of desired EVs at or above an acceptable concentration and/or amount. According to some versions, isolated EV preparations are free or substantially free of residual biological products. In some aspects, isolated EV preparations are 100% free, 99.5% free, 99% free, 98.5% free, 98% free, 97% free, 96% free, or 95% free, or 90% or greater free, of any contaminating biological matter such as producer cells. Undesired residual biological aspects can include unwanted nucleic acids, proteins, lipids, and/or or metabolites or abiotic materials such as including chemicals. The phrase substantially free of residual biological products can also mean that the EV composition contains no producer cells that are detectable and that only EVs in the composition are detectable. An isolated EV composition in various aspects, has no undesired activity that is detectable or, the level or amount of the detected undesired activity is at or below an acceptable level.

Also, the phrases "nucleic acid molecule," and "nucleic acid" as used herein refer to a double or single-stranded polymer of ribonucleotide or deoxyribonucleotide bases. A nucleic acid can be recombinant and peptides, e.g., exogenous polypeptides, can be expressed when the nucleic acid is introduced into a cell. Nucleic acids can, for example, include vectors, messenger RNA (mRNA), single stranded RNA that is complementary to an mRNA (antisense RNA), microRNA (mi RNA), tRNA, small interfering RNA (siRNA), small or short hairpin RNA (shRNA), long noncoding RNA (lncRNA), chromosomal DNA, e.g., double stranded DNA (dsDNA), and/or self-replicating plasmids.

EVs can also be derived from cells by manipulation, such as indirect or direct manipulation, e.g., by extrusion or application of alkaline solutions. EVs can include organelles separated into vesicles, and vesicles produced by living cells such as by fusion of a late endosome with the plasma membrane or direct plasma membrane budding. Furthermore, EVs can be derived from a dead or living organism, cultured cells, explanted tissues or organs, or any combination thereof.

In various aspects, EVs include a cargo including, for example, a receiver, or a targeting moiety for binding a target. A "receiver," as used herein, refers to a molecule that promotes the interaction, e.g., binding, of an EV with a target, and/or directs an EV to a target. A receiver can be a polypeptide and/or an antibody. As used herein, a "target" is a cell, a pathogen, a metabolite, a polypeptide complex, or any molecule or structure that resides in a tissue or circulates in the circulatory system or lymphatic system of the subject, such as an immune cell or a cancer cell. A target can be any of such aspects which readily interacts with, e.g., binds, a receiver.

EVs can also include a payload, e.g. a therapeutic agent, a sugar, e.g. a glycan, simple sugar, polysaccharide, a polynucleotide, e.g. a nucleic acid, DNA and/or RNA, other molecules, or any combination thereof. The term "payload" as applied herein refers to an agent, e.g., a therapeutic agent, that acts on a target, such as a cell, that is contacted with and/or bound to an EV. Further examples of payloads include amino acids such as amino acids having a detectable moiety or a toxin or that disrupt translation, polypeptides such as enzymes, nucleotides having a detectable moiety or a toxin or that disrupt transcription, nucleic acids that encode a polypeptide such as an enzyme, or RNA molecules that have regulatory function such as dsDNA, miRNA, siRNA, and lncRNA, small molecules such as small molecule toxins and drugs, lipids, and/or carbohydrates.

Also, as referred to in the subject disclosure, "therapeutic molecules," or "therapeutic agents," which are also referred to as "therapeutics," are molecules or compounds that when present in an effective amount, produce a desired therapeutic effect on a subject in need thereof. Such an effect can be physiologic and/or pharmacologic. Therapeutics include one or more compounds, for example, a small molecule drug, or a biologic, such as a polypeptide drug or a nucleic acid drug, that when administered to a subject has a conveyable and/or measurable effect on the subject. Such an effect can be that it treats, such as decreases or alleviates, one or more symptom of a condition, disease, or disorder.

EVs as provided herein include exosomes. By "exosome" is meant a cell-derived vesicle composed of a membrane enclosing an internal space, wherein the vesicle is generated from a cell by fusion of the late endosome with the plasma membrane or by direct plasma membrane budding, and wherein the vesicle has a longest dimension, such as a longest cross-sectional dimension, such as a cross-sectional diameter, ranging for example, from 10 nm to 150 nm, such as 20 nm to 150 nm, such as 20 nm to 130 nm, such as 20 nm to 120 nm, such as 20 to 100 nm, such as 40 to 130 nm, such as 30 to 150 nm, such as 40 to 150 nm, or from 30 nm to 200 nm, such as 30 to 100 nm, such as 30 nm to 150 nm, such as 40 nm to 120 nm, such as 40 to 150 nm, such as 40 to 200 nm, such as 50 to 150 nm, such as 50 to 200 nm, such as 50 to 100 nm, or from 10 to 400 nm, such as 10 to 250 nm, such as 50 to 250 nm, such as 100 to 250 nm, such as 200 to 250 nm, such as 10 to 300 nm, such as 50 to 400 nm, such as 100 to 400 nm, such as 200 to 400 nm, each range inclusive. As used herein, "inclusive" refers to a provided range including each of the listed numbers. Unless noted otherwise herein, all provided ranges are inclusive.

Exosomes can be derived from a producer cell, and/or isolated from the producer cell based on one or more exosome isolating characteristics, such as density, size, biochemical parameters, or any combination thereof. In various embodiments, exosome generation does not destroy the exosome-producing cell. Exosomes can include lipids or fatty acids and polypeptides. In various aspects, exosomes include a cargo including, for example, a receiver, e.g. a targeting moiety, a payload, e.g. a therapeutic agent, a sugar, e.g. a glycan, simple sugar, polysaccharide, a polynucle- otide, e.g. a nucleic acid, DNA and/or RNA, and/or other molecules, or any combination thereof. In some embodiments, EVs such as exosomes are free of and do not include genetic material such as nucleic acids therein.

EVs as provided herein include nanovesicles. By "nanovesicle" is meant a cell-derived vesicle composed of a membrane enclosing an internal space, wherein the vesicle is generated from a cell by manipulation, e.g., indirect or direct manipulation, such that the vesicle would not be produced by the cell without the manipulation, and wherein the vesicle has a longest dimension, such as a longest cross-sectional dimension, such as a cross-sectional diameter, ranging for example, from 10 nm to 300 nm, such as such 20 nm to 300 nm, such as 20 nm to 275 nm, such as 20 nm to 250 nm, such as 20 nm to 200 nm, such as 30 nm to 175 nm, such as 30 nm to 150 nm, such as 30 nm to 120 nm, such as 30 nm to 110 nm, each range inclusive. Cell manipulation for nanovesicle production can include application of alkaline solutions, serial extrusion, sonication, or any combinations thereof. In various aspects, production of a nanovesicle results in destruction of the producer cell. Nanovesicles can be derived from a producer cell, and/or isolated from the producer cell based on one or more nanovesicle isolating characteristics, such as density, size, biochemical parameters, or any combination thereof. In some aspects, concentrations of nanovesicles are free or substantially free of EVs that are derived from producer cells by fusion of a late endosome with the plasma membrane or by budding directly from the plasma membrane. Nanovesicles can include lipids or fatty acids and polypeptides. In various aspects, nanovesicles include a cargo including, for example, receiver, e.g. a targeting moiety, a payload, e.g. a therapeutic agent, a sugar, e.g. a glycan, simple sugar, polysaccharide, a polynucleotide, e.g. a nucleic acid, DNA and/or RNA, and/or other molecules, or any combination thereof.

EVs can include one or more macromolecular aspects as cargo. Such macromolecular aspects can be incorporated in an EV for example, on the external surface of the EV, within, e.g., encapsulated by, the internal space, and/or embedded across the membrane. Such aspects can be transported by the EV and can include for example, one or more proteins, e.g., antibodies, carbohydrates, nucleic acids, small molecules, lipids, or any combinations thereof. For example, extracellular vesicles can be stable carriers of enriched genetic material such as nucleic acids including deoxyribonucleic acid (DNA) or ribonucleic acid (RNA), proteins and lipids. Other such nucleic acids are polynucleotides that can include for example, miRNA, siRNA, mRNA, antisense RNA, lncRNA, shRNA and/or a dsDNS. EVs also have membrane proteins that can be markers to identify EV cell-of-origin and thus, EV subtypes. These include but are not limited to tetraspanins (e.g. CD63, CD9), adhesion molecules, integrins, T-cell stimulating molecules (such as MHC Class I and Class II), Annexins, and others. Other specific examples of membrane proteins include CD24, EpCAM, CD-125, CD55, CD63, CD66c, CD66e, CD71, CD98, CD104, CD151, HLA-A,B,C, CD9, CD29, CD44, CD49c, CD49f, CD19, CD21, CD20, CD8, CD151, CD62L, Guanine nucleotide-binding protein G(k) subunit alpha, 60S ribosomal protein L7a, 60S ribosomal protein L15, Calreticulin, Thioredoxin-like protein 1, Asparagine—tRNA ligase, cytoplasmic, Activated RNA polymerase II transcriptional coactivator p15, Gamma-adducin, Coatomer subunit beta, Importin-7, Chromosome-associated kinesin KIF4A, Stress-70 protein, mitochondrial, Heat shock 70 kDa protein 4L, Thrombospondin-1, Host cell factor 1, Nucleoprotein TPR, Ras-related protein Rab-31, ADP-ribosylation factor-like protein 15, Eukaryotic translation initiation factor 3 subunit I, Echinoderm microtubule-associated protein-like 2, Neurobeachin-like protein 2, Target of rapamycin complex subunit LST8, Phospholipase A-2-activating protein, Elongator complex protein 2, WD repeat-containing protein 48, Protein SEC13 homolog, F-box-like/WD repeat-containing protein TBL1XR1, Merlin, Plastin-3, Protein-methionine sulfoxide oxidase MICAL3, Serine/threonine-protein kinase 38, Non-receptor tyrosine-protein kinase TYK2, Nuclear receptor-binding protein, Serine/threonine-protein kinase A-Raf, Glycogen synthase kinase-3 beta, Casein kinase II subunit alpha, Spermidine synthase, Beta-adrenergic receptor kinase 1, Ribosomal protein S6 kinase alpha-1, Serine/threonine-protein kinase TBK1, Mitogen-activated protein kinase 14, Calcium/calmodulin-dependent protein kinase type 1, Mitogen-activated protein kinase kinase kinase kinase 4, Serine/threonine-protein kinase Nek9, Serine/threonine-protein kinase PLK1, cAMP-dependent protein kinase catalytic subunit alpha, Dual specificity mitogen-activated protein kinase kinase 2, STE20-related kinase adapter protein alpha, Casein kinase II subunit alpha, Inhibitor of nuclear factor kappa-B kinase subunit beta, Tyrosine-protein kinase Fer, Cyclin-dependent kinase 2, Aurora kinase B, Rho-associated protein kinase 2, Triple functional domain protein, Serine/threonine-protein kinase D2, Glycogen synthase kinase-3 alpha, Receptor-interacting serine/threonine-protein kinase 1, Serine/threonine-protein kinase MRCK alpha, Inhibitor of nuclear factor kappa-B kinase subunit alpha, Protein kinase C epsilon type, Serine/threonine-protein kinase B-raf, Mitogen-activated protein kinase kinase kinase 3, Unconventional myosin-VI, Unconventional myosin-IXb, Beta-centractin, Protein phosphatase 1 regulatory subunit 12A, Ankyrin repeat domain-containing protein 36B, Ankyrin repeat and FYVE domain-containing protein 1, Caskin-2, HBS1-like protein, Eukaryotic peptide chain release factor GTP-binding subunit ERF3A, Serpin B6, Probable phospholipid-transporting ATPase IIB, Calcineurin B homologous protein 3, Spectrin alpha chain, non-erythrocytic 1, 116 kDa U5 small nuclear ribonucleoprotein component, Elongation factor Tu GTP-binding domain-containing protein 1, Chloride intracellular channel protein 6, Proteasome subunit beta type-3, Proteasome subunit beta type-9, Proteasome subunit beta type-2, Complement component C6, Eukaryotic initiation factor 4A-II, Eukaryotic initiation factor 4A-III, Core histone macro-H2A.1, Probable ATP-dependent RNA helicase DDX6, Leucine-rich repeat and calponin homology domain-containing protein 1, Neurofibromin, Leucine-rich repeat-containing protein 1, SUMO-activating enzyme subunit 1, 3-hydroxyacyl-CoA dehydrogenase type-2, Peroxisomal multifunctional enzyme type 2, Bone marrow proteoglycan, Sepiapterin reductase, F-actin-capping protein subunit alpha-2, Keratin, type II cytoskeletal 6B, 4-trimethylaminobutyraldehyde dehydrogenase, Tyrosine-protein phosphatase non-receptor type 23, Galectin-related protein, Kinesin heavy chain isoform 5A, Kinesin-like protein KIF2A, Kinesin-like protein KIF20B, Kinesin-like protein KIF13B, Kinesin-like protein KIF3C, Clusterin, Eukaryotic translation initiation factor 3 subunit G, Heterogeneous nuclear ribonucleoprotein A3, Poly(U)-binding-splicing factor PUF60, Splicing factor U2AF 35 kDa subunit, Acylamino-acid-releasing enzyme, Dipeptidyl peptidase 9, Serine/threonine-protein phosphatase 2A catalytic subunit alpha isoform, Serine/threonine-protein phosphatase 6 catalytic subunit, Galectin-3-binding protein, Dynein heavy chain 8, axonemal, Dynein heavy chain 5, axonemal, Copine-8, AP-1 complex subunit beta-1, AP-3 complex subunit delta-1, 26S protease regulatory subunit 4, 26S protease regulatory subunit 6B, 26S protease regulatory subunit 10B, 26S protease regulatory subunit 8, Histone H1.4, CAD protein, DnaJ homolog subfamily B member 2, Histone H1.5, Kinesin light chain 1, Clustered mitochondria protein homolog, Thioredoxin reductase 1, cytoplasmic, 60S ribosomal protein L14, D-3-phosphoglycerate dehydrogenase, Agrin, Acetyl-CoA acetyltransferase, cytosolic, Dihydrolipoyl dehydrogenase, mitochondrial, Non-specific lipid-transfer protein, Purine nucleoside phosphorylase, Septin-8, 26S proteasome non-ATPase regulatory subunit 7, STAM-binding protein, DNA ligase 1, Macrophage migration inhibitory factor, 40S ribosomal protein S4, X isoform, ATP-dependent 6-phosphofructokinase, muscle type, 40S ribosomal protein S2, Synaptobrevin homolog YKT6, Band 4.1-like protein 1, Eosinophil peroxidase, EGF-like repeat and discoidin I-like domain-containing protein 3, 40S ribosomal protein S6, Nicotinamide phosphoribosyltransferase, Fermitin family homolog 1, Laminin subunit gamma-1, Alpha/beta hydrolase domain-containing protein 14B, Transcription intermediary factor 1-beta, E3 ubiquitin-protein ligase TRIM21, Coatomer subunit gamma-1, DNA-dependent protein kinase catalytic subunit, Xaa-Pro aminopeptidase 1, Drebrin, 60S ribosomal protein L5, 60S ribosomal protein L4, Eukaryotic translation initiation factor 5A-1-like, Catalase, Importin-9, S-formylglutathione hydrolase, 60S ribosomal protein L3, Trifunctional enzyme subunit alpha, mitochondrial, E3 ubiquitin-protein ligase HECTD1, Probable E3 ubiquitin-protein ligase HERC4, Nucleosome assembly protein 1-like 1, Hypoxanthine-guanine phosphoribosyltransferase, 5-AMP-activated protein kinase subunit gamma-1, Glutamine—tRNA ligase, Serine hydroxymethyltransferase, mitochondrial, Disco-interacting protein 2 homolog A, Protein diaphanous homolog 3, 60S ribosomal protein L13a, Collagen alpha-1 (VI) chain, Protein S100-A9, 26S proteasome non-ATPase regulatory subunit 11, ATP-dependent RNA helicase A, Collagen alpha-3 (VI) chain, AP-1 complex subunit mu-1, 60S ribosomal protein L17, Small nuclear ribonucleoprotein Sm D1, Eukaryotic translation initiation factor 3 subunit A, U6 snRNA-associated Sm-like protein LSm2, 26S proteasome non-ATPase regulatory subunit 1, Serine—tRNA ligase, cytoplasmic, Cathepsin Z, Isoleucine—tRNA ligase, cytoplasmic, Exportin-1, UDP-glucose 6-dehydrogenase, Thioredoxin-interacting protein, Methionine aminopeptidase 2, Cystatin-B, 40S ribosomal protein S19, Eukaryotic translation initiation factor 2A, Eukaryotic translation initiation factor 3 subunit B, Protein enabled homolog, 60S ribosomal protein L19, 40S ribosomal protein S20, Neuron-specific calcium-binding protein hippocalcin, 40S ribosomal protein S23, Brain-specific angiogenesis inhibitor 1-associated protein 2, Importin-8, 26S proteasome non-ATPase regulatory subunit 13, Coatomer subunit delta, Cullin-5, Cullin-4A, Cullin-4B, Flavin reductase (NADPH), N-acetylserotonin 0-methyltransferase-like protein, 1-phosphatidylinositol 4,5-bisphosphate phosphodiesterase beta-2, Ubiquitin carboxyl-terminal hydrolase 47, Inactive phospholipase C-like protein 2, Histone-arginine methyltransferase CARM1, Ubiquitin carboxyl-terminal hydrolase 12, Protein kinase C and casein kinase substrate in neurons protein 3, Proliferating cell nuclear antigen, Phosphoserine aminotransferase, Cysteine-rich protein 2, LIM domain and actin-binding protein 1, Translationally-controlled tumor protein, Acyl-protein thioesterase 1, Lysophospholipase-like protein 1, 60S ribosomal protein L10, 26S proteasome non-ATPase regulatory subunit 5, Peptidyl-prolyl cis-trans isomerase FKBP1A, FK506-binding protein 15, MARCKSrelated protein, 60S ribosomal protein L21, Eukaryotic translation initiation factor 3 subunit C, Heterogeneous nuclear ribonucleoprotein Q, Putative deoxyribose-phosphate aldolase, Heterogeneous nuclear ribonucleoprotein R, Eukaryotic translation initiation factor 2 subunit 3, Dynactin subunit 2, Protein-L-isoaspartate(D-aspartate) O-methyltransferase, Ribose-phosphate pyrophosphokinase 1, Ribose-phosphate pyrophosphokinase 2, Prosaposin, Phosphoribosyl pyrophosphate synthase-associated protein 2, Phosphoribosyl pyrophosphate synthase-associated protein 1, DNA replication licensing factor MCM2, DNA replication licensing factor MCM6, Splicing factor, proline- and glutamine-rich, 60S ribosomal protein L28, Fructose-1,6-bisphosphatase 1, Dedicator of cytokinesis protein 7, Dual specificity protein phosphatase 23, Phosphatidylinositol 3,4,5-trisphosphate 3-phosphatase and dual-specificity protein phosphatase PTEN, Protein phosphatase Slingshot homolog 3, Elongation factor Tu, mitochondrial, Methionine—tRNA ligase, cytoplasmic, Dedicator of cytokinesis protein 6, Protein S100-A10, Secretory carrier-associated membrane protein 1, Eukaryotic translation initiation factor 2 subunit 2, Metalloproteinase inhibitor 1, Vacuolar protein sorting-associated protein 26A, CAP-Gly domain-containing linker protein 1, 40S ribosomal protein S27-like, Putative PIP5K1A and PSMD4-like protein, Rho GTPase-activating protein 4, V-type proton ATPase subunit H, Phenylalanine—tRNA ligase alpha subunit, Cdc42-interacting protein 4, Adenylosuccinate synthetase isozyme 2, Alcohol dehydrogenase class-3, Importin subunit alpha-3, Pre-mRNA-processing-splicing factor 8, S-adenosylmethionine synthase isoform type-2, Aminoacyl tRNA synthase complex-interacting multifunctional protein 2, Regulator of nonsense transcripts 1, Abl interactor 1, 60S ribosomal protein L35, ATP-binding cassette sub-family E member 1, Astrocytic phosphoprotein PEA-15, Hsp90 co-chaperone Cdc37, Disheveled-associated activator of morphogenesis 1, Prolyl endopeptidase, Putative helicase MOV-10, Caspase-14, Histidine—tRNA ligase, cytoplasmic, AMP deaminase 2, Splicing factor 3B subunit 1, AMP deaminase 3, Exocyst complex component 3, Casein kinase II subunit beta, Coatomer subunit epsilon, Eukaryotic translation initiation factor 3 subunit D, LanC-like protein 2, Golgi-specific brefeldin A-resistance guanine nucleotide exchange factor 1, Insulin-degrading enzyme, Thioredoxin domain-containing protein 17, Brefeldin A-inhibited guanine nucleotide-exchange protein 1, AP-1 complex subunit sigma-2, Arf-GAP with Rho-GAP domain, ANK repeat and PH domain-containing protein 1, ATP synthase F(0) complex subunit B1, mitochondrial, Abscission/NoCut checkpoint regulator, Glycerol-3-phosphate dehydrogenase 1-like protein, Leucine-rich PPR motif-containing protein, mitochondrial, Signal recognition particle subunit SRP68, Keratinocyte proline-rich protein, Cytoskeleton-associated protein 5, Chromobox protein homolog 3, V-type proton ATPase subunit C 1, Protein S100-A13, ATP-binding cassette sub-family F member 3, Proteasome-associated protein ECM29 homolog, Pyrroline-5-carboxylate reductase 1, mitochondrial, Aromatic-L-amino-acid decarboxylase, Bone marrow stromal antigen 2, Stathmin, Phosphoribosylformylglycinamidine synthase, Protein phosphatase 1B, Eukaryotic translation initiation factor 4 gamma 2, Eukaryotic translation initiation factor 4 gamma 1, 26S proteasome non-ATPase regulatory subunit 8, Serine/threonine-protein phosphatase 2A 56 kDa regulatory subunit delta isoform, Protein phosphatase 1F, Glia maturation factor gamma, Syntaxin-binding protein 6, Isopentenyl-diphosphate Delta-isomerase 1, Bleomycin hydrolase, Far upstream element-binding protein 2, Replication factor C subunit 2, Signal transducing adapter molecule 1, Phosphomannomutase 2, Tubulin—tyrosine ligase-like protein 12, Insulin-like growth factor 2 mRNA-binding protein 1, UDP-glucose 4-epimerase, Ribonucleoside-diphosphate reductase large subunit, Deoxyribonuclease-1-like 1, Zymogen granule protein 16 homolog B, Transcription elongation factor B polypeptide 1, Lipoma-preferred partner, Tissue alpha-L-fucosidase, Alpha/beta hydrolase domain-containing protein 17A, Neutrophil cytosol factor 4, Thymidine phosphorylase, Ran GTPase-activating protein 1, Complement component 1 Q subcomponent-binding protein, mitochondrial, Splicing factor U2AF 65 kDa subunit, Exportin-T, CCR4-NOT transcription complex subunit 1, Bifunctional coenzyme A synthase, Signal recognition particle subunit SRP72, Protein RCC2, Signal recognition particle 14 kDa protein, Eukaryotic translation initiation factor 4E, DNA topoisomerase 2-alpha, DNA repair protein RAD50, Dedicator of cytokinesis protein 1, Engulfment and cell motility protein 2, Tax1-binding protein 1, Luc?-like protein 3, C-Jun-amino-terminal kinase-interacting protein 4, Type II inositol 1,4,5-trisphosphate 5-phosphatase, Cytosolic purine 5-nucleotidase, Exocyst complex component 8, Putative RNA-binding protein Luc7-like 1, Bifunctional UDP-N-acetylglucosamine 2-epimerase/N-acetylmannosamine kinase, Oxysterol-binding protein 1, 2-deoxynucleoside 5-phosphate N-hydrolase 1, Switch-associated protein 70, Polypeptide N-acetylgalactosaminyltransferase 2, Prolyl 4-hydroxylase subunit alpha-1, Glutamine synthetase, Epsin-1, Transportin-3, OTU domain-containing protein 7B, Ubiquitin carboxyl-terminal hydrolase 15, Glutamate—cysteine ligase catalytic subunit, Carboxy-terminal domain RNA polymerase II polypeptide A small phosphatase 1, Large proline-rich protein BAG6, Centromere/kinetochore protein zw10 homolog, Translation initiation factor eIF-2B subunit delta, Vesicle transport through interaction with t-SNAREs homolog 1A, Minor histocompatibility protein HA-1, Inosine triphosphate pyrophosphatase, BH3-interacting domain death agonist, Ornithine aminotransferase, mitochondrial, RAS guanyl-releasing protein 2, Signal recognition particle 9 kDa protein, Ubiquitin-associated and SH3 domain-containing protein A, Pyridoxine-5-phosphate oxidase, Leucine-rich repeat flightless-interacting protein 1, 6-phosphofructo-2-kinase/fructose-2,6-bisphosphatase 2, Vacuolar protein sorting-associated protein 51 homolog, Mannose-6-phosphate isomerase, DCN1-like protein 3, Succinyl-CoA ligase [GDP-forming] subunit beta, mitochondrial, DnaJ homolog subfamily C member 2, Serine/threonine-protein phosphatase CPPED1, Transcription elongation factor B polypeptide 2, Hematological and neurological expressed 1 protein, CLIP-associating protein 2, DNA-directed RNA polymerases I, II, and III subunit RPABC3, Tubulin-specific chaperone E, Golgi integral membrane protein 4, 2-5-oligoadenylate synthase 2, Sister chromatid cohesion protein PDSS homolog B, Serrate RNA effector molecule homolog, 39S ribosomal protein L12, mitochondrial, Clathrin interactor 1, Sister chromatid cohesion protein PDSS homolog A, 45 kDa calcium-binding protein, FH1/FH2 domain-containing protein 1, AP-3 complex subunit mu-1, FERM domain-containing protein 8, Scaffold attachment factor B1, Active breakpoint cluster region-related protein, Protein C10, Tetratricopeptide repeat protein 38, 2,5-phosphodiesterase 12, Perforin-1, FYN-binding protein, Synapse-associated protein 1, Cancer-related nucleoside-triphosphatase, Mevalonate kinase, Malcavernin, Enolase-phosphatase E1, AH receptor-interacting protein, m7GpppX diphosphatase, E3 ubiquitin-protein ligase ARIH1, Protein FAM91A1, SCY1-like protein 2, Geranylgeranyl transferase type-2 subunit alpha, Translin-associated protein X, Phosphofurin acidic cluster sorting protein 2, Myotubularin-related protein 5, Eukaryotic translation initiation factor 3 subunit J, Sterile alpha motif domain-containing protein 9, Tuberin, CTTNBP2 N-terminal-like protein, GA-binding protein alpha chain, 28S ribosomal protein S27, mitochondrial, Rotatin, BolA-like protein 2, Migration and invasion enhancer 1, Protein pelota homolog, E3 ubiquitin-protein ligase RNF31, Nucleoporin Nup43, Ral GTPase-activating protein subunit beta, Pirin, Tumor necrosis factor alpha-induced protein 8, SH3KBP1-binding protein 1, Condensin complex subunit 2, Nuclear pore complex protein Nup88, RNA polymerase II-associated protein 1, Cytosolic 5-nucleotidase 3A, Core-binding factor subunit beta, Cytosolic endo-beta-N-acetylglucosaminidase, C-Maf-inducing protein, Ribosomal RNA processing protein 1 homolog B, Intraflagellar transport protein 25 homolog, Salivary acidic proline-rich phosphoprotein 1/2, Protein regulator of cytokinesis 1, HCLS1-binding protein 3, Rab3 GTPase-activating protein non-catalytic subunit, 60S ribosomal export protein NMD3, Trafficking protein particle complex subunit 5, Pleckstrin homology domain-containing family G member 3, Nuclear ubiquitous casein and cyclin-dependent kinase substrate 1, Protein SMG8, Myotubularin-related protein 13, HD domain-containing protein 2, Secretoglobin family 1C member 2, Protein WFDC11, Tryptase alpha/beta-1, Centrosomal protein of 112 kDa, Protein kinase C gamma type, Regulator of G-protein signaling 14, 1,2-dihydroxy-3-keto-5-methylthiopentene dioxygenase, Synaptonemal complex central element protein 1-like, GRB2-associated-binding protein 3, Heterogeneous nuclear ribonucleoprotein C-like 1, NAC-alpha domain-containing protein 1, GEM-interacting protein, Rap guanine nucleotide exchange factor 6, Nuclear factor NF-kappa-B p105 subunit, Leupaxin, Kinase suppressor of Ras 1, Phosphatidylinositol 3,4,5-trisphosphate 5-phosphatase 2, Stromal membrane-associated protein 2, Borealin, Polyadenylate-binding protein-interacting protein 1, DnaJ homolog subfamily B member 3, EH domain-binding protein 1, Uncharacterized protein CXorf38, Ubiquitin-conjugating enzyme E2 H, Caspase recruitment domain-containing protein 9, Putative neutrophil cytosol factor 1C, Cell division cycle-associated protein 3, Leucine zipper transcription factor-like protein 1, FYVE, RhoGEF and PH domain-containing protein 3, NEDD8-conjugating enzyme UBE2F, Regucalcin, A-kinase anchor protein 13, RNA binding motif protein, X-linked-like-1, Peroxisomal biogenesis factor 19, Serine/threonine-protein phosphatase 6 regulatory subunit 3, Uracil phosphoribosyltransferase homolog, SH2B adapter protein 1, Egl nine homolog 1, Eukaryotic elongation factor 2 kinase, SH2 domain-containing protein 3C, Nuclear pore complex protein Nup85, Ras and Rab interactor-like protein, Coiled-coil domain-containing protein 6, Coiled-coil domain-containing protein 69, Guanylate kinase, Ethanolamine kinase 1, Zinc finger protein 705A, SHC SH2 domain-binding protein 1, Protein YIPF4, Arginyl-tRNA—protein transferase 1, Putative 3-phosphoinositide-dependent protein kinase 2, Calcium-binding and coiled-coil domain-containing protein 1, Growth arrest-specific protein 7, Protein phosphatase inhibitor 2-like protein 3, Paraneoplastic antigen-like protein 5, Immunoglobulin-binding protein 1, Nuclear factor of activated T-cells, cytoplasmic 3, ADP-ribosylation factor-like protein 2-binding protein, Ubiquitin-associated protein 2-like, FERM, RhoGEF and pleckstrin domain-containing protein 2, Thymidylate synthase, MAP7 domain-containing protein 1, Carboxy-terminal domain RNA polymerase II polypeptide A small phosphatase 2, AN1-type zinc finger protein 6, YTH domain-containing family protein 2, Histidine decarboxylase, Coiled-coil-helix-coiled-coil-helix domain-containing protein 2, mitochondrial, DNA excision repair protein ERCC-6-like, HEAT repeat-containing protein 5B, Small acidic protein, Cytosolic phospholipase A2, Beclin-1, Dual specificity protein phosphatase 8, Phosducin-like protein 3, Sarcoplasmic reticulum histidine-rich calcium-binding protein, TRAF-type zinc finger domain-containing protein 1, DnaJ homolog subfamily C member 21, Integrator complex subunit 7, Protein Mdm4, Testis-specific Y-encoded-like protein 5, Progesterone receptor, DNA replication complex GINS protein PSF1, Spermatogenesis-associated protein 13, Dual specificity testis-specific protein kinase 2, Chloride intracellular channel protein 1, Na(+)/H(+) exchange regulatory cofactor NHE-RF1, Secretory carrier-associated membrane protein 2, Actin-related protein 2/3 complex subunit 1B, Actin-related protein 2/3 complex subunit 2, Alpha-actinin-4, Alpha-endosulfine, Coagulation factor XIII A chain, Prelamin-A/C, Apolipoprotein C-III, Apolipoprotein B-100, Calpain small subunit 1, Guanine nucleotide-binding protein G(i) subunit alpha-2, 60S acidic ribosomal protein P0, Alpha-enolase, Tropomyosin alpha-3 chain, Tubulin beta chain, Profilin-1, Bifunctional glutamate/proline—tRNA ligase, Heat shock protein HSP 90-alpha, Heat shock protein HSP 90-beta, Galectin-1, 60 kDa heat shock protein, mitochondrial, 78 kDa glucose-regulated protein, Heat shock cognate 71 kDa protein, Elongation factor 2, Pyruvate kinase isozymes M1/M2, T-complex protein 1 subunit alpha, 60S ribosomal protein L7, Vinculin, Filamin-A, Ubiquitin-like modifier-activating enzyme 1, Calretinin, 40S ribosomal protein S3, Adenosylhomocysteinase, High mobility group protein B2, Elongation factor 1-delta, Coronin-1A, 14-3-3 protein beta/alpha, Myosin-9, Transgelin-2, V-type proton ATPase catalytic subunit A, Macrophage-capping protein, T-complex protein 1 subunit gamma, T-complex protein 1 subunit theta, Myosin light polypeptide 6, Eukaryotic initiation factor 4A-I, Beta-2-microglobulin, 14-3-3 protein gamma, Calmodulin, 14-3-3 protein zeta/delta, Tropomyosin alpha-4 chain, Hemoglobin subunit alpha, T-complex protein 1 subunit beta, Spectrin beta chain, brain 1, Kinesin-like protein KIF23, Neuroblast differentiation-associated protein AHNAK, Ras GTPase-activating-like protein IQGAP2, Heterogeneous nuclear ribonucleoprotein D0, Cytoplasmic dynein 1 heavy chain 1, Eukaryotic translation initiation factor 4H, Septin-7, Germinal center-associated signaling and motility-like protein, Hematopoietic SH2 domain-containing protein, T-complex protein 1 subunit eta, Protein FAM49B, Septin-9, Ena/VASP-like protein, C-type lectin domain family 11 member A, Talin-1, Heat shock 70 kDa protein 1A/1B, ADP-ribosylation factor 3, Tubulin alpha chain-like 3, Actin, cytoplasmic 1, Elongation factor 1-alpha 1, Histone H2B type 1-K, Gelsolin, Hemoglobin subunit delta, Heterogeneous nuclear ribonucleoprotein M, Polyadenylate-binding protein 3, 60S ribosomal protein L6, 40S ribosomal protein S13, Periostin, Programmed cell death protein 5, Parathyroid hormone-related protein, 14-3-3 protein theta, Rac GTPase-activating protein 1, Phosphoglycerate mutase 1, Glyceraldehyde-3-phosphate dehydrogenase, Kinesin-like protein KIF14, 60S ribosomal protein L8, Protein kinase C beta type, E3 ubiquitin-protein ligase CHIP, Putative adenosylhomocysteinase 2, Glutamine—fructose-6-phosphate aminotransferase [isomerizing] 1, Serine/threonine-protein phosphatase PP1-beta catalytic subunit, Plasminogen activator inhibitor 1 RNA-binding protein, Dehydrogenase/reductase SDR family member 2, mitochondrial, and Nucleolin, Filamin-B, Vesicle-trafficking protein SEC22b, GTPase NRas, GTPase HRas, Transferrin receptor protein 1, ATP synthase subunit beta, mitochondrial, Nucleophosmin, Heat shock protein HSP 90-beta, Guanine nucleotide-binding protein G(k) subunit alpha, Clathrin light chain A, Heat shock cognate 71 kDa protein, Ezrin, ADP-ribosylation factor 4, Ras-related protein Rab-6A, Filamin-A, Nucleoside diphosphate kinase B, Myosin-9, Rab GDP dissociation inhibitor beta, Ras-related protein Rab-5C, Ras-related protein Rab-7a, Transitional endoplasmic reticulum ATPase, CD81 antigen, Cell division control protein 42 homolog, Ras-related protein Rab-8A, Ras-related protein Rab-2A, Ras-related protein Rab-10, Ras-related protein Rab-14, Coatomer subunit zeta-1, ADP-ribosylation factor 6, Ras-related protein Rab-1A, GTP-binding nuclear protein Ran, 60S ribosomal protein L23, 60S ribosomal protein L11, Ras-related C3 botulinum toxin substrate 1, 14-3-3 protein zeta/delta, Eukaryotic translation initiation factor 5A-1, ADP-ribosylation factor 1, Clathrin heavy chain 1, Adenylyl cyclase-associated protein 1, Major vault protein, Importin subunit beta-1, Vesicle-associated membrane protein 3, Ras-related protein Rab-11B, Programmed cell death 6-interacting protein, Vacuolar protein sorting-associated protein 29, and Talin-1.

Such proteins may specifically be found in EVs derived from blood cells, epithelial cells, ovarian cancer cells, non-cancer ovarian cells, renal carcinoma cells, noncancer renal cells, pancreatic cancer cells, noncancer pancreatic cells, non-small cell lung cancer cells, small cell lung cancer cells, non-cancer lung cells, triple-negative breast cancer cells, HER2-positive breast cancer cells, ER-positive breast cancer cells, non-cancer breast cells, glioblastoma cells, glial cells, astrocyte cells, neuronal cells, myeloid cells, cardiomyocyte cells, T cells, B cells, mast cells, dendritic cells, renal cells, peripolar renal cell, mesangial renal cell, macula densa renal cell, kidney parietal cell, kidney glomerulus podocyte, kidney proximal tubule brush border cell, loop of henle thin segment cell, kidney distale tubule cell, interstitial kidney cells, kidney collecting duct cell, juxtaglomerular cell, adrenal gland cells, parathryoid gland cell, pancreatic islet cells, pancreatic duct cell or centroacinar cell, pancreatic stelle cell, hepatic stellate cell, nonstriated duct cell, intestinal brush border cell, exocrine gland striated duct cell, gall bladder epithelial cell, endothelial cells, gut tract cells, keratinizing epithelial cells, surface epithelial cells, urinary epithelial cell, urinary bladder cell, urinary ductal cell, primary sensory neurons, motor neurons, olfactory receptor neurons, photoreceptor cells, autonomic neuron cells, cholinergic neural cell, adrenergic neural cell, peptidergic neural cell, schwann cell, glial cell, microglial cell, enteric glial cell, interneurons, basket cells, cartwheel cells, stellate cells, golgi cells, granule cells, spinal interneuron, renshaw cells, spindle neurons, pyramidal cells, oligodendrocyte, anterior lens epithelial cell, lens fiber cell, adipocytes, liver lipocyte, extracellular matrix cells, fibroblasts, pericyte, chondrocyte, osteoblast and/or osteocyte, skeletal muscle cell, white skeletal muscle cell, red skeletal muscle cell, smooth muscle cell, heart muscle or cardiac cell, nodal heart muscle cell, purkinj e fiber cell, monocyte or white blood cell, erythrocyte or red blood cell, megakaryocyte, platelet, macrophage, neutrophil granulocyte, eosinophil granulocyte, basophil granulocyte, hybridoma cell, helper T cell, suppressor T Cell, cytotoxic T cell, natural killer T cell, B cell, natural killer (NK) cell, reticulocyte, stem cell, mesenchymal stem cells, induced pluripotent stem cell (iPS), embryonic stem cell (ESC), germ cells, thymus epithelial cells, ovarian follicle cells, progenitor cells, satellite cells, intermediate progenitor cells, neural progenitor cell, radial glial cell, bone marrow stromal cells, periosteum, pancreatic progenitor cell, endothelial progenitor cells, exocrine secretory epithelial cell, hormone-secreting cell, anterior pituitary cell, intermediate pituitary cell, magnocellular neurosecretory cell, gut and respiratory tract cell, thyroid gland cell, parathyroid gland cell, adrenal gland cell, leydig cell of testes, and theca interna cell. Other specific examples of proteins carried within EV as cargo are: Annexin A2, ADP-ribosylation factor 4, Basigin, CD59 glycoprotein, CD81 antigen, HLA class I histocompatibility antigen, A-24 alpha chain, GTPase HRas, Heat shock 70 kDa protein 1B, Heat shock protein beta-1, Integrin beta-1, Galectin-3-binding protein, Myosin light chain 3, Myosin light polypeptide 6, Nucleoside diphosphate kinase B, GTPase NRasm Ras-related protein Rab-5C, Ras-related protein Rab-7a, Ras-related C3 botulinum toxin substrate I, Ras-related protein Ral-B, Ras-related protein Rap-1b, Transforming protein RhoA, Vesicle-trafficking protein SEC22b, Transgelin-2, Ubiquitin-conjugating enzyme E2 D3, and/or Vesicle-associated membrane protein 3. Proteins associated with EV membranes can also include antibodies and/or antigen-binding fragments, such as fragments wherein the antigen is a tumor antigen, such as a glycoprotein, peptide or glycolipid. Furthermore, EVs derived from specific cell types, such as EVs from CD4+ cell lines contain specific cell-of-origin proteins, e.g., CD4+ T cell proteins, such as CD4+ and CD3+.

The term "antibody" as provided herein includes an immunoglobulin which is partly or wholly synthetically produced or natural, and fragments thereof. Antibodies include proteins including a binding domain that is homologous to an immunoglobulin binding domain. Antibodies also include polypeptides having a framework region from an immunoglobulin gene or gene fragments thereof that specifically recognizes and binds an antigen. Antibodies include multi-specific antibodies and bispecific antibodies provided they exhibit the desired biological activity. The term antibody includes whole antibodies, monoclonal, polyclonal, and recombinant antibodies, and fragments thereof, as well as humanized antibodies, murine antibodies, single-chain antibodies, chimeric, mouse-human, mouse-primate, primate-human monoclonal antibodies, anti-idiotype antibodies, and antibody fragments, such as, Fab, Fab', scFv, (scFv)2, and Fv, dAb, F(ab')2, F(ab1)2, and Fd fragments, diabodies, and antibody-related polypeptides. Also, as applied in the subject disclosure, the phrase "antigen-binding fragment" refers to fragments of an immunoglobulin, e.g., an intact immunoglobulin, as well as any part of a polypeptide including antigen binding regions having the capability to specifically bind a target antigen. An antigen-binding fragment can be, for example, a Fab' fragment, a Fab fragment, a scFv fragment, a F(ab')2 fragment, or a Fv fragment. An antigen-binding fragment can be made using a protease, e.g., a whole antibody is digested with pepsin to obtain F(ab')2 fragments, and with papain to obtain Fab fragments, and can be prepared using a genetic recombinant technique. Single-chain antibody molecules can include a polymer with a number of molecules which are individual molecules, for example, polymers such as dimers, or trimers.

Membrane proteins can reflect the cellular environment the EV came from, for example a healthy or a tumor cell, or from a particular cell type, for example a specific breast cancer cell type. This genetic material can also hold clues to where the EV came from in the body, and how the EV may be interacting as a signaling messenger in the body.

The ability to detect EVs in various patient biological fluids has been shown to correlate well with disease progression, immune response, and toxicity; thus—the measurement of EVs could aid in disease diagnosis, and monitoring of treatment response. Extracellular vesicles are implicated in cancer progression, cancer metastasis, melanoma, breast cancer, lung cancer, ovarian cancer, kidney cancer, glioblastoma, brain cancer, development of autoinflammatory disease such as Systemic lupus erythematosus, rheumatoid arthritis, multiple sclerosis, inflammatory bowel disease, neurodegenerative diseases such as Alzheimer's disease or Parkinson's disease, prion disease, transmissible spongiform encephalopathy, Creutzfeldt-Jakob disease, synucleinopathy, Dementia, multiple system atrophy, huntington's disease, amyotrophic lateral sclerosis, leukemia, and more.

Different EVs may contain different surface receptors, lipid compositions and different mixtures of internal genetic materials. This results in a broad range of possible EV populations that are in any one sample of biofluid at any time. An EV 'population' is herein defined as any unique combination of variables measured outside and inside EVs and values of said measurements that identifies a certain group of EVs.

The subject embodiments include system for extracellular vesicle characterization. The system can include a processor device, such as a computer processor for: receiving an input including measured physical, biological, or chemical aspects of extracellular vesicles extracted from a biological sample; generating an information architecture that characterizes relationships between biological entities and diseases in humans or other vertebrates; and/or automatically, such as without further input, such as without further human interaction with the device, inferring relationships between the measured physical, biological, or chemical aspects of the extracted extracellular vesicles with the information architecture. An input including measured physical, biological, or chemical aspects of EVs can include any one or combination of measurable and/or identifying EV characteristics described herein, e.g., EV size, internal protein content, intra-membrane protein content, or any combinations thereof, etc. Furthermore, in various instances, the system includes a processing device that produces an output of the automatically inferred relationships. The output can be a readable medium, such as an electronic digital rendering produced on a digital screen and/or a printed record, e.g., a paper readout. The readout is recognizable and interpretable by a human operator.

Systems according to the subject embodiments can also include one or more extracellular vesicle isolation devices for extracting extracellular vesicles from a biological sample. Extracellular vesicle isolating devices according to the subject embodiments are devices which can isolate and/or extract EVs, as described herein. Such devices include centrifuges, ultracentrifuges, microfluidics chips, immunomagnetic bead-based methods, immunoprecipitation columns, and sucrose density gradient columns.

Various systems according to the subject embodiments include one or more extracellular vesicle characteristic measuring device for measuring physical, biological, or chemical aspects of extracted EVs. Such aspects can be any of the EV aspects described herein. Such devices can include a next-generation sequencer, a mass spectrometer, mass cytometer, western blot, PCR, RNA microarrays, DNA microarrays, protein arrays, a nanoparticle tracker, a flow cytometer, a fluorescent microscope, or any of the other devices described herein.

Figure 1:
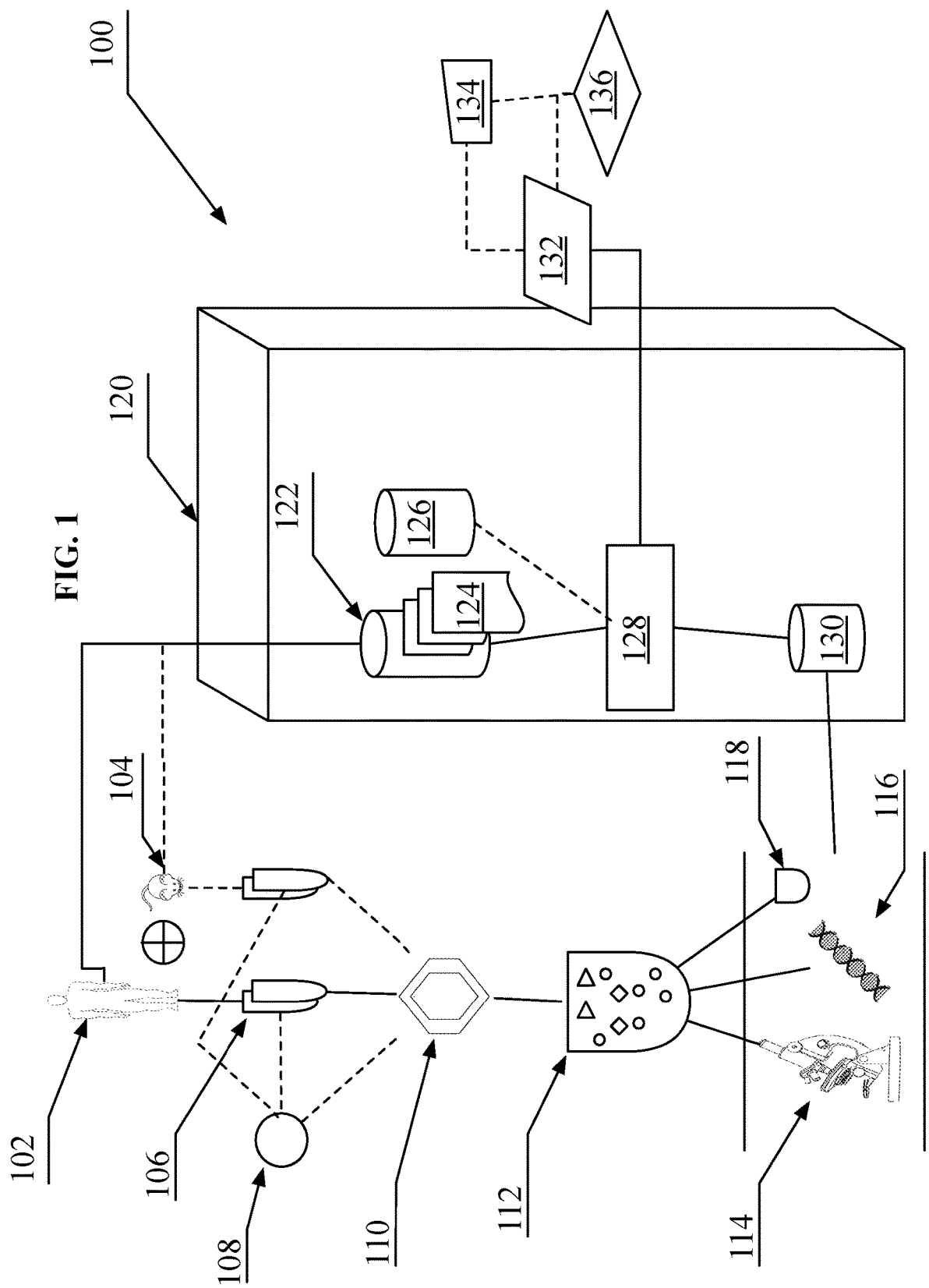

FIG. 1 illustrates one example of a system (100) for extracellular vesicle characterization, according to various embodiments of the present disclosure. In some embodiment, a sample (106) from a human (102) or an animal (104) is either directly inputted into an Extracellular Vesicle (EV) isolation device (110) or first cultured in vitro (108) and then placed into the isolation device. In some embodiments, if in vitro culturing is implemented (108), cell lines may be used that were originally sourced from a human or animal but have been passaged and cultured as cell lines. In some embodiments, the EV isolation device produces a sample that contains population(s) of EVs with possible a mixture of surface receptors and internal genetic material (112). In some embodiments, measurements are then done on the internal contents, membrane, and external contents EVs or any combination thereof. In some embodiments, examples of possible measurements include EV internal, external, and transmembrane proteins, using devices and methods such as ELISA, microscopy, fluorescent microscopy, flow cytometry, mass spectrometry, mass cytometry, protein western blot, protein microarrays, immunohistochemistry, or any combination thereof (114). In some embodiments, possible measurements includes genetic material inside of the EVs, using devices and methods such as DNA-seq methylation, DNA array methylation expression, DNA-seq somatic mutation expression, DNA array somatic mutation expression, DNA-seq germline mutation expression, DNA array germline mutation expression, DNA ChIp-Seq expression, RNA-seq expression, RNA microarray expression, single-cell RNA-seq expression, PCR, or any combination thereof (116). In some embodiments, examples of possible measurements includes other EV characteristics like lipid bilayer composition, zeta potential, and measurements derived from methods such as size exclusion chromatography, nanoparticle tracking, and resistance pulsing, or any combination thereof. In some embodiments, any combination of measurements pertaining to parts 114, 116 and 118 in FIG. 1 are used. In some embodiments, these measurements are then fed into a computing system and architecture (120) that incorporate further data on the sample collected (122). In some embodiments, this further data includes the medical history (124) of the patient from whom the sample was collected and public reference databases such as curated experimental results and data on EV, cell, or patient measurements, tissue of-origin genetic markers, tissue-of-origin protein markers, cell-of-origin genetic markers, cell-of-origin surface, transmembrane and internal markers, chemical compound, therapeutic compound, and therapeutic compound target data (126). In some embodiments, this further data includes biological characteristics of the in vitro cell culture (108) from which the EVs were derived, such as cell surface proteins, transmembrane cell proteins, internal cell proteins, internal genetic material, and how the in vitro cell culture was prepared, such as the type of culture media used and possible therapeutic compounds dosed or external stimuli applied to the cells in culture. In some embodiments, this data in parts 122, 124, and 126 are stored in relational (such as SQL), non-relational (such as noSQL), or graph databases with standardized schemas across all data types to enable automatic inference of EV measurements across common experimental conditions, human or animal disease conditions, biological or clinical states and conditions, or any combination thereof, using programmatic database languages such as SQL to query and compare across databases. In some embodiments, this sample-specific EV and non-EV data and data is used as feature inputs to a deconvolution algorithm (128) that computationally predicts which EV populations are in the sample or samples (132), and correlates these populations with relevant clinical variables of interest present in the medical history linked to the sample (130). In some embodiments, the user can decide (134) to run further EV experiments to interrogate these specific populations (136), the system may automate further EV experiments or not immediate action may be taken. In certain embodiments, isolation and extraction of the EVs and measurements of EV characteristics, or any combination thereof (102-118) is completed in a physically different site from where the system architecture is located. Examples 1 and 3 provide details of such embodiments.

Definition of a Sample and its Source (102-106)

A "biological sample" is a sample containing a quantity of organic material, e.g., one or more cells or extracellular vesicles or organic molecules, such as one or more nucleic acids e.g., DNA and/or RNA or portions thereof, that can be taken from a subject. A biological sample can contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

In various aspects, biological samples can be collected from a subject and can include one or more cells, such as tissue cells, or extracellular vesicles, of the subject. As used herein, the term "tissue" refers to one or more aggregates of cells in a subject (e.g., a living organism, such as a mammal, such as a human) that have a similar function and structure or to a plurality of different types of such aggregates. Tissue can include, for example, muscle tissue (e.g., cardiac muscle; smooth muscle; and/or skeletal muscle), organ tissue, connective tissue, nervous tissue and/or epithelial tissue. A biological sample can also not include one or more cells. In some embodiments, a biological sample can include free DNA, free RNA, viral particles, bacteria cells or cell portions, fungi, spores, prions, or any combination thereof. Samples can also be fluid, e.g., liquid, samples.

As used herein, the terms "subject," "individual," and "patient" are used interchangeably to refer to a vertebrate, such as a mammal, such as a human. In some embodiments, a subject is a "mammal" or a "mammalian" subject, where these terms are used broadly to describe organisms which are within the class mammalia. Mammals include, but are not limited to, murines, simians, humans, farm animals, sport animals, and pets. Tissues, cells and their progeny of a biological entity obtained in vivo or cultured in vitro are also encompassed. The term "humans" may include human subjects of both genders and at any stage of development (e.g., fetal, neonates, infant, juvenile, adolescent, and adult), where in various embodiments the human subject is a juvenile, adolescent or adult.

EV Isolation and Populations (110, 112)

In some embodiments, any type of biological sample, taken directly from a subject (102, 104) is prepared and processed through an extracellular vesicle (EV) isolation device (110). This device produces a concentrated solution of EVs, which contains one more different types of EV), where type may be defined by, but is not limited to, lipid bilayer membrane composition, size, composition of membrane surface proteins, deoxyribonucleic acid (DNA) measurements inside the EVs, ribonucleic acid (RNA) measurements inside the EVs, protein measurements inside the EVs, lipid measurements inside the EVs, and/or other internal or external biological features of the EVs.

In some embodiments, the method provides a capturing agent that binds to an extracellular vesicle component, such as a membrane protein of the extracellular vesicle, to capture the extracellular vesicle. For example, the capture agent can be a capture antibody, such as a monoclonal antibody, that binds to or has an affinity to an antigen on the extracellular vesicle. In a further embodiment, the capture agent includes a protein, a peptide, a divalent metal-based complex, or an antibody. In one embodiment, the capture agent can be immobilized on a solid substrate. In another embodiment, the solid substrate is selected from a purification column, a microfluidic channel or beads, such as magnetic beads. In some embodiments, the method used for purification of the extracellular vesicles, can be a microfluidic affinity based purification, a magnetic based purification, a pull-down purification or a fluorescence activated sorting-based purification.

EV-Specific Data Linked to Sample (114, 118, 116)

In some embodiments, multiple data types are measured from the EV populations. One such example is measurement of the protein receptors found on the surface and inside of the EVs, using methods such as fluorescence microscopy tagging specific proteins, ELISA methods or flow cytometry or mass spectrometry to measure a larger number of proteins simultaneously. In some embodiments, another data type measured may be the lipid bilayer membrane compositions of the EVs. Another possible measurement is the genetic material inside EVs, including RNA expression using microarrays, rna-seq or PCR, gene-protein interactions using ChIp-Seq, DNA mutations using microarrays or DNA-seq and/or DNA methylation using microarrays. Additional possible methods to measure these genetic data types include polymerase chain reaction (PCR), reverse transcription polymerase chain reaction (RT-PCR), real-time polymerase chain reaction (qPCR), digital polymerase chain reaction (dPCR), enzyme-linked immunosorbent assay (ELISA), western blot or gel electrophoresis. Each of these data types may provide unique or combined predictive power to the deconvolution algorithm to improve detection of specific EV populations. A third measurement example is the lipid bilayer composition of the EVs.

Computing System (120)

The computing system consists of data storage devices for the EV measurements (122), clinical sample medical history data (124, 126) and other reference data (126). In some embodiments, the information carrier into the deconvolution algorithm is a computer or-machine readable medium, such as a memory, storage device or memory processor. This computing system, on a server, a group of servers, or a personal machine such as a laptop computer, stores these different data types and feeds these data types into the deconvolution algorithm. The processor or processors then run the deconvolution method to characterize the EV populations in the sample.

Deconvolution Algorithm (128)

In some embodiments, the deconvolution method is a model or group of models that take as input the various data types previously mentioned and predicting which EV populations are most likely present in the original sample used to isolate EVs. Each EV population may be predicted using its own specific model, or unified model may jointly predict several populations.

Example 1 is an example of the deconvolution algorithm using one possible class of machine learning methods, support vector machines, where the algorithm automatically predicted the types of cells EVs were derived from using measurements of EVs isolated and extracted from a mixture of cell types. Example 3 is an example of the deconvolution algorithm using statistical tests, where the algorithm automatically predicted a particular EV population, defined by its surface proteins and internal genetic material, that may target or interact with cells from a certain disease. In some embodiments, the deconvolution algorithm is implemented as an automatic computational program on a computing server or servers using support vector machines, decision trees, graphical models, random forests, graphical lasso, statistical tests, deep learning models, neural networks, linear regression, logistic regression, regularized regression such as L1 or L2 regularization, linear discriminant analysis, quadratic discriminant analysis, clustering such as k-means, hierarchical clustering, matrix factorization methods such as PCA, non-negative matrix factorization, self-organizing maps, regularized PCA, regularized non-negative matrix factorization, nearest shrunken centroids, or any combination thereof. In some embodiments, the deconvolution algorithm is automatically trained, meaning the weights for each model or models used in the algorithm are automatically fitted using a computational programming script on a server or servers, using reference databases (126) and previous sample experiments already analyzed by the system. Example 3 provides an embodiment of automatically training an algorithm using data measured from EVs from several experiments, including RNA expression of EVs isolated and extracted from human blood, RNA expression of EVs isolated and extracted from cell culture, and protein expression of EVs isolated and extracted from cell culture.

In some embodiments, the deconvolution algorithm is built using reference databases (126) and previous sample experiments already analyzed by the system, so that the system can be improved upon when new samples are measured or new external data is added. An improvement is defined as more accurately finding relationship matches or more accurately identifying certain variables of interest such as a disease state that is indeed present in a sample or a biochemical compound that if used on the sample, induces desired chemical effects.

As used herein, "built" is defined as training a statistical model with an input dataset and output or 'truth' variables of interest. In order to predict or correlate multiple variables of interest, different models may need to be trained on different subsets of the reference data. An example is a subset of the reference data pertaining to cancer that is used to create a cancer prediction model, and a subset of the reference data pertaining to a biochemical compounds effects that is used to predict whether the compound has utility as a pharmaceutical agent.

The aforementioned reference databases contain previously defined relationships between biological entities, diseases and biochemical compounds that may be used as pharmaceutical agents. The deconvolution algorithm quantifies any of these relationships that may also exist in the input EV sample measurement, and compares the EV sample relationships to these reference relationships to identify potential sets of relationship matches. Sets of relationships can be compared using several types of models; for example, in graphical models, neural networks/deep learning methods and decision trees, each relationship may be an input variable; the values of these variables found in the EV dataset are used by the model to predict whether the EV dataset is associated with the same variables of interest as the reference data used to build the model. In network methods, the EV set of relationships and the reference sets of relationships can be viewed as two matrices, and the distance, similarity or covariance is computed between the two matrices.

Because some of the data types included in this algorithm are related to the clinical history of the patient linked to the sample, the identified EV populations can also be correlated back to clinical variables such as tumor stage, age, predisposition to a certain cancer and diseases like diabetes or Alzheimer's disease.

Incorporating Reference Data Into the Algorithm (126)

Given the inability to know ahead of time, and analyze, every possible sample to create a comprehensive database of features such as proteins, RNA and DNA expression, methylation, lipid bilayer and experimental and clinical characteristics, and how they are interrelated, existing reference databases can be used to establish the first iteration of the relationships between these features, and thus the first iteration of the coefficient fits, or values, of the variables in the deconvolution algorithm. A reference database is defined as any pre-existing dataset, embodied in any form (examples include a relationship database, a spreadsheet, a text file, a visualization or a web site.) These databases may or may not be publicly available.

In a certain embodiment, protein-gene relationship databases such as the Biogrid can be used. Such databases can help identify potentially related genes and proteins from a specific gene or protein found in a specific input sample. Pathway databases, such as pathway commons, can also identify key biological pathways a certain molecular feature may be a part of.

Reference databases may also include pharmacological databases such as the Druggable Genome or the Cancer Cell Line Encyclopedia to identify particular genes that are linked to proteins that can easily be made into drugs, or genes that are known to interact with certain existing drugs. In some embodiments, these types of relationships can provide recommendations for treatment decision, monitoring and new drugs. There are also EV-specific databases, such as Vesiclepedia that provide relationships between certain proteins, RNAs and lipids and diseases. Reference databases may also include identification of molecular features that are correlated with environmental factors, such as toxins or physical activity.

EVs have also been implicated in immune system function. In some embodiments, incorporating databases such as ImmPort can provide information on relationships between types of immune cells, diseases and drugs. In an example embodiment, the EV populations being predicted by the deconvolution algorithm may be closely correlated with or represent certain immune cell lineage populations.

Incorporating Sample Data Into the Algorithm (122, 124, 130)

As used herein, sample-specific data is defined as data that are direct measurements of a specific sample or group of samples. For example, while a reference database may summarize aggregate trends found across many biological experiments, a sample-specific dataset may contain the exact gene expression levels or proteins found in that sample. It may also contain any of the aforementioned clinical history variables that were not measured at the time of the biological experiment, but are known about the subject the sample was taken from. In some embodiments, clinical variables from subjects, whether specifically linked back to a certain sample or not, may be continuously updated after the experiment is run to incorporate data across greater than one time point into the deconvolution algorithm.

In some embodiments, sample data includes experimental data from public repositories such as the Gene Expression Omnibus or Array Express. In an embodiment, sample data includes data collected on samples that are housed in sample repositories that was or will not be recorded in conjunction with the EV isolation and analysis process, where EV RNA expression data was automatically downloaded from a web server to a private cloud server from Gene Expression Omnibus.

In some embodiments, different deconvolution algorithms will be built for different groups of samples pertaining to a specific clinical or pharmacological or environmental condition or a specific subject. Examples 1, 2 and 3 provide examples of different algorithms pertaining to such different states: the system architecture in Example 1 used a support vector machine to predict the cell type from which EVs originated from, the system architecture in Example 3 used statistical tests to predict an EV population that can be used to deliver targeted therapeutic compounds to alter a disease of interest in a patient, and Example 2 used an unsupervised learning method, hierarchical clustering, to identify de novo populations of EVs across different cell types.

In some embodiments, not only the actual measurement values themselves, but the quantified relationships between these values, will be added to the data storage system(s). This is so that this new data is interpreted as a relationship, making it more amenable to be automatically incorporated into machine learning models such as network-based community detection methods, graphical models and neural networks. This is because these types of methods either take as input pre-defined quantifications between certain measurement values, or further quantify the relationships. In this respect, the measurement values become variables in these models.

In some embodiments, as sample-specific data is collected by this system, the relevant databases will be updated and the model will be updated and improved with this new information. As used herein, "updated" is defined by two main actions of the system: automatically adding this new sample data and any inferences made upon it into the data storage system(s), and updating the deconvolution model(s). Automatically updating any statistical or computational model(s) used by the system involves the computing system appending this new data to the existing data in the data storage devices and then re-computing the coefficient values of the variables in the model(s) using this larger combined dataset. The details of coefficient value computation are model-dependent, but this computation in general involves optimizing the coefficient fits so that the input training data highly accurately predicts the output or "truth" training labels.

When re-computing the coefficient values, the system may encounter certain types of data measured in this new sample-specific data that was not previously incorporated into the model. Many models require that either this non-intersecting data type is removed before re-computing the coefficient values, or that all of the previous datasets in the data storage(s) are now also given this additional variable, but with a value code that is known to represent a missing value. Separate sets of model coefficients can also be computed if there is frequently a certain variable(s) that is missing but is desirable to include in the model(s) when it is non-missing in a dataset.

Non-EV Specific Data Linked to Sample (126, 130)

In some embodiment, all or some of these EV-related measurements are then used as variables in a (statistical/computational) deconvolution method. In addition, a set of criteria that are not related to the EV measurement process may also be used as variables in a computational deconvolution method. These non-EV related variables may or may not be included within the deconvolution method. These non-EV related variables include, but are not limited to, the age of the subject (human or animal) that the biofluid sample was collected from, the hospital where the biofluid sample was collected, the time or date at which the biofluid sample was collected, the therapeutic treatment history of the subject that the biofluid was collected from, non-EV related genetic information, such as tissue DNA or RNA and/or circulating DNA or RNA in blood, of the subject that the biofluid was collected from, hereditary information of the subject that the biofluid sample was collected from, the gender of the subject that the biofluid sample was collected from, environmental information, such as air quality or weather, related to the subject that the biofluid sample was collected from, and behavioral information, such as diet or exercise, related to the subject that the biofluid sample was collected from. For in vitro engineered biofluids, the non-EV related variables that may or may not be included within the deconvolution method include, but are not limited to, cell culture parameters, such as cell type, reagents used, other chemicals administered, in vitro engineering protocol, and date and time the experiment was run.

Algorithm Implementation

Figure 2:
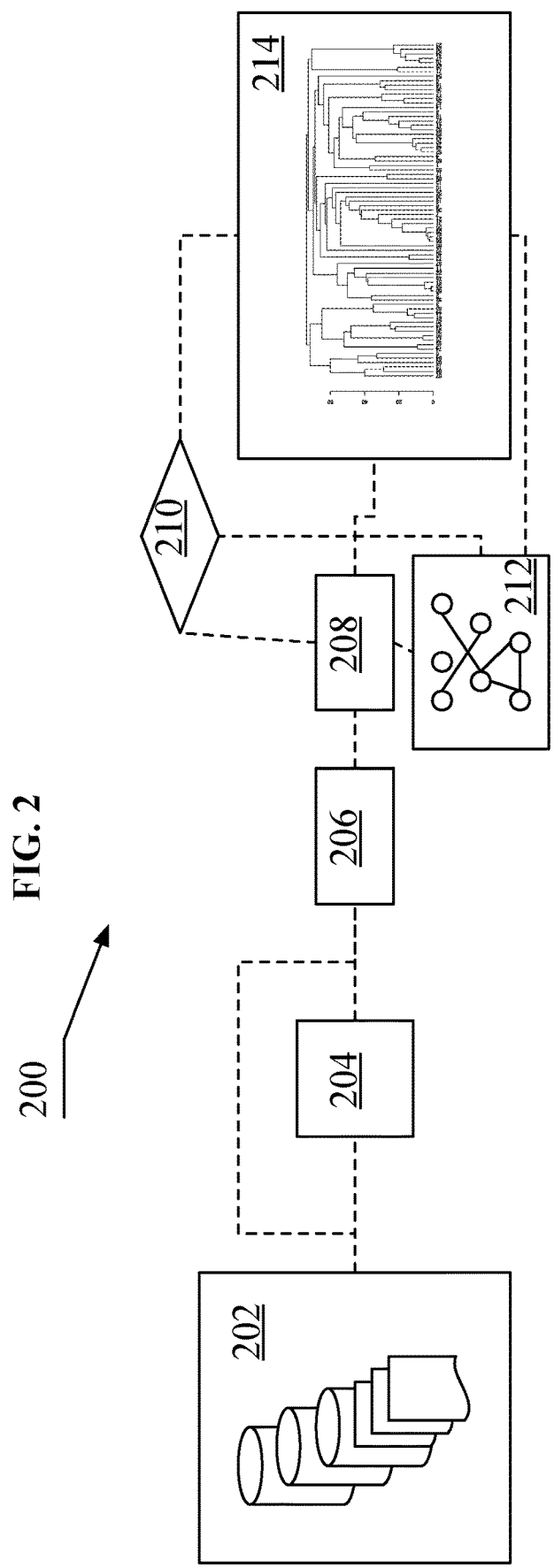

FIG. 2 is a box diagram showing an example workflow for building a deconvolution algorithm. FIG. 2 details the steps and examples of how to implement the deconvolution algorithm after all of the desired data inputs are measured and stored in a data storage device such as a relational, non relational or graph database or excel or text files on a server or personal laptop. These implementation details are intended to expand upon box 17 in FIG. 1 that represents the deconvolution algorithm.

FIG. 2 contains predominantly dotted, as opposed to solid lines, to imply that these steps can often be used in various orders and combinations to achieve a suitable deconvolution algorithm.

Preparing the Data (202, 204)

Input data, represented in box 202 in FIG. 2, may need to be post-processed or further prepared before inputting it into the deconvolution algorithm. In some embodiment, missing variables may be imputed (204). In some embodiment, the EV and other data-derived algorithm input variables may be used to create secondary aggregate or summary variables (206). In some embodiment, these resulting variables may be pruned (208) to create a smaller, more manageable variable feature set for a statistical or computational algorithm.

In some embodiment, initial larger set of variables may be pruned before the main predictive statistical model (210) or EV population clustering (214) is run. "Statistical model" is defined here as not the full deconvolution algorithm with all steps in FIG. 2, but in some embodiments of a model like linear regression, support vector machines, deep learning or graphical models, that takes as input a specific set of features and produces an output prediction or insight. The insight may also be not the prediction of a certain outcome, but relationships between different variables or entities, such as network (elaborated on in Details section).

In some embodiment, different users or computers may input only a subset of the total available variables. Depending on the computational models used, this may result in different model fits for each unique permutation of available variables, allowing for future improvement of the model when another biofluid is inputted that contains the same set of matching variables. As used herein, "fit" pertains to the final coefficient values assigned to each variable in a model. In some embodiment, in a similar manner, when entirely new variables are discovered or measured, a new model fit will be produced.

Inferring Relationships Between Data Types

In some embodiment, integrating these various reference data types lends itself to a quantification of the relationships between variables (212). A final statistical model (210) that predicts an outcome may or may not be employed after quantifying these relationships, as the relationships alone, such as in a biological network, may provide useful insights for what biological features and EV populations a scientist wants to explore further. Such relationships can be quantified using models such as clustering methods, graphical models, network community detection methods, neural networks or deep learning and random forests. Example 2 provides an example of clustering to identify relationships between different EV populations from different cell types.

In some embodiments, data will be used to train (fit or build) a predictive model, such as linear or logistic regression or random forests. Binary relationships can be interpreted as binary variables and continuous relationships can be interpreted as continuous variables in these models.

In some embodiments, no reference databases will be used and only new sample experiments will be used to build the algorithm. In some embodiments, only reference databases may be used to build the algorithm, or a mix of reference databases and new sample experiments will be used.

In some embodiments, different modeling methods to integrate this reference and/or sample data may be used for different end purposes, such as predicting a certain cancer versus predicting a potential new drug. In some embodiment, given the deconvolution step may be composed of several individual models that predict different labels, the user may interpret each label individually, the system may return only selected labels for further inspection based upon defined threshold(s) or metrics, or ensemble model(s) may be used. In some embodiment, if several closely related but distinct EV populations must be identified, a machine learning ensemble method such as a Bayes optimal classifier, which provides a final "vote" on which of the closely related labels is indeed the most probable label. Example 1 provides an example of an embodiment where the optimal EV population is automatically predicted using a machine learning algorithm; in this case, the EV population is the cell type the EVs were derived from.

Identification of Relevant Populations (212, 214)

In some embodiments, EV populations are defined by directly clustering the data measurements as described in the previous section. Example 2 is such an example. Data in the reference databases can then also be clustered, and the similarity of clusters between the reference and EV sample measurements can be quantified. One such method is Coincide, a method that computes the similarity between clusters from different datasets and then uses these similarities as edges in a network. The network is then divided in subgroups called communities using community detection algorithms such as the Girvan-Newman algorithm to determine whether clusters from the different datasets fall into the same community.

In some embodiments, relationships between measurement values in the EV sample data and relationships between values in the reference database are more directly treated as edges in networks, and thus the networks are compared to quantify their similarity. The reference database may contain relationships and attributes or values of these relationships that are specific to a certain variable of interest, such as disease state or drug, and then multiple networks may be created from the reference database and compared to the EV sample data relationships.

In some embodiments, these networks of relationships can be represented as adjacency matrices, where the rows and columns are node IDs, and values inside the matrix are the edge weights or status. The matrix does not need to be symmetric to allow for the optional directionality of the edges (i.e. a certain process only goes from node A to node B, and not vice versa). The similarity or dissimilarity of the adjacency matrix for the EV sample data relationships and the adjacency matrix for all or a subset of the reference database matrices can be computing using matrix similarity methods such as covariance, Spearman's or Kendall's rank correlation or matrix distance methods such as Euclidean or Manhattan distances.

In some embodiments, the reference relationships are used to fit a graphical model, neural network, deep learning model, decision tree or random forest, and then the reference data is compared to the EV sample data by inputting the EV sample data into the model as a test dataset that is used to predict whether the test dataset has or is related to the outcome or truth variable(s) of interest used to fit the model. Graphical models, neural networks, deep learning models, decision trees or random forests can all be interpreted as quantifying relationships between variables, but in the case of neural networks and deep learning models, the actual nodes and edges that exist in the final model are determined in part during the model fitting process and may be a combination or a subset of the original input data types (variables) used. Graphical models, decision trees and random forests would contain a subset of the variables only if techniques such as regularization or thresholding were specifically added to reduce the number of final coefficient variables used in the model.

Prediction or Correlation with Outcome Variables of Interest (210)

In some embodiments, in addition to identifying relevant populations of EVs, patients and/or therapies, identified populations and/or data types will also be correlated with variables of interest, such as disease state or therapeutic response. In an embodiment, these variables of interest will be directly prediction through supervised models that are trained on datasets that include known values of these variables of interest. Example predictive algorithms include linear and logistic regression and singular value decomposition.

Continuous Improvement of the Algorithm

The accuracy of this algorithm, and its ability to identify different EV populations, will continuously improve as more samples are run through the system that contain different EV populations, known or unknown a priori, and different clinical histories. This improvement comes from re-fitting, or re-computing the coefficients of the model using optimization techniques specific to the model(s) selected. The model must be re-fit because new input, or training, data can now be added in. This new data is appended to the exist data that was previously used to fit the model, and then the model is re-fit using this new combined dataset. In some embodiments, fitting techniques include gradient descent and maximum likelihood estimation. These techniques estimate the most likely or probably magnitude the coefficients for each variable in the model based upon the training data, or input dataset.

Benchmarking of the Algorithm

In some embodiments, incorporating at least one sample dataset that contains the final variable of interest measured, i.e. a truth label, provides a way to benchmark the algorithm and confirm its predictive accuracy. In some embodiments, the truth label is a set of specific surface receptor proteins used to only isolate EVs with these specific receptors. The same set of samples are measured in two different ways: once selecting only EVs with some combination of these receptors, and once without this selection. Running the second, non-receptor-specific sample data through the deconvolution algorithm will produce a prediction of the EV receptors that exist in this set of broader sample measurements. A useful and accurate deconvolution algorithm will at a minimum identify that the broader sample measurements contained the specific receptors found in the first set of sample measurements.

In some embodiments, truth labels can be derived not through more selective EV population isolation approaches but through proxies. In some embodiments, these proxies may include known protein or genetic features that are highly correlated with a disease or a certain organ, thus suggesting where the EV originated from in the body. Example 1 provides an example of where the truth labels are the types of cells the EVs were derived from. Tables 6-12 report prediction accuracies on these truth labels using various model fits of the computational system, generated by fitting models using different input feature sets. The predicted fraction of each possible cell type and the true fraction of each cell type are reported side by side.

In some embodiments a used to identify EV populations through proxies, such as disease state, may not need to be mathematically optimized to obtain variable fits, but rather be embodied instead as a binary decision tree. When certain proteins or levels of genetic measurements are present, the decision tree then identifies the relevant prediction variables of interest as highly probable. In some embodiments, experimental data such as the type of isolation method, time of day and laboratory equipment used is incorporated into the deconvolution algorithm as model variables to provide feedback on what specific experimental conditions result in more accurate EV population and outcome variable of interest prediction.

Recommendation (132)

A recommendation is defined broadly as an automatically predicted outcome or insight that is useful to the end user of the system, usually a scientist, clinician, patient, or automated lab system. In some embodiments, the recommendation may be made via a computer display text message, a visualization, an audio recording, a text file output or data output written to a data storage system, or an automated message relayed to a second computing system. In some embodiments, a recommendation that certain EV subpopulations exist in the sample(s) of interest may cause a user to decide to run further specific experiments that bias the EV isolation techniques to attempt to capture only these subpopulations for more precise, focused analyses to understand better how these subpopulations function and are implicated in scientific or clinical variables of interest.

EV Isolation and Populations (110, 112)

In another embodiment, the method of the present disclosure may further include a step of separating one or more populations or subpopulations of extracellular vesicles from a purified pool of extracellular vesicles. In some aspects of the present disclosure, a sub-population of extracellular vesicles from a mixed extracellular vesicle population, found for example in a biological sample obtained from a body fluid or cell culture, can be further purified or isolated, for example according to one or more specific cell types or cell subtypes.

In some embodiments of the present disclosure, extracellular vesicles may be concentrated or isolated from a biological sample using size exclusion chromatography, density gradient centrifugation, differential centrifugation, nano-membrane ultrafiltration, tangential flow filtration, cross-flow filtration, immunoaffinity capture, affinity purification, microfluidic separation, gel permeation columns, anion exchange, gel permeation chromatography, sucrose density gradients, organelle electrophoresis, colloidal separation by acoustic waveforms, magnetic activated cell sorting (MACS), or any combination thereof.

In some embodiments, the method provides a capturing agent that binds to an extracellular vesicle component, such as a membrane protein of the extracellular vesicle, to capture the extracellular vesicle. For example, the capture agent can be a capture antibody, such as a monoclonal antibody, that binds to or has an affinity to an antigen on the extracellular vesicle. In a further embodiment, the capture agent includes a protein, a peptide, a divalent metal-based complex, or an antibody. In one embodiment, the capture agent can be immobilized on a solid substrate. In another embodiment, the solid substrate is selected from a purification column, a microfluidic channel or beads, such as magnetic beads. In some embodiments, the method used for purification of the extracellular vesicles, can be a microfluidic affinity based purification, a magnetic based purification, a pull-down purification or a fluorescence activated sorting-based purification.

In some embodiments, purification or concentration of extracellular vesicles may be achieved by removing other abundant proteins in the biological sample that may hinder isolation of the EV. For example, a system that utilizes antibodies specific to abundant proteins found in blood, such as albumin, immunoglobulin, glycopeptide, cytoplasmic epitopes, or anti-cytoplasmic epitopes, or lipoproteins, can be used to remove several proteins at once, thus revealing lower abundance species such as extracellular vesicles.

In another embodiment, purification or concentration of extracellular vesicles from a biological sample may be achieved by utilizing lipid-specific proteins, such as Annexin A5 or Lactadherin, to act as capture agents targeting the lipid membranes of extracellular vesicles. The method could utilize one or more lipid-specific proteins simultaneously and in conjunction with any of the aforementioned methods. In one embodiment, lipid-specific proteins or lipids with affinity to the lipid membrane of extracellular vesicles could be linked to a solid substrate.

In a further embodiment, purification or concentration of extracellular vesicles from a biological sample may be achieved by utilizing capture agents such as antibodies with affinity to phosphatidylinositol lipids or phospholipids on the membrane of the extracellular vesicles. For example, antibodies for phosphatidylinositol (4,5)-bisphosphate (PIP2) or phosphatidylinositol (3,4,5)-trisphosphate (PIP3) may be utilized to capture the extracellular vesicles. The method could utilize one or more capture agents with affinity to phosphatidylinositol lipids or phospholipids and in conjunction with any of the aforementioned methods.

In another embodiment, purification or concentration of extracellular vesicles from a biological sample may be achieved by utilizing capture agents with affinity to glycans such as antiglycan antibodies and lectins. The method could utilize one or more capture agents with affinity to glycans and in conjunction with any of the aforementioned methods.

In a further embodiment, purification or concentration of extracellular vesicles from a biological sample may be achieved by electrophoretic or electrokinetic separation techniques. In some embodiments, he extracellular vesicles can be isolated using an electrophoretic separation method for separating charged substances or separation based on electrokinetic potential such as zeta potential of the extracellular vesicles. In one embodiment, the system may use a known free-flow electrophoretic separation method and apparatus for separating charged substances such as protein, cells, or extracellular vesicles by electrophoresis. In some embodiments, this method includes supplying a mixed solution containing the charged substances such as EVs to be separated, which are dissolved in a separation buffer, into a separation chamber, circulating the mixed solution inside the separation chamber, applying a direct current voltage to the mixed solution to cause the electrophoresis of the charged substances and to separate them, and withdrawing the charged substances thus separated from outlets disposed at one and the other end of the separation chamber. In a further embodiment, purification or concentration of extracellular vesicles from a biological sample is achieved by iso-dielectric separation techniques.

In another embodiment, purification or concentration of extracellular vesicles from a biological sample is achieved by a field-flow fractionation (FFF) technique. The technique, where extracellular vesicles can be separated by their position in a laminar velocity gradient. In some embodiments, a cross-flow perpendicular to the down-channel flow drives particles toward a particular membrane. Diffusion causes particles to migrate away from the membrane, opposing the cross-flow. Because smaller particles have greater Brownian motion, they migrate farther on average into the bulk flow, which velocity increases parabolically with distance from the membrane. Therefore, smaller particles travel down-channel faster on average than large particles, eluting from the channel at times which correspond to size, with peaks that can be detected and collected as fractions. In this "normal mode" separation, the smallest particles elute first. In some embodiments, the separation of extracellular vesicles using this technique can be performed without any biological capture agents, such as antibodies. While this technique is capable of independent size-based separations, it may also be coupled to affinity methods for increased specificity.

Isolation or enrichment of extravesicles from biological samples can also be enhanced by use of sonication (for example, by applying ultrasound), or the use of detergents, other membrane-active agents, or any combination thereof.

In some aspects, one or more purification steps may involve precipitation-based methods whereby a polymer-containing solution is added to the sample and following a short incubation step, EVs precipitate and form a concentrated pellet.

Preparing the Data (204, 206, 208)

In 204, examples of imputation methods include K-Nearest-Neighbor computation or matrix completion methods such as spectral regularization or the graphical lasso (L1 regularization). The aforementioned imputation methods take as input a data matrix that contains some non-missing and some missing indices, and estimates values for the missing indices by summarizing trends observed in the non-missing indices. Various embodiments may use statistical or computational methods that allow for missing variables, such as random forests, and then separate model fits are not needed. "Fit" here pertains to the final coefficient values assigned to each variable in a model.

In 206, initial input data features from 202 or 204 may be summarized using dimensionality reduction techniques such as principal components analysis, which summarizes the variance of N input variables into a reduced set of K variables, where the user selects K. In some embodiment, another secondary feature set may be clusters, or subgroups, within the broader set of objects measured. Clustering methods, as opposed to predictive methods, identify structural differences between different objects in a dataset, and group objects by these differences. In an embodiment, objects being clustered may be samples, a mixture of measurements from the various data types inputted, or secondary forms of the data types such as nodes in a network or aggregate summary variables.

In some embodiments, feature sets are often pruned (208) both for interpretability, to focus on the most important variables, and also to avoid issues that arise when variables are highly correlated. Highly correlated input variables into models such as linear regression can result in incorrect and unstable models. Much of the work in defining and accurate and useful algorithm is in preparing the final feature set to be used in the actual statistical or computational model that leads to insights and predictions. Example 1 provides an example with several automated feature pruning steps; first, only microRNAs related to an mRNA immune cell signature are retained by the computing system; then, microRNAs from this list are automatically filtered down to only microRNAs that are present in the EV dataset of interest and that also pass a variance threshold to improve the automatic differentiation of EVs between different cell types. Table 5 details the list of microRNAs that passed the automatic statistical filter.

In some embodiments, variable pruning methods include filtering out variables using thresholds, such as removing variables that have low variance across all data points, as they are less likely to provide distinguishing, predictive characteristics. Other approaches include re-running the statistical model several times, changing the number of variables and/or mixture of variables used, and evaluating the fit of the model using a criterion. In an embodiment, a criterion may be Bayesian-based criterion such as the Bayes Information Criterion or Akaike Information Criterion, which evaluate the tradeoffs of complexity and predictive power of a closed-form statistical model. Traditional approaches specific to regression include forward and backward selection, where variables are sequentially added or removed using such aforementioned criterions.

Non-bayesian approaches that can be used to prune down a variable input set include cross-validation, where a small set of the samples are not used to train each of these different variable-model fits. These samples, called the "hold-out" test set, are then used to quantify how well each of the model fits predicted an outcome. The group of variables that best predicted the outcome(s) of interest are kept as the best feature set. Variable pruning can also be implemented during the model fitting process itself for many models via regularization. In regularization, an L1 or L2 penalty (an additional variable constant) is added to the original mathematical model equation. These penalties tend to either "drop"

(set the coefficient to zero) or "dampen" (set the coefficient close to zero) variables during the fitting process.

Inferring Relationships Between Data Types (212)

In some embodiments, the relationships in 212 can be quantified using network-based methods. A network is broadly defined as nodes and edges, where potentially related nodes have edges connecting them. An edge can be represented as simply a continuous weight or a binary status. A node can be any feature or group of features, such as a protein or a gene-protein complex or a particular patient sample.

In some embodiments, as sample-specific data is collected by this system, new nodes and edges can be added and existing nodes and edges can be updated to reflect the new findings from the sample.

In some embodiments, edges and nodes are defined via an adjacency matrix.

In some embodiments, integrating these various data types lends itself to a deep learning or graphical model method, where nodes and their relationships may be defined and learned by optimization of the statistical model, as opposed to being defined solely by existing reference databases. In a similar vein, a decision tree or random forest can also be fit, where each branch of the tree is a relationship.

In some embodiments, these various data types will be clustered to identify relevant subgroups. In some embodiments, exemplary clustering methods are k-means clustering, hierarchical clustering and spectral clustering. Examples 2 and 4 provide examples of how hierarchical clustering can be used to infer relationships between EVs by computing which EVs have the most similar RNA expression levels, defined by the shortest Euclidean distance averaged across all genes used to cluster the EVs. In an embodiment, one or several clustering algorithms are run greater than one time on a resampled data matrix, with or without replacement. The summary of all of these clustering results are aggregated for more robust final clusters; an example of one such method is consensus clustering.

Many clustering methods require the user to select the number of clusters ahead of time using a separate preliminary method; methods to select the number of clusters include the Proportion of Ambiguous Clusters (PAC) score, the Gap statistic and the Silhouette statistic.

Given that a network can be interpreted as an adjacency matrix (defined previously), networks can also be clustered using any clustering method that clusters a matrix. Exemplary clustering methods are described in the previous section; 216 in FIG. 2 shows an embodiment of a hierarchical clustering algorithm that produces a dendrogram visualization to show the groupings of the EV populations. In an embodiment, before clustering, the adjacency method will be pruned to identify only node-node relationships with consistent, existing or highly weighted edges. In one such embodiment, an example pruning method is regularization; one such specification regularization implementation is the graphical lasso, which uses L1 regularization to prune edges in a large sparse matrix. A sparse matrix is a large matrix that contains mostly zero values; sparse matrices can occur in biological data due to a lack of comprehensive data measurements or simply highly specific biological interactions that do not involve most of the other molecular features like proteins, genes or lipids included in the dataset or network.

The edges and relationships between EV measurements and additional variables can also be defined by the final predictive statistical model itself. This is the case for graphical models, neural networks, deep learning methods and random forests.

In some embodiments, the system just uses one data type. In some embodiments, the system adds on a new data type not previously mentioned. In some embodiments, the system stores the data sets in a specific storage system or data schema/format. In some embodiments, the system combines the datasets to understand how the internal genetic material, which can sequence "deeper" than proteins and lipids on a first pass, helps to inform what might be happening on the surface of EVs and what they are interacting with. In some embodiments, the system focuses on one specific EV isolation method or using two specific EV isolation methods to get a better understanding of the EV populations in a sample. In some embodiments, the system emphasizes clustering EV data first, then running a supervised prediction algorithm. In some embodiments, the system uses a single statistical model in the deconvolution model versus a system of models. In some embodiments, the system uses models "vote" (boosting) or resampling and re-running models for robustness (bagging). In some embodiments, the system targets very specific receptors. In some embodiments, the system focuses on different types of diseases.

There are numerous possible EV populations based upon the richness of the data types one can measure on their surface and inside them, but researchers need a tool to assist in deciding which populations exist within a certain sample and are relevant to their scientific and clinical variables of interest.

Even characterizing the surface receptor proteins alone is laborious, as advanced methods such as flow cytometry can only characterize 30 proteins at once. Genetic data, when measured by methods such as RNA or DNA sequencing, can measure tens of thousands of probes at once. Integrating all of the possible data found on the surface and inside an EV provides a richer landscape for both characterizing and understanding EVs.

In various embodiments, the system conducts an unbiased deconvolution of the mixture of these numerous data types, along with provide relevant recommendations to scientists about which EV populations exist in a sample and what clinical and experimental variables of interest they are correlated with. In various embodiments, the system accelerates discoveries for highly accurate, targeted screening diagnostic assays, treatment monitoring and drug target discovery within the context of extravesicles. In various embodiments, because of their prevalence in the body, only a small sample of biofluid (around 250 microliters) is needed to isolate EV using certain isolation techniques. In particular, extravesicles have also been implicated in numerous cancers and neurodegenerative diseases. Thus, by providing recommendations on the specific EV populations to interrogate for specific clinical conditions, this system will enable researchers to quickly identify new approaches for the treatment of diseases using EVs. This system provides an unbiased discovery mechanism for both identifying key EV populations and linking them to diseases for potential therapeutic delivery, therapeutic compound discovery, and diagnostic purposes.

Figure 3:
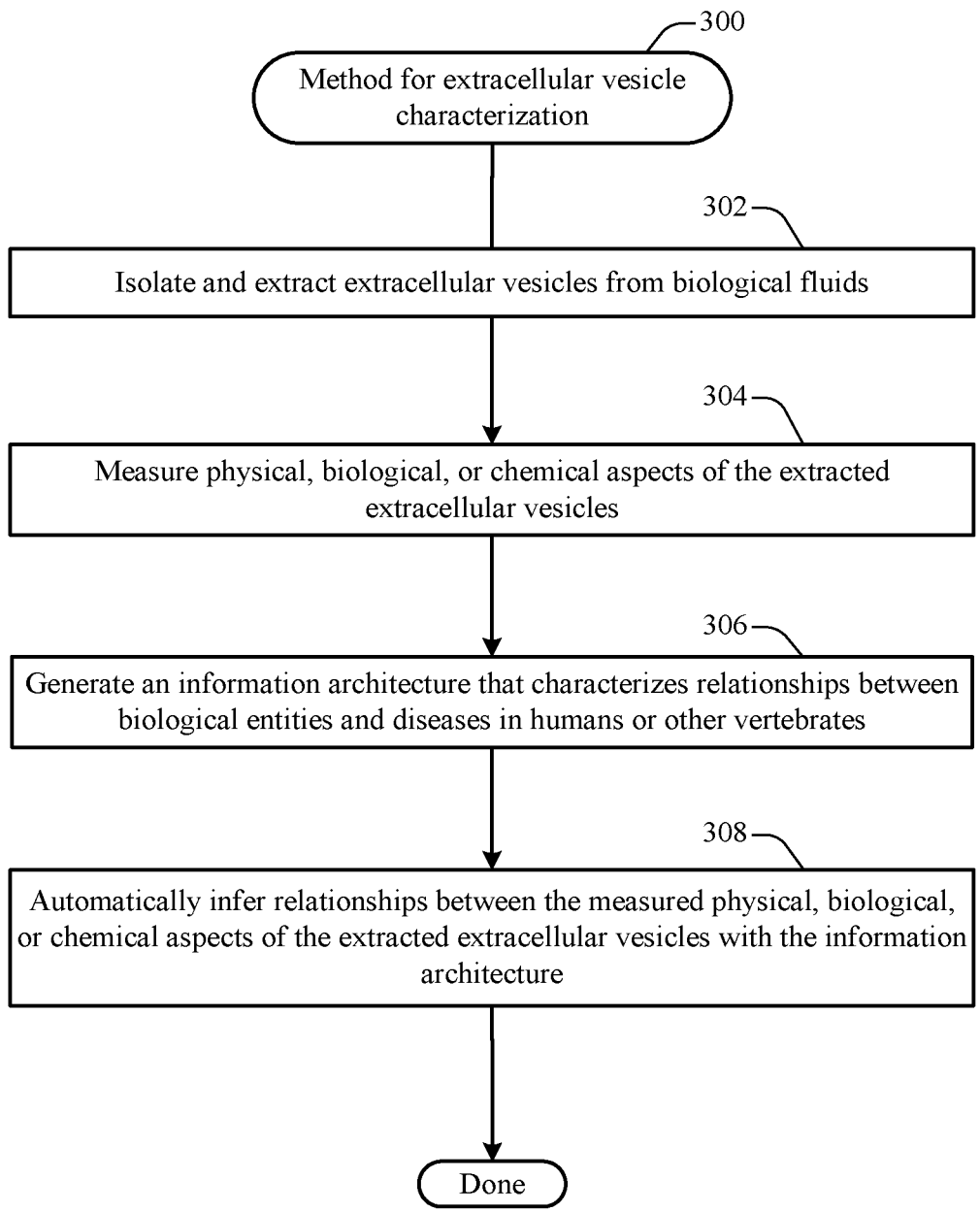

FIG. 3 illustrates a flow chart of an example method 300 for extracellular vesicle characterization, in accordance with one or more embodiments. Method 300 begins with isolating and extracting 302 extracellular vesicles from biological fluids. At 304, the method includes measuring physical, biological, or chemical aspects of the extracted extracellular vesicles. At 306, the method includes generating an information architecture that characterizes relationships between biological entities and diseases in humans or other vertebrates. Last, at 308, the method includes automatically inferring relationships between the measured physical, biological, or chemical aspects of the extracted extracellular vesicles with the information architecture. Such automatic inferring can be conducted by a computer processor. Such inferring can also be performed to characterize or identify the subject, e.g., isolated, EVs as being of a particular size, content, metabolic stage etc., as compared with other EVs or biological content, and/or as being EVs associated with a particular disease condition such as cancer.

In certain embodiments, automatically inferring relationships, such as inferring relationships automatically with a processor, according to the subject disclosure can include inferring relationships between extracellular vesicle-characteristic data, e.g., measured physical, biological, or chemical aspects, of the extracted extracellular vesicles. Examples 2 and 4 provide examples of automatic inference of relationships between EVs based on measured characteristics. In some embodiments, the similarity between EVs is automatically inferred using unsupervised learning, specifically hierarchical clustering. In certain embodiments, automatic inference can also include inferring or identifying relationships between the extracellular vesicle-characteristic data, e.g., measured physical, biological, or chemical aspects, and a known value or values associated with a particular EV-identifying characteristic, such as size, membrane content, intra-vesicular concentration or content, etc., which is indicative of a property of the EV, such as a type, metabolic stage, or a disease condition, e.g., cancer. Example 1 provides an example where automatic processing of gene feature lists using statistics metrics and supervised machine learning methods, specifically support vector machines, are combined in a single system to automatically infer the cell-type from which EV samples were derived. Example 3 provides an example where statistical metrics such as automated differential expression tests between EVs from different patient disease states, and automated computational on intersecting feature lists between in vitro cell culture and human blood models, enable automatic inference of a specific EV population that may be produced by or target cancer cells. The EV characteristics automatically inferred to define the population in this example were EV surface proteins and internal EV genetic material. Such known values can be stored in a database as part of or accessible by the information architecture. In Example 1, the cell type labels were stored in a SQL relational database and the RNA expression matrix of the EV samples were stored in a NoSQL database hosted on cloud servers. The cell type labels, along with the dataset ID and specific sample ID, were stored in a relational database so that the sample ID could be used as a unique key. These unique sample ID keys and dataset IDs were stored in one SQL table, along with a cell type key. This cell type key linked to a second SQL table that contained further information on each cell type, such as B cells and T cells. The further information included cell surface proteins and known biological pathways and diseases related to each cell type. The NoSQL database containing the EV RNA expression matrix stored each EV sample as a column in a NoSQL table; the sample IDs in the NoSQL table were the same as the sample IDs in the relational database to provide a unified data schema from which to enact future SQL queries to return EV measurements, in this case RNA expression, related to specific cells or disease types. In Example 3, patient clinical characteristics linked to the blood samples, such as cancer status, age and gender, were stored in a SQL relational database, and the RNA expression and protein mass spectrometry data were stored in a NoSQL database.

As examples of certain embodiments, the datasets in Examples 1 and 3 were first automatically downloaded and processed on a cloud server, data schemas were designed to hold the relational and non-relational data, and then the data was automatically uploaded to the appropriate database. After automatic inference, model fits and predicted results from both Examples 1 and 3 were stored in NoSQL databases to improve future automatic inferences predicting similar cell types or disease states. As such, the subject architecture can compare measured values with known and/or previously measured values which have already been specifically associated with a particular EV characteristic, such as a characteristic of a disease condition, to determine whether the measured values are the same or different with the known and/or previously measured values. If the values are the same, then the particular EV characteristic, e.g., characteristic of a disease condition, associated with the known and/or previously measured values is then automatically identified as also being associated with the EVs upon which the subject measurements were conducted.

In various embodiments of the methods, automatically inferring, such as automatically inferring with a computer processor, includes comparing characteristic data of extracted EVs with previously categorized EV characteristic data stored in a database to thereby characterize the extracted EVs. In some aspects, the previously categorized EV characteristic data is "known," as described above, and includes EV characteristic identifiers. Such identifiers can be a particular EV-identifying characteristic, such as size, membrane content, intra-vesicular concentration or content, etc., which is indicative of a property of the EV, such as a type, metabolic stage, or a disease condition, e.g., cancer.

In various embodiments, the methods include obtaining EV-characteristic data, which is data of physical, physical, biological, or chemical aspects of EVs. Such data can include any type of EV information referenced herein and can be accessed from a database, such as a public database of the same. Such data can include information on EV size and/or cargo, e.g., membrane and/or intra-vesicular content or molecules otherwise bound to EVs.

Obtaining such data can include conducting measurements of one or more physical, biological, or chemical aspects of EV's. Such aspects can be EV-identifying aspects which can be compared with one another and/or known values and thereby used to identity a specific EV type or class, such as cancer cell EVs. EV-identifying aspects can be any aspects which separate one EV type or class from another. For example, an EV-identifying aspect can be an aspect which separates cancer EVs, such as a specific type of cancer cell EVs from other EVs or biological entities in a sample. Obtaining such data can include detecting the presence or absence of a particular EV cargo type or a molecule bound to an EV.

As provided herein, measuring physical, biological, or chemical aspects of EVs can include measuring EV size and/or characteristics of EV cargo, e.g., membrane and/or intra-vesicular content or molecules otherwise bound to EVs. In some embodiments, the measured aspects of the extracellular vesicles include: vesicle size, vesicle density, vesicle lipid bilayer composition, extravesicular proteins and extravesicular genetic material attached to the vesicles or floating in the surrounding biological fluid, vesicle membrane proteins, intravesicular proteins, intravesicular genetic material, and/or biochemical alterations of any extravesicular or intravesicular genetic material, or any combination thereof.

Conducting such measurements can include detecting the presence or absence of a particular EV cargo type or a molecule bound to an EV. Characteristics measured can include concentration, presence, absence, or identity. For example, measured aspects can be concentration, presence, absence, or identity of intra-vesicular content, such as proteins, nucleic acids, e.g., DNA, RNA, or other molecules. Measured aspects can also be concentration, presence, absence, or identity of a particular type of molecule, e.g., a protein, in the EV membrane. Measurements can be conducted using the following detection methods DNA-seq methylation, DNA array methylation expression, DNA-seq somatic mutation expression, DNA array somatic mutation expression, DNA-seq germline mutation expression, DNA array germline mutation expression, DNA ChIp-Seq expression, RNA-seq expression, RNA microarray expression, single-cell RNA-seq expression, single-EV RNA-seq expression, fluorescence imaging and fluorescent label quantification, nanoparticle tracking analysis (NTA) measurements, EV count measurements, EV size, flow cytometry, mass spectrometry, mass cytometry, protein western blot, enzyme-linked immunosorbent assay (ELISA), and/or single-photon emission computed tomography (SPECT), immunohistochemistry, any resistive pulsing, size exclusion chromatography, zeta potential analysis, protein microarrays, or any combination thereof Furthermore, such measurements can be conducted with an EV-characteristic measuring device. Such a device can include one or more of: a nucleic acid sequencer, a PCR or digital PCR machine, a western blot system, a western blot gel imager, a flow cytometer, a mass spectrometer, a mass cytometer, a nanoparticle tracking analyzer, a zeta potential measurement tool, a fluorescent microscope, a next-generation sequencer, a DNA microarray, or RNA microarray.

In some embodiments, the information architecture stores relationships and attributes of biological entities or diseases as a relational database, a non-relational database, a graph database, lists of attributes in flat files, or any combination of such databases.

In some embodiments, the relationships between biological entities, diseases, and/or their attributes stored in the information architecture may contain different values for different states.

In some embodiments, the measured aspects of the extracellular vesicles are interpreted to have potential relationships amongst themselves.

In some embodiments, relationships between measurement aspects of the extracellular vesicles are represented via a binary decision, thresholding, covariance, variance, distance metrics, or any combination thereof.

In some embodiments, the method further includes comparing the relationships between measurement aspects of the extracellular vesicles, values of the measured aspects between extracellular vesicles, and/or list(s) of key measured aspects in extracellular vesicles, with the relationships and/or attributes of biological entities or diseases stored in the information architecture.

In some embodiments, the method further includes providing recommendations for diagnosis of diseases, treatment of diseases, potential biochemical compounds that may act as pharmaceutical agents, or any other clinical conditions for human or vertebrate healthcare. In some embodiments, providing recommendations includes quantifying a similarity measurement and determining whether the similarity measurement exceeds a predetermined threshold. In some embodiments, additional information linked to the origin of the biological fluids, such as medical history, additional measurements from biological fluids or tissue samples, disease status or therapies administered, is incorporated to improve the accuracy of the recommendations.

Figure 4:
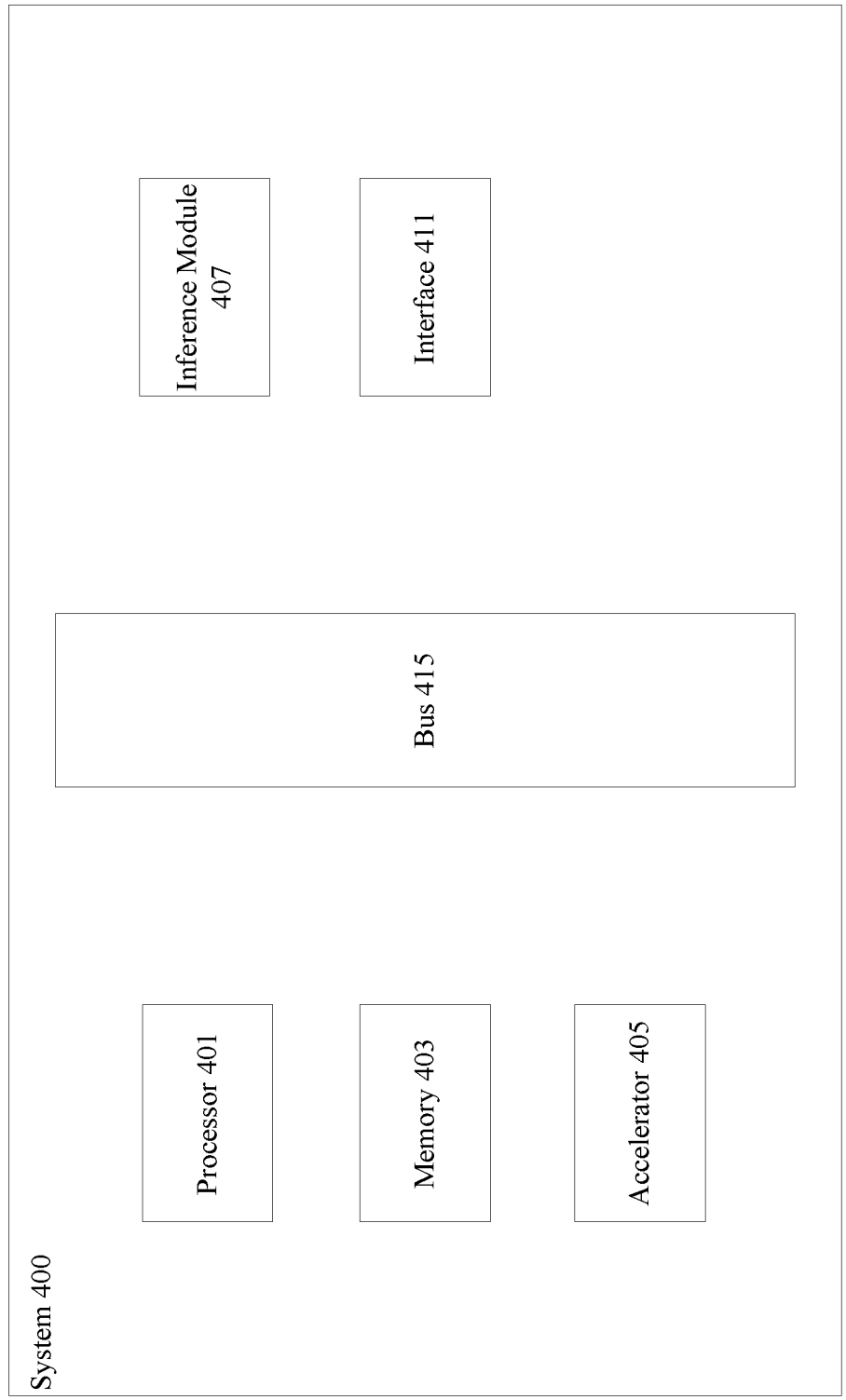

FIG. 4 illustrates one example of a system 400, in accordance with one or more embodiments. According to particular embodiments, a system 400, suitable for implementing particular embodiments of the present disclosure, includes a processor 401, a memory 403, an interface 411, and a bus 415 (e.g., a PCI bus or other interconnection fabric) and can operate as a network server. In some embodiments, when acting under the control of appropriate software or firmware, the processor 401 is responsible for various processes, including processing inputs through algorithms described in the present disclosure. Various specially configured devices can also be used in place of a processor 401 or in addition to processor 401. The interface 411 is typically configured to send and receive data packets or data segments over a network.

In some embodiments, system 400 further includes inference module 407 configured for extracting and determining a correlation between measured aspects of extracellular vesicles and an information architecture, as described in more detail above. Such an inference module 407 may be used in conjunction with accelerator 405. In various embodiments, accelerator 405 is an additional processing accelerator chip. The core of accelerator 405 architecture may be a hybrid design employing fixed-function units where the operations are very well defined and programmable units where flexibility is needed. In some embodiments, inference module 407 may also include a trained neural network, or other machine learning algorithmic model, to further identify correlations.

Particular examples of interfaces supports include Ethernet interfaces, frame relay interfaces, cable interfaces, DSL interfaces, token ring interfaces, and the like. In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the system 400 uses memory 403 to store data and program instructions for operations including training a neural network, object detection by a neural network, and distance and velocity estimation. The program instructions may control the operation of an operating system and/or one or more applications, for example. The memory or memories may also be configured to store received metadata and batch requested metadata.

Because such information and program instructions may be employed to implement the systems/methods described herein, the present disclosure relates to tangible, or non-transitory, machine readable media that include program instructions, state information, etc. for performing various operations described herein. Examples of machine-readable media include hard disks, floppy disks, magnetic tape, optical media such as CD-ROM disks and DVDs; magneto-optical media such as optical disks, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

In some embodiments, advantages provided by the system and methods described above include the ability to automatically infer a correlation of a disease or condition based on extracted extracellular vesicles. As a result, existing computer functions are improved because processes are trained to more accurately infer correlations than standard or generic computers.

In addition, in some embodiments, the system includes an additional inference module that may include a neural network trained to further increase accuracy of correlation and processing speed. In some embodiments, the accelerator provides a specialized processing chip that works in conjunction with the inference module to compartmentalize the processing pipeline and reduce processing time and delay. Such accelerators are specialized for the system and are not found on generic computers.

The foregoing description, for purpose of explanation, has been described with reference to specific embodiments. However, the illustrative discussions above are not intended to be exhaustive or to limit the present disclosure to the precise forms disclosed. Many modifications and variations are possible in view of the above teachings. The embodiments were chosen and described in order to best explain the principles of the present disclosure and its practical applications, to thereby enable others skilled in the art to best utilize the present disclosure and various embodiments with various modifications as are suited to the particular use contemplated.

Utility

It is important to be able to accurately characterize EV populations, for example, to understand how they correlate with clinically relevant variables such as disease state, therapeutic drug target selection and therapy monitoring. However, EV populations are currently poorly characterized, preventing accelerated discovery of populations that are key to these relevant scientific and clinical variables.

The possible number of EV populations quickly explodes when one considers all of the possible permutations of EV external and internal features, but a tool does not currently exist to assist in deciding which populations exist within a certain sample and are relevant to their scientific and clinical variables of interest. Scientists cannot easily continually re-analyze the same sample, or analyze massive numbers of samples, to obtain a comprehensive dictionary of which specific external EV data types such as receptors are linked to which specific internal EV data types such as RNA expression levels. Even characterizing EV surface receptor proteins alone is laborious, as advanced methods such as flow cytometry can only characterize 30 proteins at once.

Computational methods have aided scientists and clinicians in other fields to pinpoint which biological and clinical populations are of interest and warrant the time and expense of traditional wet lab experiments, but these methods are currently lacking in the field of EV discovery and characterization. It has been attempted to characterize patient groups using a limited, small set of EV populations selected solely by one to a handful of membrane proteins, but not to broadly characterize possible EV populations in an unbiased fashion.

In view of the above, there is a need for systems and methods such as those disclosed herein that accurately characterize EV populations found in patient biological fluids in order to aid disease analysis and treatment.

EXAMPLES

The following examples are put forth so as to provide those of ordinary skill in the art with a complete disclosure and description of how to make and use the present disclosure, and are not intended to limit the scope of what the inventors regard as their present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Figure 5:
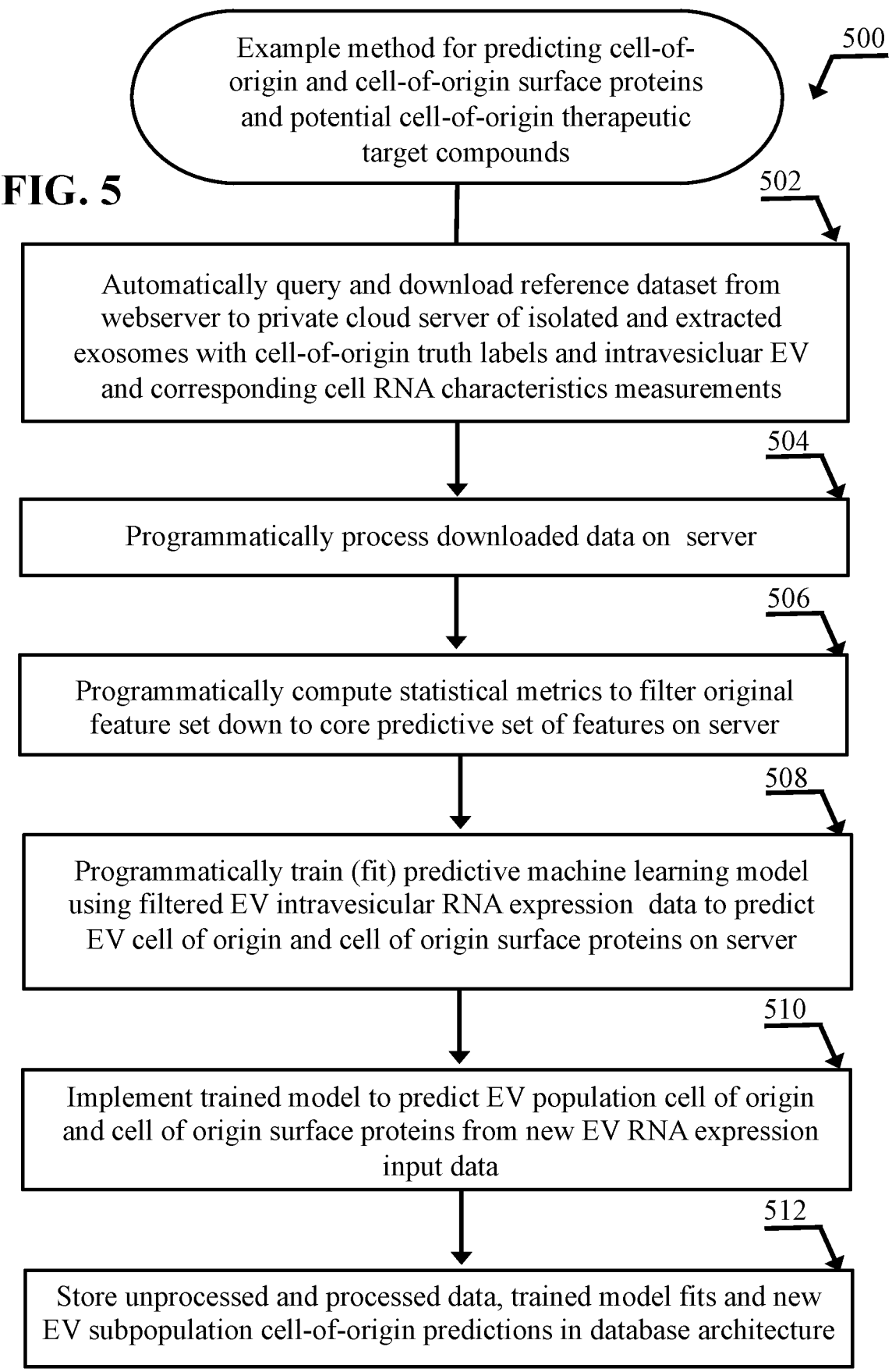

EV cell-of-origin and cell surface prediction identified potential EV populations for cell-specific targeting. FIG. 5 illustrates a specific exemplary implementation of the general system described in FIG. 1 and a specific exemplary implementation of the general method described in FIG. 3. Method 500 was implemented via automatic querying and downloading of a dataset from a reference database, Gene Expression Ombnibus (GEO). This data was then automatically processed and normalized on a computing server using methods 504. A key set of features, in this case, genes is programmatically deduced based on the statistical filtering method 506; the exact list of such features in this embodiment can be found in Table 5. In some embodiments, further processing as described in 502 and feature set reduction in 506 may not be necessary where this work has been completed by an external party that then uploads the dataset to a web server reference database where other parties can query and download the dataset. A supervised machine learning algorithm 508 is then trained using the data after filtering using the 506 feature set. The trained machine learning algorithm is used in 510 to predict EV subpopulation characteristics, in this case the cell of origin, and then in 512, the processed training data, trained model, and predictive results are stored in a noSQL database to improve future predictions on new EV input characteristic data and improved future model training. This overall method illustrates how EV isolation, extraction and/or EV characteristic measurements can be completed by an external group or party. The goal of this method is to predict which cells may have produced the EVs whose characteristics have been measured. Because the cells used to train the model contain distinct surface proteins, this method thus also indirectly predicts cell surface proteins certain EV subpopulations may be interacting with. Predicting the specific cell type, and its surface proteins, that the EV may have been generated from is critical to understanding how the EV may be used to interact with and target certain cells. Because EVs are used in cell-to-cell communication, these predictions also allow for correlation of certain EV measurements, such as RNA expression, with cell activity. These correlations can be used to deduce potentially novel therapeutic compounds related to the activity of a specific cell type.

Data Collection Methods (502)

The dataset, in its raw, unprocessed form, was searchable programmatically via a web API. A function was called using the R computing language that took as inputs controlled keywords, specifically MeSH terms, a controlled medical and biomedicine terminology consisting of approximately 26,000 words. The raw dataset had been stored with MeSH terms relevant to the origin of the data, in this case, immune cells and extracellular vesicles. The R function used "immune", "extracellular vesicle", and "microRNA" as inputs, and returned the dataset ID for the dataset used in this example, specifically GSE27997. A second R function used this dataset ID as an input to produce a REST API call to the remote web server containing the dataset. This REST API call instructed the web server to begin downloading the raw dataset to the cloud server from which this second R function was implemented. The cloud computing server architecture that ran both of the above R functions was implemented using the Linux operating system, specifically Debian. The script that called these R functions was run inside a virtualized container system, Docker, with R version 3.0.4.

The downloaded datasets, GSE27997, was created by isolating and extracting EVs using ultracentrifugation. EVs were then lysed, and the RNA inside the EVs, specifically small RNAs in this example, was measured measured using a microarray designed to detect small RNAs. This dataset was automatically recommended by the first R function described above not due to the specific EV isolation and extraction methods, nor the RNA measurement methods, or the type of RNA feature (small RNAs) measured. The dataset was isolated because the EVs were isolated from specific cells cultured in vitro, and thus the MeSH terms linked to the raw dataset on the webserver included cell-specific terms like "B cell" and "T cell", and also RNA-specific terms such as "microRNA". In addition to measurements of RNA expression from inside the EVs, the RNA expression from cells was also measured to allow for comparison of EV versus cell RNA expression from the same cell type. Three types of immune cells were used: CD4+ T cells, B cells and dendritic cells. Thus, predicting cell type from this dataset also inherently predicts known cell surface proteins, such as CD4 from the CD4+ T cell line.

Data Processing Methods (504)

The EV and cell small RNA expression data downloaded via the REST web service API call produced by the second R function described above contained separate files for each EV sample, and each cell sample, from the three distinct cell type cultures, with 2-3 replicates for each state (EV versus cell, and the cell type). Using the R computing language, an automated script was run that concatenated the raw RNA expression files together and conducted statistical background correction and quantile normalization on the raw RNA expression values. This R script consisted of a function that first read in each individual raw RNA file and read in the mean signal value column. These raw files were in Agilent format, and thus the R function to read in each file scanned for the correct column name, in this case "gMeanSignal". Once a file was read into the computing system as an R data matrix, matrix indices with extremely large raw values, in this case above 60000, were imputed to the average value for that gene across indices below the set threshold of 60000. This imputation step was not implemented to correct for missing values, but rather to avoid computational errors when running the quantile normalization process, which cannot run with extremely large variances across matrix index values. Values above 60000 in this dataset example were extreme outliers compared to the rest of the dataset. After this step to remove extreme outlier values, an R function concatenate all files together, to produce an R data matrix with gene symbols (small RNAs) in the rows, and sample IDs (each one being an EV or a cell sample) in each column. Another R function then took this concatenated matrix as an input, and normalized across all files using the Robust Multi-Array Average (RMA) procedure, which is a form of quantile normalization. This method normalizes across samples so that the gene expression values across all samples fit within shared quantiles. Finally, the RNA expression values matrix outputted by the RMA normalization output function were logged to approximate a normal distribution. The final processed output of the data processing module (504) resulted in 706 rows (miRNA genes) in the matrix and 16 samples (columns) with logged expression values.

Feature Set Pruning (506)

This list of 706 genes, considered the original feature set, was then reduced to a final feature set used for the model training detailed in part 508. Feature set reduction was implement because not all genes were highly correlated related to the cell type of origin labels labels, which is what the model was designed to predict. This feature set will be denoted as the "EV-derived" feature set; details on how this feature set was derived are provided in the subsequent paragraph. A different feature set, based off of known immune cell mRNAs, listed in Table 1, was first used to fit the model. This feature set will be denoted as the "cell-derived" feature set. The "cell-derived" feature set was first used because although for both model fits, EV RNA expression was used, the goal of the model was to predict cell types. Thus, it was hypothesized that using a feature set derived from immune cell mRNAs might result in a model with a high prediction accuracy for cell type. Because Table 1 is mRNAs, and the EV RNA expression contained predominantly small RNAs, specifically microRNAs, the immune-cell-derived mRNA gene signature list in Table 1 was automatically translated into microRNAs predicted to regulate these mRNAs. A list of 2,562 microRNAs, shown in Table 2, hypothesized to regulate the mRNAs from Table was created by producing an API call to a web server that contained a database of mRNA-microRNA relationships. These relationships were quantified via natural language processing algorithms. These algorithms used as inputs scientific and medical text from publications, and parsed sentences contained both an mRNA and a microRNA. The parser inferred whether the microRNA might regulate the mRNA if the sentence contained words such as "regulated by" or "transcribed by". Because the function of many microRNAs is still considered exploratory research, oftentimes, many microRNAs are returned as potential targets for a single mRNA, and thus Table 2 contains more RNAs than Table 1. Table 3 lists the 273 of these 2,562 microRNAs that were also present in the GSE27997 706 starting gene feature matrix; this final intersecting gene feature set is the "cell-derived" gene feature set used in the first modeling training attempt described in part 508 of FIG. 5.

The "EV-derived" feature set was derived directly from the original 706 genes in the starting processed RNA expression matrix, listed in Table 4. The "EV-derived" feature set was derived by identifying the genes from the original list of 706 microRNA genes in the matrix that differentiated between the three cell types, using solely EV (not cell) RNA expression, with a multiple hypothesis adjusted p-value of 0.05 or lower. This resulted in 105 final microRNA genes, listed out in Table 5; "q-value" in the second column in Table 5 is the multiple hypothesis-adjusted p-value in terms of percentage. This feature set will be termed the "EV-derived" gene feature set henceforth. In this example, an R function took as input the entire processed EV RNA logged expression matrix with 706 genes in the rows and EV samples in the columns, along with a vector that denoted the cell type each EV sample originated from. Then this R function implemented a multiclass nonparametric Wilcoxon rank test, and tested against the null hypothesis that the different cell types did not affect the ranking of each gene by its expression level. To reduce the chance of reporting false positives, the R function then adjusted for multiple hypotheses (testing multiple genes at once) using permutation-based tests to approximate a null distribution. Null datasets to compute the statistical test were created by permuting the cell-of-origin-labels and the microRNA expression data. See FIG. 6 for an illustration of how this "EV-derived" feature set automatically infers distinct RNA expression patterns by cell type of origin.

Predictive Model Training (508)

A dataset of EV measured characteristics with labels linked to states or outcomes of interest is then used to train a predictive machine learning model. In this case, the states are the different cell types of origin: T cell, B cell or dendritic cell. The model trained in this specific example is a Support Vector Machine with a linear kernel, of type nu-regression. An R computing script automatically run on a server was used to fit the model. An R function took as input the full EV RNA expression training matrix, the vector of EV RNA expression for the "new" EV sample being predicted, the cell of origin labels, and the nu parameter level to be used in the support vector nu-regression fitting. The R function then computed a support vector machine regression, where the "new" EV RNA expression vector is regressed against the EV RNA expression training matrix. The prediction of the cell type or cell types present in the "new" RNA sample were computed by the R function as such: the coefficient vector from the output support vector machine was multiplied by the support vectors, using linear algebra multiplication notation in R, to create a modified coefficient vector. To scale the cell fraction predictions to sum to 1, or 100%, the resulting modified coefficient vector was divided by the sum of the modified coefficients. The function returned the predictional fractional amount of each cell type that contributed to the EVs present in the input sample, thus inferring the cell-of-origin of EVs. Tables 6-12 provide examples of such predictions. Thus, each time a new EV sample was predicted, the entire support vector machine regression process was re-run with the same full input EV training matrix, but with a new EV sample to be predicted. The nu parameter was optimized by running this R support vector machine fitting function over a range of nu input parameters, from 0.1 to 1.0. The nu parameter that produced the highest prediction accuracies in prediction the true cell-of-origin label for each test EV sample was selected; the optimal nu parameter value for this model and training dataset was 0.25. Finally, this entire fitting process was done six times. It was done with three feature sets: once, with the "cell-derived" feature set of genes, second, with all 706 of the original RNAs in the GSE27997 matrix, and third, with the "EV-derived" feature set of genes, to compare how the different feature sets affected prediction accuracies. Finally, for all three feature sets, predictions of cell fractions were computed using the RNA expression from EVs, and then the RNA expression from the corresponding cells. Predictions from cell RNA expression was also tested as a comparative baseline, given the EV population "proxy" here being predicted is indeed cell type of origin.three cell states. The Prediction rates for the model fits are reported in Tables 6-12. Two methods for evaluating predicate rates were used: In one case, the model was fit using just one replicate from each cell-of-origin, and then the model was used to predict the cell-of-origin of the other replicates. These rates were estimated using four different fits as a result of using two different feature sets on first EV and then cell RNA expression data. The two feature sets used for each model instance were the "cell-derived" and then the "EV-derive'" feature set. A 0% training error (the highest possible success rate) in each instance would be a predicted fraction of 1 assigned to the true cell-of-origin type of that input replicate. These training predictions are presented in Tables 6-12. The results in Tables 6-12 demonstrate that the 'EV-derived' feature set (Table 8) outperforms the entire original 706 feature list (Table 6) and the 'cell-derived' feature list (Table 7) in that the model predicts the EV cell of origin with higher accuracy from EV RNA expression. The 'EV-derived' feature list also performs well using cell RNA expression (Table 8); suggesting that EV-level characteristics such as RNA expression can be used to both glean insights on EV subpopulations and their respective cells of origin and potential the cells the EVs are interacting with.

Figure 6:
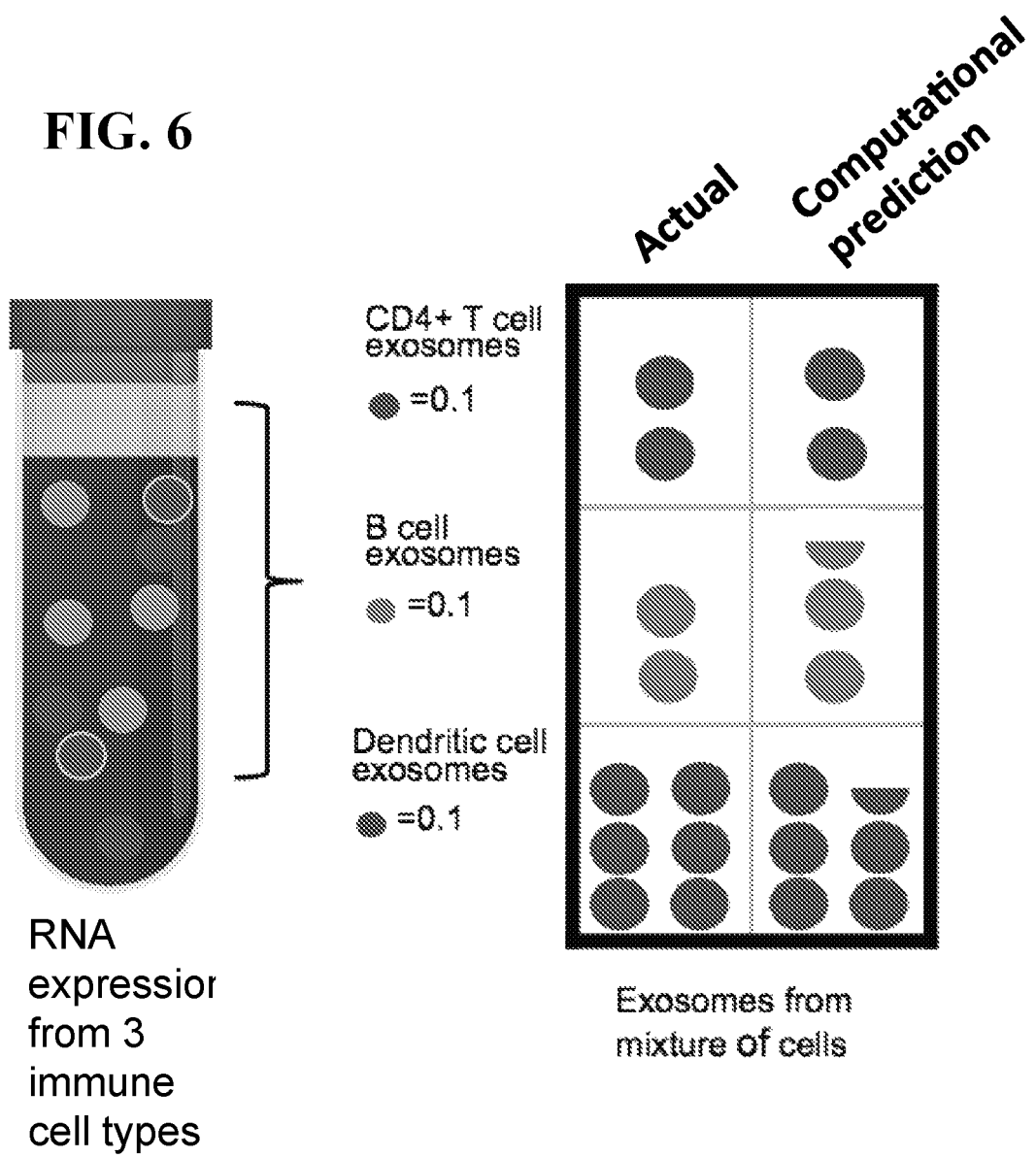

In the second method for evaluating prediction rates, simulated mixed fraction cell-of-origin cell types were predicted by pre-defining the fraction of contribution of each cell-of-origin cell type and summing the weighted contribution of the RNA expression from each replicate to constitute a simulated sample. The results in Table 12 show promising prediction results on the now more challenging prediction problem of samples with mixed cell-of-origin as to a pure single cell of origin, both for EV and cell-based RNA expression model fits. FIG. 6 is a simplified schematic of the results of a single sample prediction detailed in Table 12. It is a visualization representation of the prediction fractions.

The processed data, model fits, and predictions are then stored for future programmatic optimization of the EV characterization system. In this example, the data was stored in a NoSQL database to allow for flexible storage of the processed data matrix as a single table. The predictions were also stored in a NoSQL database, but a graphical database is also amenable to the storage of such predictions for easy query and retrieval when comparing predictions across different conditions or diseases, to discern how the prediction states may be related.

Simulating mixtures of three cells still does not capture the true heterogeneity found in human blood, let alone in vitro samples. In this in vitro case, however, the cell lines also produced exosomes that are known to have at least one distinct surface protein, such as CD4+ on the Jurkat cell line, that are not found in the other two cell lines. Each cell line itself produces a heterogeneous mix of cells, and EVs, with various surface protein markers, but including protein surface marker data would, in a noisier setting, help a machine learning algorithm broadly bucket the extracellular vesicles into broad groups. The RNA expression further helps refine subgroups within these broader groups, linking the extracellular vesicles back to tissue or cell-of-origin, their cell or organ destination, and their functional role.

Shared RNA expression between different isolated populations of extracellular vesicles, as defined by their surface proteins or simply being isolated from patients, animals or cell lines of a different disease type, also creates the opportunity infer shared functional relationships between exosome subgroups/populations beyond just a crude cell surface protein match. These type of functional relationships between extracellular vesicles, cells, organs and diseases are stored in a relational or graphical database to help continue to make inferences on new disease datasets where extracellular vesicle populations are not defined yet.

Example 2

Figure 7:
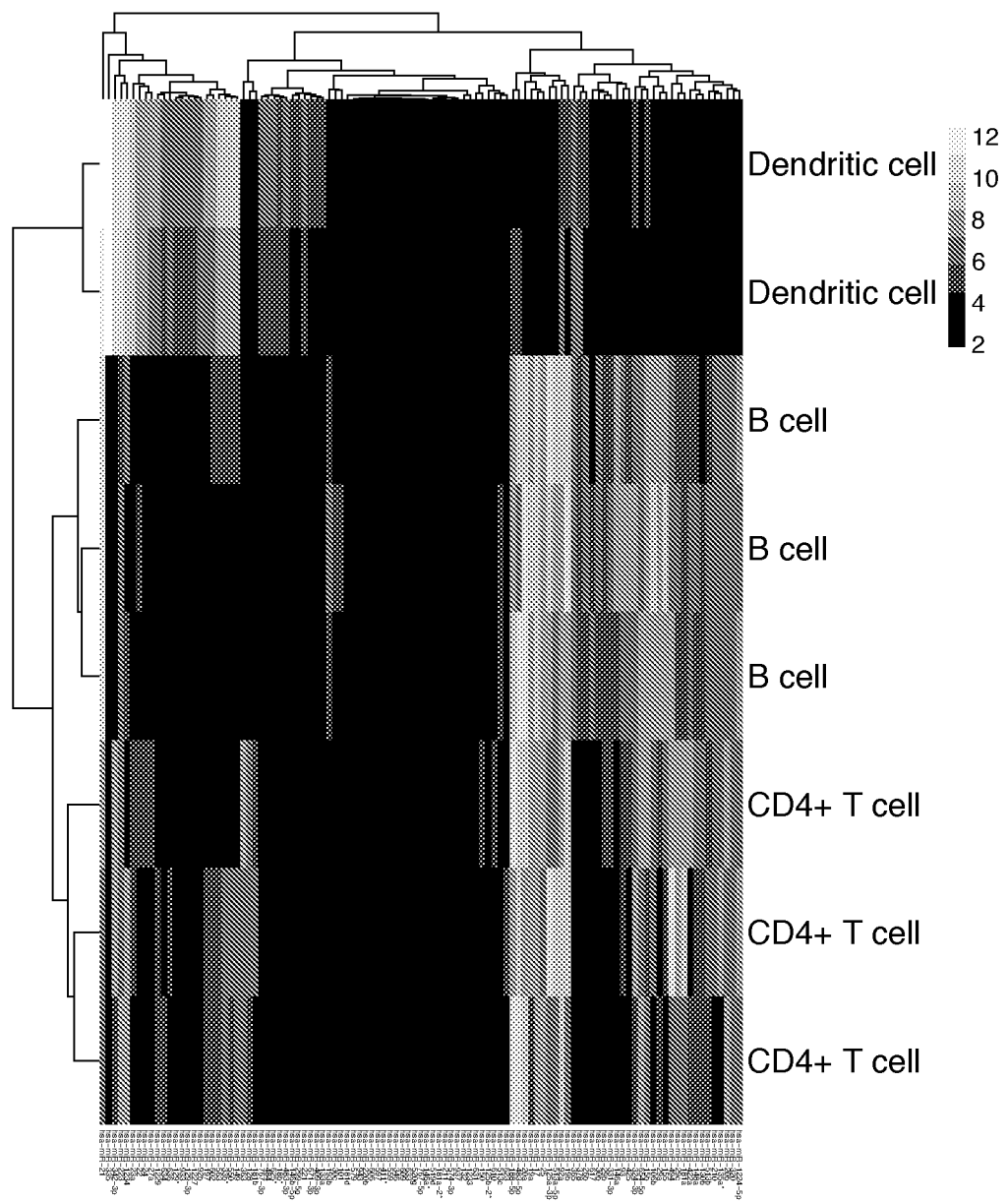

FIG. 7 details an unsupervised learning approach to the EV RNA expression data used in Example 1 using the 'EV-derived' feature set. The cell type each exosome sample was derived from is on the y-axis, and microRNA genes (listed in Table 1) are on the x-axis. The EV samples are clearly clustered in an automatic an unbiased fashion using hierarchical clustering with a Euclidean distance metric by cell-of-origin type. This result suggests that clustering EVs using measurements of their characteristics can provide biological relevant EV subtypes related to biological functions such as cell signaling. The legend is logged RNA expression values.

Example 3 embodiment of the general system described in FIG. 1 involves incorporating EV characteristics from human samples and EV characteristics from cell culture samples from the same disease state into statistical algorithms to identify a novel and robust EV subpopulation defined by its internal genetic content and external surface proteins. FIG. 8 outlines this implementation.

Figure 9:
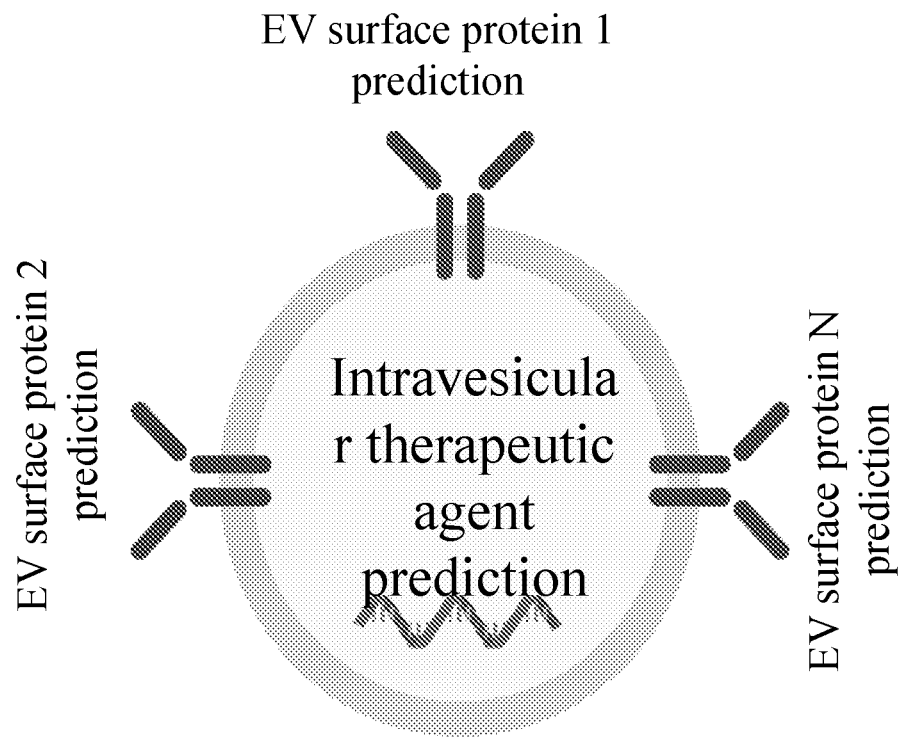
FIG. 9 is a schematic of an example output (recommendation) of the implementation of the system from FIG. 8: an automatically predicted EV therapeutic compound delivery vehicle and possible companion intravesicular therapeutic agent according to the subject embodiments.

In this specific embodiment of the system (800), EVs were isolated and extracted using precipitation-based columns for EV concentration. In another embodiment, the isolation could have been completed using other EV isolation and extraction methods such as sucrose density gradient columns, microfluidics-based isolation, or ultracentrifugation. The embodied system included EV isolation and extraction, RNA-seq on intravesicular RNA 806, identification of statistically significant genes in EVs from human blood samples 808, and programmatic searching for concordant gene signaling patterns in cell culture models mimicking the patient states in 810. The implementation then incorporated EV mass spectrometry by automatically downloading it from a reference database via a web server. The mass spectrometry data was from EVs from cell culture of the same or biologically similar cell line types in 810 to identify proteins in the mass spectrometry data linked to the statistically significant genes. In this system embodiment resulted in both EV surface and internal proteins predicted to be related to a disease or biological state, and internal genetic material that may be crucial to disease signaling. In step 812, the EV protein data can be used to predict surface proteins on EVs that may provide targeted drug delivery vehicles and the intravesicular genetic proteins provide hypotheses about what genetic material should be blocked or amplified, in the case here of RNA, possibly a related siRNA for blocking or possibly a related miRNA knockdown for amplification. The schematic of this final EV subpopulation prediction is shown in FIG. 9. The three y-shape objects in the membrane represent different EV membrane proteins, and an example nucleic acid as a therapeutic agent is depicted inside the EV membrane. Finally, in 814 the results were stored in a database for programmatic querying and improvement of future EV subpopulation prediction, verification, and correlation to specific disease, toxicity or therapeutic states.

Sample Collection and EV Isolation and Preparation (802)

Human blood samples were purchased through a private vendor following standard IRB protocols. Blood samples from four non-small cell lung adenocarcinoma cancer patients (labeled as 'Cancer' in FIG. 10) and three patients presenting with benign tumors (labeled as 'Healthy' in FIG. 10) were used for this analysis. Another implementation could use samples from another cancer such as renal cell carcinoma, ovarian cancer, blood cancer such as leukemia, melanoma, glioblastoma, brain cancer, or a neurodegenerative non-cancer disease state such as Alzheimer's disease, Parkinson's disease, amyotrophic lateral sclerosis (ALS), prion disease, synucleinopathy, Dementia, or Huntington's disease, or an autoimmunity or autoinflammatory disease such as Systemic lupus erythematosus, rheumatoid arthritis, multiple sclerosis, or inflammatory bowel disease, or a rare disease such as lysosomal storage disease, or Usher's disease, spinal muscular atrophy, or acute myeloid leukemia. The EV isolation from human blood samples was conducted by an external vendor for private use, while the EV isolation from cell culture samples was conducted in a private internal lab, showing that the actual EV isolation before measurement of EV characteristics can be conducted in conjunction or in isolation from the system and methods described in the patent.

EV Measurements (804)

RNA-seq was then conducted on the intravesicular RNA from EVs. The RNA-seq from the human blood EV data was prepared using an immunoprecipitation method to isolate and extract the EVs. The EVs were then lysed and their RNA was measured using an RNA-seq library kit targeting small RNAs. The RNA-seq from cell culture EV data was prepared by isolating EVs using a microfluidics-based method that captures EVs via immunomagnetic beads attached to antibodies. In this case, CD9 antibodies were used to capture EVs with CD9 on their surface; CD9 is a surface protein involved in many EV biological processes and thus present on the surface of most EVs. The EVs were then lysed and the RNA inside the EVs was measured using an RNA-seq library kit that provided targeted sections of coding RNA. Both of the library kits mentioned above transcribed RNA into cDNA, which was then fed into a next-gen sequencer that fragmented the cDNA and measured the cDNA sequences of each fragment. The sequencer outputted raw RNA-seq files containing these sequences.

EV Data Processing and Feature Selection (806-808)

Figure 10:
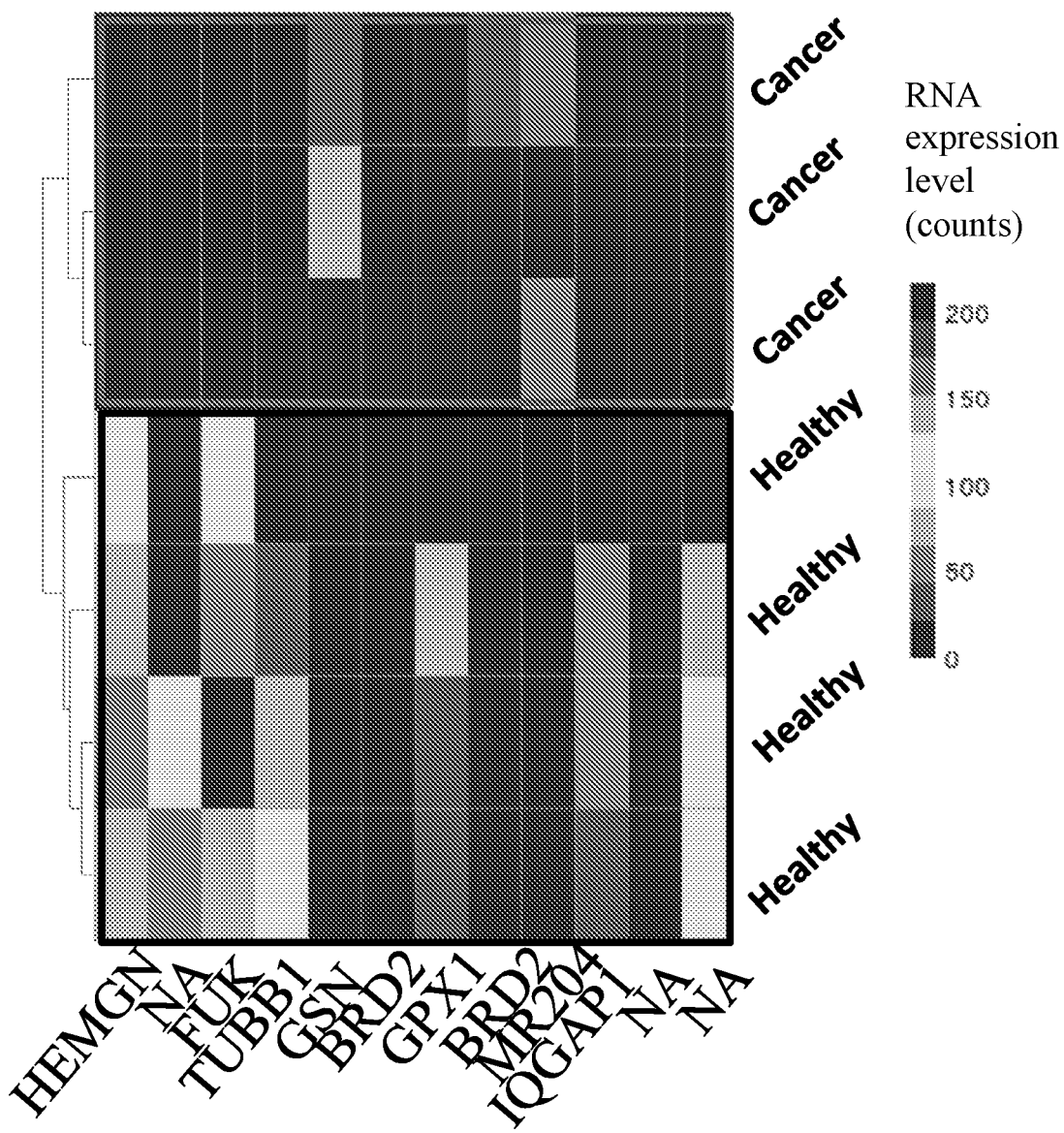
FIG. 10 is a clustering analysis of EV RNA expression from human blood from healthy and from lung cancer patients according to the subject embodiments.

Raw RNA-seq files were aligned to the human genome and RNA transcript counts quantified at the gene level using the STAR alignment algorithm using standard settings suggested by the ENCODE consortium Overexpression genes. Another implementation of this example could do RNA transcript count quantification and the isoform level, and a different alignment algorithm could be used. The count data from human blood EVs was then grouped in the cancer versus healthy patients, and genes found to be statistically significantly overexpressed in the cancer patients were programmatically stored in a database. The method to discover the statistically significant genes was comparable to the methods used in Method 1 to obtain the 'EV-specific' gene list. The heatmap of RNA counts using this statistically significant gene list in human EV blood samples is shown in FIG. 10. HUGO gene symbols that strongly differentiate between healthy and lung cancer patients are on the x-axis; an NA denotes that there is no current gene symbol for the transcript location identified through the ensemble database.

FIG. 11 visualizes the heatmap of RNA counts using this statistically significant gene list in lung cancer and normal cell culture EV blood samples from FIG. 10. The same gene symbols as in FIG. 10 are listed on the x-axis. The order of genes on the x-axis is different in FIGS. 10 versus 11 because FIGS. 10 and 11 are outputs from different clustering analyses. The specific cell lines used were A549 and HEK293, but other implementations could use different cell lines and cell types to illustrate the effect. The goal here in this step is to identify genes that are overexpressed in the same direction in both human blood and cell culture models, to aid in identifying in vitro therapeutic models that mimic real human biological states. One gene, IQGAP1, was statistically significantly overexpressed in both the human blood and the lung cell culture EV samples.

Incorporation of Additional Types of EV Measurements (810)

Mass spectrometry data, automatically downloaded from a reference web server database, was then used to confirm that the protein transcribed by IQGAP1, the Ras GTPase-activating protein, is indeed nonzero in EVs from the exact same lung cancer cell line type as used in the EV cell culture RNA-seq data in FIG. 11. FIG. 12 displays the heatmap of the protein levels for this protein across a National Cancer Institute (NCI) cancer cell line panel containing 60 cell lines, termed the 'NCI 60' panel. The row containing the A549 lung cancer cell line is outlined in black as this same cell line was used for the analyses that produced FIGS. 11, 13 and 14. The full list of cell line names, each denoted by a row in the figure, are: NCI H226, NCI ADR, RES, Colo205, M14, MDA, MB468, KM12, SW620, HOP92, NCI H522, CAKI, NCI H322M, UO 31, HS 578T, ACHN, X 786O, SK MEL28, EKVX, SF539, HOP 62, MALME 3M, SR, OVCAR 3, HCC 2998, MDA MB435, SK MEL 2, SNB 75, OX IMVI, K562, RPMI 8226, NCI H23, IGROV1, SF295, HT29, UACC 257, SNB 19, HL 60, OVAR 4, HCT 116, UACC 62, OVCAR 5, BT549, SK MEL5, A549, U251, MOLT4, MCF7, OVCAR8, MDA MB23, T 47D, SN12C, RXF 393, TK 10, SK OV 3, PC 3, SF 268, A498, CCRF and CEM. This step highlights that because EVs contain multi-omics characteristics such as proteins and genetic material, the system and methods can be used to infer EV subpopulations using more than one data type/EV characteristic.

The final prediction, of which a general schematic is provided in FIG. 9, was a specific EV subpopulation, or type of EV, with a minimum one specific EV characteristic. It may be multiple EV characteristics; in this specific example, the EV subpopulation contains at minimum the intravesicular or EV surface protein Ras GTPase-activating protein and the IQGAP1 RNA. This targeted delivery vehicle could be used to target lung cancer by engineering an EV in cell culture to contain the GTPase-activating protein, without or without the intravesicular IQGAP1 RNA. Any internal 'payload' or compound(s) of choice could be paired with this EV protein characterization. In addition, multiple proteins and/or multiple RNAs may be used to predict an EV subpopulation by the system.

This predicted EV subpopulation was then stored in a database; as multiple samples from different in vitro and in vivo models and human blood disease states are measured, the system can then compare across previous results to determine trends of EV subpopulations across biological states with similar shared pathways or biological characteristics.

Example 4

Provided in FIGS. 13 and 14 are clustering analyses of RNA from cells, and from isolated extracellular vesicles. The embodiment of Figure uses a pre-established gene list of approximately 1300 known cancer genes curated from tissue data.

As provided in FIG. 13, 'exo' denotes the RNA was from an exosome, and 'cell' denotes it was from cells. A459 denotes a lung cancer cell line, SKBR3 denotes a HER2+ breast cancer cell line, Hu78 denotes a T cell lymphoma line, 'mixed cancer cells' denotes a mixture of NCI60 cancer cell lines, MDAMB468 denotes a triple-negative breast cancer cell line, Jurkat denotes a T cell leukemia cell line and HEK293 denotes a non-cancerous embryonic kidney cell line. All cell lines are derived from human cells. Note how the clustering, when using the cancer gene list, is complex—the two lung exosome samples are split apart, and the two normal exosome samples are in a main cluster on the right with one of the lung exosome samples.

The embodiment as illustrated in FIG. 14 uses an unbiased gene list that is purely based on the genes that have the highest variance amongst the samples. In this example, the lung exosomes are closer together, and the normal exosomes are clustered together. The breast cancer cell line on the left, mdamb, is a triple-negative cell line. A459 denotes a lung cancer cell line, SKBR3 denotes a HER2+ breast cancer cell line, Hu78 denotes a T cell lymphoma line, 'mixed cancer cells' denotes a mixture of NCI60 cancer cell lines, MDAMB468 denotes a triple-negative breast cancer cell line, Jurkat denotes a T cell leukemia cell line and HEK293 denotes a non-cancerous embryonic kidney cell line. All cell lines are derived from human cells.

Although the present disclosure has been described in some detail by way of illustration and example for purposes of clarity of understanding, it is readily apparent to those of ordinary skill in the art in light of the teachings of this present disclosure that certain changes and modifications can be made thereto without departing from the spirit or scope of the appended claims. It is also to be understood that the terminology used herein is for the purpose of describing particular embodiments only, and is not intended to be limiting, since the scope of the present disclosure will be limited only by the appended claims.

Accordingly, the preceding merely illustrates the principles of the present disclosure. It will be appreciated that those skilled in the art will be able to devise various arrangements which, although not explicitly described or shown herein, embody the principles of the present disclosure and are included within its spirit and scope. Furthermore, all examples and conditional language recited herein are principally intended to aid the reader in understanding the principles of the present disclosure and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present present disclosure, therefore, is not intended to be limited to the exemplary embodiments shown and described herein. Rather, the scope and spirit of present disclosure is embodied by the appended claims.

What is claimed is:

1. A method of extracellular vesicle (EV) characterization which predicts whether the EV originates from any one of a B cell, CD4+ T cell, or dendritic cell, the method comprising:
   a. obtaining miRNA measurements from extracted EVs having known cell origin at least 1 sample measured is from each of B cells, CD4+ T cells, and dendritic cells, where the measurements were produced from an experiment run on a miRNA microarray and applying normalization procedures comprising:
  i. replacing outliers with mean signal values (gMean-Signal) greater than a threshold value of 60,000+ in the miRNA microarray with an average value imputed using all values for miRNAs that were below the threshold value so as to produce resulting signal values;
  ii. combining the resulting signal values into a single expression file with miRNA in rows and samples in columns;
  iii. normalizing values in the single expression file by applying Robust Multi-Array Average (RMA) and logging the normalized values to approximate a normal distribution for a first set of miRNAs measured on the microarray;
b. identifying a subset of miRNA most correlated with exosomes from B cells, CD4+ T cells, and dendritic cells comprising:
  i. selecting the subset of the miRNA of the first set that are most highly associated with cell type (B cell, CD4+ T cell, or dendritic cell) in the miRNA microarray by implementing a multiclass nonparametric Wilcoxon rank test and adjusting for multiple hypotheses testing using permutation-based tests to approximate a null distribution, resulting in selection of a first subset of the miRNAs of the first set with q-value<0.05:
c. fitting a support vector machine (SVM) with a linear kernel, of type nu-regression, with the normalized measurements from (a) for the miRNA identified in (b) comprising:
  i. inputting the expression file for the 105 miRNAs of the first subset and all EV samples from the miRNA microarray of step (a) (iii), and running SVM fitting function multiple times where each time one EV sample is kept as a new sample and other remaining EV samples are labeled and used to train the fitting function;
  ii. optimizing nu parameter by running the SVM fitting function over a range of nu input parameters, from 0.1 to 1.0 and selecting a nu value of about nu=0.25 that produced highest accuracies in predicting a true cell-of-origin label for each new EV sample;
d. using the trained SVM to predict cell of origin for new microarray measurements from extracted EVs comprising:
  i. inputting the vector of EV RNA expression for a new EV sample;
  ii. multiplying a coefficient vector from the fitted SVM by support vectors, using linear algebra multiplication notation in R, to create a modified coefficient vector; and
  iii. dividing the resulting modified coefficient vector by the sum of the modified coefficients to scale the cell fraction predictions to sum to 1, or 100% so as to obtain a predicted fractional amount of each cell type (B cells, CD4+ T cells, and dendritic cells) that contributed to the EVs present in the input sample, thus predicting the cell-of-origin of EVs into any one of a B cell, CD4+ T cell, or dendritic cell,
  wherein the first set of miRNAs comprises hsa-miR-620, hsa-miR-384, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-125a-3p, hsa-miR-125a-5p, hsa-miR-125b, hsa-miR-123b-1*, hsa-miR-125b-2*, hsa-miR-126, hsa-miR-126*, hsa-miR-127-3p, hsa-miR-127-5p, hsa-miR-128, hsa-miR-129-3p, hsa-miR-129-5p, hsa-miR-129*, hsa-miR-130a, hsa-miR-130a*, hsa-miR-130b, hsa-miR-130b*, hsa-milt-132, hsa-miR-132*, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-milt-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-55a*, hsa-miR-5b, hsa-milt-15b*, hsa-miR-16, hsa-miR-16-1*, hsa-miR-16-2*, hsa-miR-17, hsa-miR-17*, hsa-mil-181a, hsa-miR-181a-2*, hsa-miR-181a*, hsa-miR-181b, hsa-miR-181e, hsa-miR-181c*, hsa-miR-181d, hsa-miR-182, hsa-miR-182*, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-5p, hsa-miR-199b-3p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-30a, hsa-miR-30a*, hsa-miR-30b, hsa-miR-30b, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518b, hsa-miR-518c, hsa-miR-518e, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-527, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-665, hsa-miR-668, hsa-miR-671-3p, hsa-miR-671-5p, hsa-miR-675, hsa-miR-7, hsa-miR-7-1*, hsa-miR-7-2*, hsa-miR-708, hsa-miR-708*, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-801, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR- 885-5p, hsa-miR-886-3p, hsa-miR-886-5p, hsa-miR-887, hsa-miR-888, hsa-miR-888, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*;

wherein the 105 miRNAs of the first subset comprises hsa-miR-335, hsa-miR-17, hsa-miR-25, hsa-miR-363, hsa-miR-146h-5p, hsa-miR-20a, hsa-miR-320, hsa-miR-513b, hsa-miR-21, hsa-miR-20b, hsa-miR-30b, hsa-miR-193b, hsa-miR-342-3p, hsa-miR-221, hsa-miR-1224-5p, hsa-miR-93, hsa-miR-132, hsa-miR-29a, hsa-miR-92a, hsa-miR-29c, hsa-miR-23a, hsa-miR-19a, hsa-miR-365, hsa-miR-210, hsa-miR-155, hsa-miR-767-5p, hsa-miR-181a, hsa-miR-631, hsa-miR-223, hsa-miR-146a*, hsa-miR-146a, hsa-miR-519d, hsa-miR-22, hsa-miR-299-5p, hsa-miR 617, hsa-miR-148a, hsa-miR-609, hsa-miR-633, hsa-miR-128, hsa-miR-409-3p, hsa-miR-24, hsa-miR-106b, hsa-miR-671-3p, hsa-miR-767-3p, hsa-miR-197, hsa-miR-513c, hsa-miR-623, hsa-miR-130b, hsa-miR-19b, hsa-miR-625*, hsa-miR-129*, hsa-miR-1227, hsa-miR-18b*, hsa-miR-654-5p, hsa-miR-133a, hsa-miR-933, hsa-miR-181b, hsa-miR-15b, hsa-miR-579, hsa-miR-188-5p, hsa-miR-92b, hsa-miR-29b, hsa-miR-135a*, hsa-miR-574-3p, hsa-miR-494, hsa-miR-636, hsa-miR-181a-2*, hsa-miR-483-3p, hsa-miR-483-5p, hsa-miR-597, hsa-miR-937, hsa-miR-943, hsa-miR-602, hsa-miR-129-3p, hsa-miR-27a, hsa-miR-30c, hsa-miR-211, hsa-miR-1229, hsa-miR-125a-3p, hsa-miR-101, hsa-miR-559, hsa-miR-346, hsa-miR-563, hsa-miR-484, hsa-miR-331-3p, hsa-miR-150, hsa-miR-378, hsa-miR-513a-5p, hsa-miR-610, hsa-miR-220b, hsa-miR-125b-2*, hsa-miR-26b, hsa-miR-411*, hsa-miR-550, hsa-miR-1233, hsa-miR-606, hsa-miR-422a, hsa-miR-149, hsa-miR-324-3p, hsa-miR-181d, hsa-miR-33b*, hsa-miR-520g, hsa-miR-1234, hsa-miR-425, and hsa-miR-634.

2. The method of claim 1, further comprising the step of identifying a therapeutic candidate for packaging into exosomes as a delivery vehicle by determining the miRNA with the lowest q-value from step (b) thereby identifying the therapeutic candidate tor packaging into exosomes as a delivery vehicle.

3. The method of claim 1, wherein the vesicle is an exosome.

* * * * *